United States Patent [19]

Chen et al.

[11] 4,228,298

[45] Oct. 14, 1980

[54] 15-DEOXY-16-HYDROXY-16-FLUOROMETHYL, DIFLUOROMETHYL OR TRIFLUOROMETHYL PROSTAGLANDINS OF THE E AND F SERIES

[75] Inventors: Sow-Mei L. Chen, Parkridge, N.J.; Charles V. Grudzinskas, Nyack, N.Y.

[73] Assignee: American Cyanamid Company, Stamford, Conn.

[21] Appl. No.: 46,724

[22] Filed: Jun. 7, 1979

[51] Int. Cl.³ .................................................. C07C 177/00
[52] U.S. Cl. .................................. 560/121; 260/408; 260/429.7; 260/438.1; 424/305; 424/317; 556/471; 562/503; 518/843
[58] Field of Search ..................... 560/121; 562/503; 260/408

[56] References Cited

U.S. PATENT DOCUMENTS

4,163,016   7/1979   Holland et al. .................. 260/345.8

*Primary Examiner*—Robert Gerstl
*Attorney, Agent, or Firm*—Richard J. Hammond

[57] ABSTRACT

The invention disclosed herein relates to pharmacologically active prostaglandins of the E and F series in which C-16 is substituted with hydroxyl and fluoromethyl, difluoromethyl or trifluoromethyl as well as the pharmacologically acceptable, non-toxic lower alkyl esters and salts thereof, and to the intermediates and processes for producing such compounds.

12 Claims, No Drawings

15-DEOXY-16-HYDROXY-16-FLUOROMETHYL, DIFLUOROMETHYL OR TRIFLUOROMETHYL PROSTAGLANDINS OF THE E AND F SERIES

BACKGROUND OF THE INVENTION (1) Field of the Invention

The present invention relates to 15-deoxy-16-hydroxy-16-fluoromethyl, difluoromethyl or trifluoromethyl prostaglandins, as well as the pharmaceutically acceptable, non-toxic lower alkyl esters and salts thereof, and to the intermediates and processes for producing such compounds.

(2) Description of the Prior Art

Prostaglandins have classically been described as chemically relates 20 carbon chain hydroxy fatty acids having the basic skeleton of prostanoic acid:

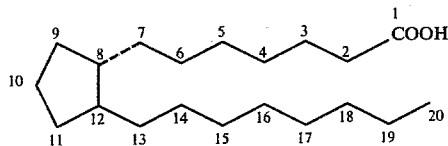

The prostaglandins having a hydroxyl group at the C-11 position and a keto group at the C-9 position are known as the PGE series, and those having a hydroxyl group in place of the keto group are known as the PGF series and are further designated by an $\alpha$ or $\beta$ suffix to indicate the configuration of the hydroxyl group at said position. The natural compounds are the $\alpha$-hydroxy substituted compounds. They may contain different degrees of unsaturation in the molecule, particularly at C-5, C-13 and C-17, the unsaturation is also indicated by a suffix. Thus, for example, the PGF$_1$ and PGE$_1$ series refer to prostanoic acids having a trans olefin bond at the C-13 position, while the PGF$_2$ and PGE$_2$ series refer to prostadienoic acids having a cis-olefin bond at the C-5 position and a trans olefin bond at the C-13 position. For a review on protaglandins and the definition of primary prostaglandins, see, for example, P. Ramwell *The Prostaglandins*, 1, pp. 5–22 (1973).

The preparation of derivatives of prostanoic acid has become of great importance since the demonstration of the highly interesting range of biological and pharmacological activities of natural prostaglandins.

The great majority of these studies have focused on modification of the two side chains, or modifications of the substituents attached to the cyclopentane moiety [see for example U. Axen et al., *Synthesis* Vol. 1, John Wiley and Sons Inc., New York, New York. 1973 and P. H. Bently, *Chem. Soc. Reviews*, 2, 29 (1973)].

The synthesis of prostaglandin analogs possessing a 3-oxa- or 11-deoxy-3-thia moiety have been described, among others in U.S. Pat. Nos. 3,873,607; 3,950,406; Netherlands Pat. No. 7305222-Q; U.S. Pat. Nos. 3,944,593; 3,931,289; and 3,936,487.

The synthesis of several prostaglandin analogs wherein the hydroxyl group at C-15 has been removed and a hydroxyl group has been introduced at C-16 has appeared [see for example, U.S. Pat. No. 3,950,406; *Prostaglandins*, Vol. 10, 733 (1975); *Tetrahedron Letters*, No. 48, 4217 (1975)].

Recently, reports have also appeared wherein the C-16 carbon bearing a hydroxyl group is substituted with a methyl group [see Pappo et al., *Tetrahedron Letters*, No. 4, 235 (1975); Collin et al., U.S. Pat. No. 3,965,143; and Belgium Pat. No. 827,127].

Also, a patent has recently appeared wherein the C-16 carbon bearing the hydroxyl group is substituted with vinyl, methylvinyl, and cyclopropyl (U.S. Pat. No. 4,061,670).

Prostaglandins incorporating the fluorine atom have also been described: 15-trifluoro-methyl-15-hydroxy (Germ. Offen. 2,357,781); 11,12-difluormethylene-15-hydroxy (Bel. Pat. No. 804-570); 2,2-difluoro-15-hydroxy (U.S. Pat. Nos. 4,001,300; 4,068,083; 4,065,633; and numerous others); 16,16-difluoro-15-hydroxy (Germ. Offen. 2,434,334 among others); 16-fluoro-15-hydroxy [*Prostaglandins*, 9, 527–530 (1975)]; 16-trifluormethyl-15-hydroxy (Japan: J5 0116-456); 20-trifluoro-15-hydroxy (U.S. Pat. No. 3,833,640) 2 or 3-fluoro-15-hydroxy (U.S. Pat. No. 3,922,297).

SUMMARY OF THE PRESENT INVENTION

In accordance with the present invention, we have prepared certain novel 15-deoxy-16-hydroxy-16-mono, di- and trifluoromethyl prostaglandin analogs represented by the following formula:

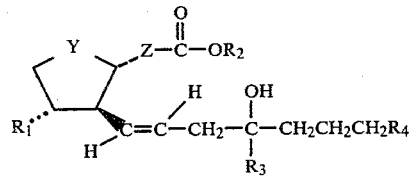

wherein Y is

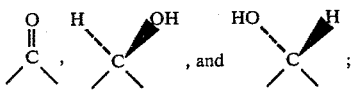

$R_1$ is selected from the group consisting of hydrogen and hydroxyl;

$R_2$ is selected from the group consisting of hydrogen and $C_1$-$C_6$ alkyl;

$R_3$ is selected from the group consisting of $CH_2F$, $CHF_2$, and $CF_3$;

$R_4$ is selected from the group consisting of hydrogen and $C_1$-$C_3$ alkyl;

Z is selected from the group consisting of a divalent moiety of the formulae: $-(CH_2)_n-$, $-(CH_2)_m-$, $-(CH_2)_mSCH_2-$, $-CH_2CH=CH(CH_2)_p-$ wherein n is 5 to 7, preferably 6, m is 3 to 5, preferably 4 and p is 2 to 4, preferably 3, the racemic mixture thereof; and when $R_1$ is hydrogen, the pharmacologically acceptable salts thereof.

The dotted lines shown in the above formula and in the formulas below indicate that the substituents are in configuration, i.e., below the plane of the cyclopentane ring.

The double bond at C-13 in the compounds of the present invention has the same configuration as in natural prostaglandins of the PGE and PGF series, that is the trans configuration.

These novel compounds possess asymmetric centers and thus can be produced as racemic mixtures or as individual enantiomers. The racemic mixtures can be resolved if desired at appropriate stages by methods known to those skilled in the art, to obtain the respective individual enantiomers. It is to be understood that the racemic mixtures and the individual 8R-enantiomers are encompassed within the scope of the present invention.

When the compounds of the present invention are racemic mixtures, they are produced starting from racemates, while when the compounds of the invention are individual enantiomers the compounds are preferably obtained starting from the appropriate individual enantiomer.

Useful pharmacologically acceptable salts of the above formula, where $R_1$ is hydrogen, are those with pharmacologically acceptable metal cations, ammonium, amine cations or quaternary ammonium cations.

Preferred metal cations are those derived from the alkali metals, e.g., lithium, sodium and potassium, and from the alkaline earth metals, e.g., magnesium and calcium, although cationic forms of other metals, e.g. aluminum, zinc and iron, are within the scope of this invention.

Pharmacologically acceptable amine cations are those derived from primary, secondary or tertiary amines such as mono-, di- or trimethylamine, ethylamine, dibutylamine, triisopropylamine, N-methylhexylamine, decylamine, dodecylamine, allyamine, crotylamine, cyclopentylamine, dicyclohexylamine, mono- or dibenzylamine, α- or β-phenyethylamine, ethylenediamine, and arylipatic amines containing up to and including 18 carbon atoms, as well as heterocyclic amines, e.g., piperidine, morpholine, pyrrolidine, piperazine and lower alkyl derivatives thereof, e.g. 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g. mono-, di-, or triethanolamine, ethyldiethanolamine, N-butylethanolamine, 2-amino-1-butanol, 2-amino-2-ethyl-1,3-propanediol, 2-amino-2-methyl-1-propanol, tris-(hydroxymethyl)-aminoethane, N-phenylethanolamine, N-(p-tert-amylphenyl)-diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium and the like.

DISCLOSURE

The novel compounds of this invention can be prepared by a 1,4-conjugate-addition procedure involving treatment of the ether blocked by cyclopentenone (14) with a lithio-cuprate reagent such as (11), (12) or (13) prepared as illustrated in Flowsheets A, B, C and D.

Although Flowsheets A, B and C exemplify the use of a trimethylsilyloxy protecting group, any protecting group which survives the conjugate addition reaction described by these tables and the examples of this application may be employed. Suitable protecting groups therefore include tri-($C_1$-$C_4$)-alkylsilyl, or other acid labile protecting groups such as tetrahydropyranyl, tetrahydrofuranyl, or other acetals. Moreover, with reference to the lithiocuprates of Flowsheet C (structures (15), (16) or (17)) in addition to the lithocuprates described, the lithiocuprates of structure (C) may also be employed.

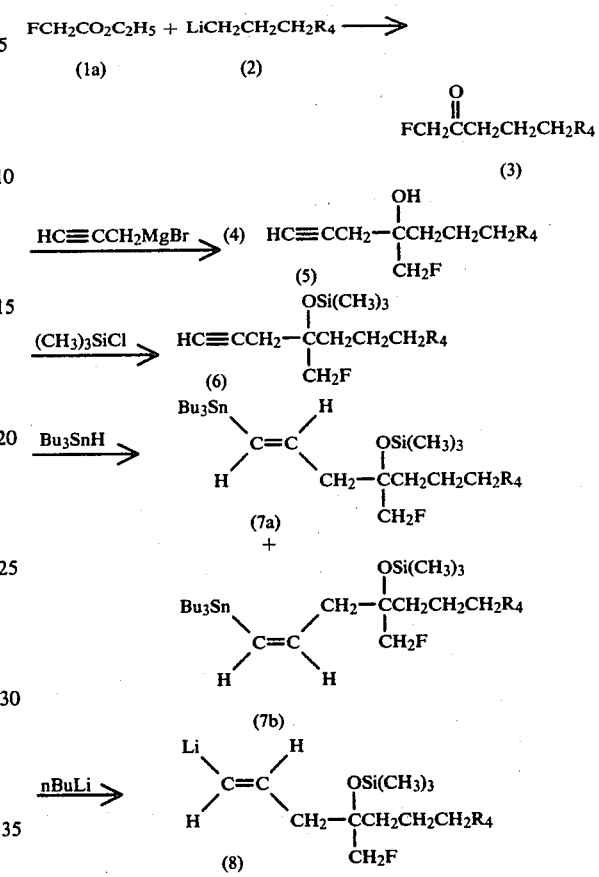

In accordance with the procedure outlined in Flowsheet A, treatment of ethyl monofluoroacetate (1) with alkyl lithium (2) wherein $R_4$ is hydrogen, methyl, ethyl or propyl provides the fluoroketone (3). Treatment of the ketone (3) with propargylmagnesium bromide (4) provides the hydroxyalkyne (5) which is silylated to give the ether (6). The TMS ether (6) is heated with tri-n-butylstannane in the presence of azobisisobutyronitrile (AIBN) to afford the trans vinylstannane (7a) which contains 10% to 20% of the corresponding cis vinylstannane (7b).

Treatment of the vinylstannyl reagents (7a) with n-butyl lithium at temperatures of −78° C. to −10° C. generates the vinyl lithium reagents (8).

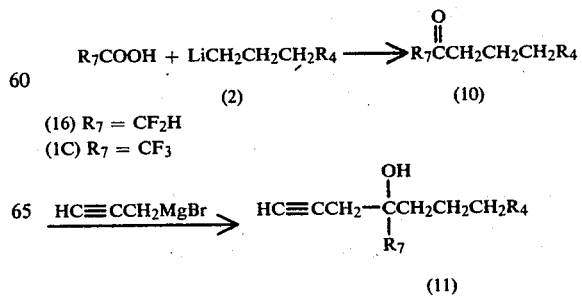

FLOWSHEET B

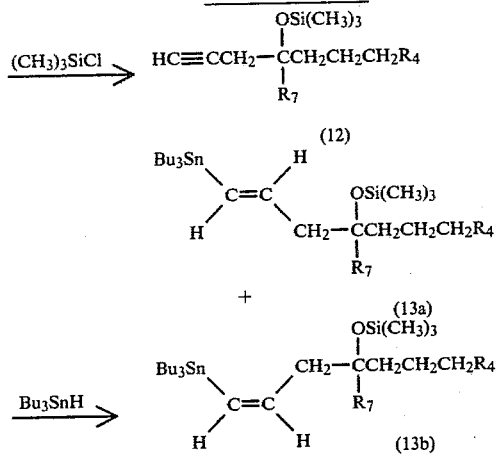

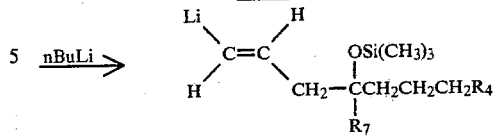

In accordance with Flowsheet B the treatment of difluoroacetic acid (1b) or trifluoroacetic acid (1c) with an alkyl lithium (2) wherein $R_4$ is hydrogen, methyl ethyl or propyl, provides the ketone (10) which upon addition of propargylmagnesium bromide provides the hydroxyalkyne (11). The alcohol (11) is treated with chlorotrimethylsilane to provide the TMS-ether (12) which is heated with tri-n-butylstannane to provide the trans-vinylstannane (13a) that contains 10% to 20% of the corresponding cis-vinylstannane (13b).

Treatment of the vinylstannane reagents (13a) with n-butyl lithium at temperatures of $-78°$ C. to $-10°$ C. generates the vinyl lithium reagents (14).

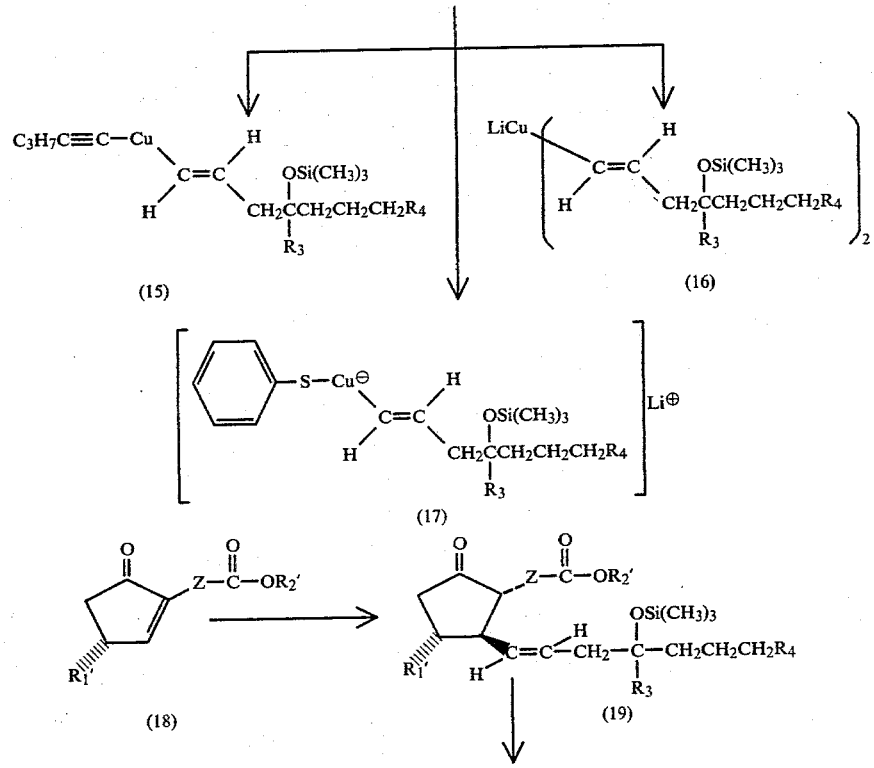

FLOWSHEET C wherein $R_2'$ is lower alkyl $C_1$-$C_6$, tetrahydropyranyl, or trilower-($C_1$-$C_3$) alkylsilyl;
$R_1'$ is hydrogen, tetrahydropyranyloxy, or trilower ($C_1$-$C_3$) alkylsilyloxy;
$R_1$, $R_2$ are as hereinabove defined;
Z is $(CH_2)_n$, $(CH_2)_m OCH_2$, $$(CH_2)_m SCH_2 \text{ or } \overset{cis}{\underset{H \quad H}{CH-C=C-(CH_2)_p}}$$

wherein m,n and p are as previously defined.

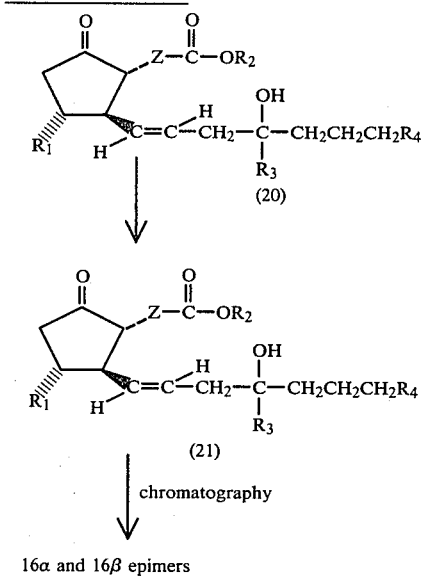

-continued

↓

(21)

↓ chromatography

16α and 16β epimers

In accordance with Flowsheet C for the preparation of the asymmetrical lithio-cuprate (15) wherein $R_3$ is as previously defined or the like, a solution of one molar equivalent of copper (I)-1-alkyne, preferably copper (I)-1-pentyne in anhydrous tributylphosphine or HMPTA, preferably one to five molar equivalents, in ether is added to one molar equivalent of the aforementioned vinyl lithium solution cooled to about −78° C. After about one hour at this temperature, a molar equivalent of the requisite cyclopentenone (18) is added. After several hours at −30° C. to −70° C. the reaction mixture is quenched with aqueous ammonium chloride solution and the blocked product (19) is isolated in the usual manner.

It is also possible to effect conjugate 1,4-addition with the asymmetrical lithio-cuprate (17) wherein $R_3$ is as previously defined derived from vinyl lithium and cuprous thiophenoxide. A solution of vinyl lithium (8) or (14) in ether at −78° C. is reacted with an equimolar amount of a reagent prepared by admixture, in ether at a temperature of 0° C. to −78° C., of equimolar amounts of cuprous thiophenoxide and copper (I) iodide tributylphosphonium complex. After about 30 minutes at this temperature, the lithio-cuprate (17) is treated with the requisite cyclopentenone (18) as described hereinabove for the conjugate addition with 1-alkynyl lithio-cuprate (16).

For the preparation of the symmetrical lithio-cuprate (16) wherein $R_3$ is as previously defined one molar equivalent of copper (I) iodide tributylphosphine complex, dissolved in anhydrous ether, is added at about −78° C. to two molar equivalents of the aforementioned vinyl lithium (8) or (14) solution cooled to −78° C. After about one hour at this temperature, the lithio-cuprate (16) is treated with the requisite cyclopentenone (18) as described hereinabove for the conjugate addition with the 1-alkynyl lithio-cuprate (15).

The procedures for conjugate addition, involving organocopper reagents are well known in the art, see for example C. J. Sih, et al, *J. Amer. Chem. Soc.* 97, 865 (1975) which is incorporated by reference.

In the cases where $R'_1$=trimethylsilyloxy in cyclopentenone (18) the conjugate addition is performed at −78° C. to −40° C. The reaction is quenched by addition of an ether solution of acetic acid. Removal of blocking groups is then carried out as described in the reference above to provide the product (20) wherein $R_1$, $R_2$, $R_3$ and $R_4$ are as hereinabove.

In order to remove the trimethylsilyl protecting group from the C-16-hydroxyl of (20) more acidic conditions are required than for a non-fluorinated carbinol, the addition of a small amount of hydrochloric acid is necessary to provide (21) accompanied by the corresponding PGA derivative.

The introduction of a racemic β-chain possessing the 16-hydroxy-16-mono, di- and trifluoromethyl moieties provides a pair of prostaglandins epimeric at C-16. These two epimers may be separated into their upper (less polar) and lower (more polar) components by high-pressure liquid chromatography (HPLC) or by dry-column or preparative thin layer silica-gel chromatography.

In an optically active protected cyclopentenone such as (18) is utilized, then HPLC separation will provide the corresponding optically active nat. 9-oxo-11α,16α-dihydroxy-16-mono-, di- and trifluoromethyl- PGE and nat. 9-oxo-11α,16β-dihydroxy-16-mono-, di- and trifluoromethyl-PGE enantiomers.

All available evidence leads us to believe that the

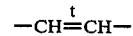

function introduced by the cuprate process occupies a position trans to the 11-oxy function. Similarly, we are led to the conclusion that in the product (19) the two side-chains attached to $C_8$ and $C_{12}$ are trans to each other. However, we are not certain of this configurational relationship in the product as it is obtained directly from the cuprate process. These products may have the side-chains in a trans-or cis-relationship or they may be a mixture containing both the trans- and cis-isomers. This is indicated in the nomenclature of the compounds involved by the designation 8 ξ. In order to ensure a trans-relationship in (19) these products can be submitted to conditions known in the literature to equilibrate the cis-8-iso-PGE$_1$ to a mixture containing about 90% of the trans product. These conditions involve treatment with potassium acetate in aqueous methanol for 96 hours at room temperature.

The triloweralkylsilyloxy substituted lithio-cuprate reagents of type (8) and (14) and the trialkylstannyl precursors are novel and useful compounds which are also embraced by this invention. They may be defined by generic formulae (B) and (C).

(22C). Treatment of the chloroalcohol (22C) with ethylmercaptoacetate furnishes the hydroxyester (22D) which upon hydrolysis with sodium formate/formic acid provides the 3-hydroxy-cyclopentenone (22E). Treatment of the cyclopentenone (22E) with sulfuric acid provides the required 4-hydroxy-cyclopentenone (22F) which after treatment with chlorotrimethylsilane provides the bissilylated cyclopentenone (22G).

FLOWSHEET D

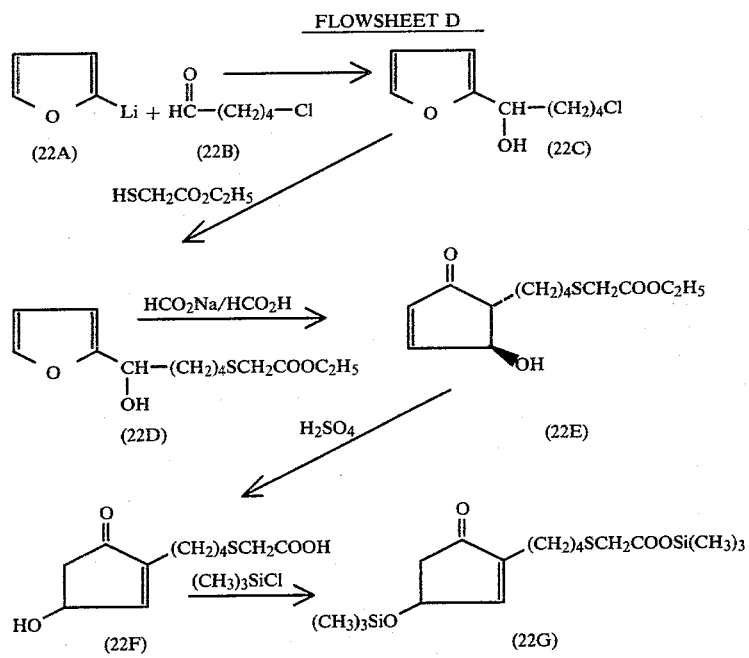

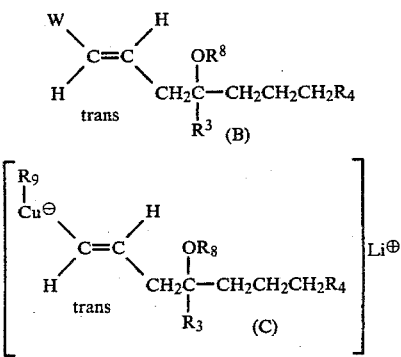

wherein W is R-Sn wherein R is tri($C_1$-$C_6$)alkyl and preferably a tri-n-butyl group, or W is lithium; $R_8$ is tri($C_1$-$C_4$)alkylsilyl, preferably trimethylsilyl or other acid labile protecting groups such as tetrahydropyranyl, tetrahydrofuranyl or other acetals; $R_9$ is thiophenoxide, substituted thiophenoxide wherein the substituent may be $C_{1-4}$Calkyl, $C_1$-$C_4$alkoxy, $C_1$-$C_3$dialkylamino or phenyl, or $R_9$ may be $C_3$-$C_4$alkyne or the identical vinyl moiety.

The cyclopentenones required for the preparation of the $E_1$, $E_2$, 3-oxa, and 11-deoxy-3-thia series have been described in the literature. The cyclopentenone for the preparation of 3-thia-11-hydroxy prostaglandins is described in Flowsheet D.

In accordance with Flowsheet D which is hereinbelow described, treatment of 2-furyl lithium (22A) with a ω-chloroaldehyde (22B) provides the chloroalcohol In accordance with Flowsheet E, when the 11-hydroxy or 11-oxy derivatives are treated with dilute acid, it is possible to effect elimination and the formation of the corresponding $\Delta^{10}$ derivatives (22H) of the prostaglandin A-type. A preferred procedure involves treatment in tetrahydrofuran:-water (2:1) solvent 0.5N in HCl for about 30 hours at ambient temperature. Under these conditions a tetrahydropyranyl or trialkylsilyl ester or ether will undergo hydrolysis.

FLOWSHEET E

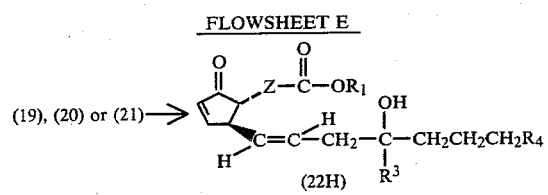

The prostaglandin carboxylic acids of this invention can be readily converted to the various alkyl esters of this invention by treatment in the usual manner with the appropriate diazoalkane. The preparation of diazoalkanes by various procedures are well described in the art. See for example, C. D. Gutsche, *Organic Reactions*, VIII, 389 (1954). Certain of the esters of this invention can also be obtained directly by use of the appropriate cyclopentenone ester. The various esters can also be prepared by any of several procedures well-known in the art via an acid chloride (prior blocking of free alcohol groups with appropriate blocking groups such as trialkylsilyl, tetrahydropyranyl and the like) or mixed anhydrides and treatment of these intermediates with the appropriate alcohol. Mixed anhydrides can be obtained by treatment of the prostaglandin acid in a solvent such as dioxane at a temperature in the range of 0° C. to 15° C. with a molar equivalent of a tri-alkylamine, preferably triethylamine, tributylamine and the like, and then a molar equivalent of isobutyl chlorocarbonate or the like. The resulting mixed anhydrides are then treated with the appropriate alcohol to give the derivatized product. [For a pertinent literature analogy see *Prostaglandins*, 4, 768 (1973).]

An alternative procedure involves treatment of the prostaglandin acid with a molar equivalent of the trialkyl amine in an excess of the appropriate alcohol in an anhydrous solvent such as methylene chloride, molar equivalent of p-toluenesulfonyl chloride is then added (if necessary, a second molar equivalent can be added) and after stirring at ambient temperatures for about 15 minutes to one hour the product is worked-up in the usual manner. (For a pertinent literature analogy, see U.S. Pat. No. 3,821,279.) A third procedure involves the use of dicyclohexylcarbodiimide in the usual manner; for a pertinent literature analogy see *German Offen.* 2,365,205; *Chem. Abst.*, 81, 120098g (1974).

The esterified alcohol derivatives of this invention are also prepared in the usual manner by procedures well known in the art from the appropriate alkanoic acid anhydride or acid chloride.

When the compounds of this invention are prepared from racemic starting compounds, two racemates are obtained. In appropriate instances these racemates may be separated from each other by careful application of the usual chromatographic procedures. In the more difficult instances it may be necessary to apply high pressure liquid chromatography including recycling techniques. [See G. Fallich, American Laboratory, 19-27 (August 1973) as well as references cited therein. Additional information, concerning high speed liquid chromatography and the instruments necessary for its application, is available from Waters Associate Inc., Maple Street, Milford, Mass.]. Treatment of a prostaglandin of the E series (9-oxo) (D) with a carbonyl reducing reagent such as sodium borohydride provides a mixture of the corresponding $PGF_\alpha$ (9α-hydroxy) (E) and $PGF_{62}$ (9β-hydroxy) (F) analogs. These two epimeric alcohols are readily separated by silica gel chromatography.

If one utilized the individual 16α-hydroxy or 16β-hydroxy (E) starting material after separating the 9β product as above, the isolated products are the 9α,16α-dihydroxy and 9α,16β-dihydroxy derivatives, respectively.

Use of a stereoselective reagent such as lithiumperhydro-9b-boraphenalylhydride [H. C. Brown and W. C. Dickason, *J.A.C.S.*, 92, 709 (1970)] or lithium tri-sec-butylborohydride [H. C. Brown and S. Krishnamurthy, Ibid, 94, 7159 (1972)] provides the $PGF_\alpha$ product as the selective species.

Likewise, utilization of either the individual 16α- or 16β-hydroxy (E) compounds affords the corresponding 9α, 16α-di-hydroxy and 9α,16β-dihydroxy prostaglandins of this invention.

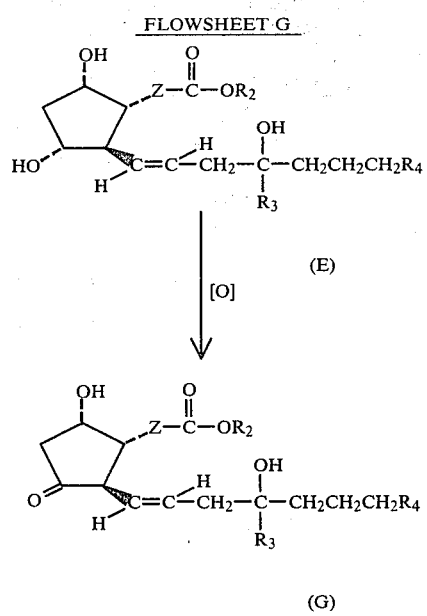

(G)

In accordance with Flowsheet G when 11α-hydroxy-$PGF_{2\alpha}$ congeners such as (E) are treated with an oxidizing reagent such as Jones Reagent, or pyridinium chlorochromate provides a selective oxidation to give the corresponding PGD derivative (9α-hydroxy-11-keto). (G) is isolated after chromatographic purification.

If one utilized the individual 16α-hydroxy or 16β-hydroxy PGFα derivative of (E), then the corresponding 9α,16α dihydroxy-11-oxo and 9α,16β-dihydroxy-11-oxo-prostaglandins are isolated, respectively.

In the following formulae Z is as hereinabove defined.

The 4-hydroxycyclopentenone racemates may be resolved into their component enantiomers (23) and (24) wherein Z is as hereinabove defined by derivatizing the ketone function with a reagent having an optically active center. The resulting diastereoisomeric mixture can then be separated by fractional crystallization, or by chromatography, or by high speed liquid chromatography involving, if necessary, recycling techniques. Among the useful optically active ketone derivatizing regents are 1-α-aminoxy-β-methylpentanoic acid hydrochloride (to give (25)), (R)-2-aminoxy-3,3-dimethylbutyric acid hydrochloride, and 4-α-methylbenzyl semicarbazide. After separation of the diastereomeric derivatives, reconstitution of the keto function provides the individual 4-hydroxycyclopentenone enantiomers (23) and (24). A useful procedure for the resolution of a 4-hydroxycylopentenone racemate via an oxime such as (25) is described in the art [R. Pappo, P. Collins and C. Jung, *Tetrahedron Letters*, 943 (1973)]. The resolution of the hydroxycyclopentenone (23) wherein Z is

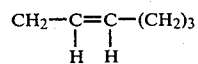

is described by Bruhn et al, *Tetrahedron Letters*, 235 (1976).

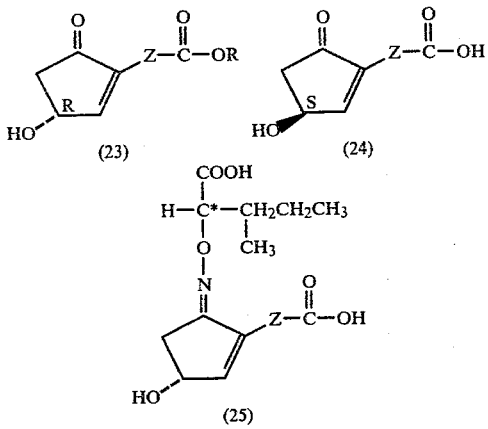

The novel compounds of the present invention have potential utility as hypotensive agents, anti-ulcer agents, agents for the treatment of gastric hypersecretion and gastric erosion, agents to provide protection against the ulcerogenic and other gastric difficulties associated with the use of various nonsteroidal anti-inflammatory agents (e.g., indomethacin, aspirin, and phenylbutazone), bronchodilators, anti-inflammatory agents, abortifacients, agents for the induction of labor, agents for the induction of menses, fertility-controlling agents, oestrus regulators for use in animal husbandry with cattle and other domestic animals and central nervous system regulatory agents. Certain of the novel compounds of this invention possess utility as intermediates for the preparation of the other novel compounds of this invention.

The novel compounds of this invention possess the pharmacological activity described below as associated with the appropriate above-described prostaglandin types.

The known PGE, PGF$\alpha$, PGF$\beta$, PGA and PGD compounds are all potent in causing multiple biological responses even at low doses. For example, PGE$_1$, PGE$_2$, PGA$_1$ and PGA$_2$ are extremely potent in causing vasodepression and smooth muscle stimulation, and also are potent as antilipolytic agents. Moreover, for many applications, these known prostaglandins have an inconveniently short duration of biological activity. In striking contrast, the novel prostaglandin analogs of this invention are substantially more specific with regard to potency in causing prostaglandin-like biological responses, and/or having a substantially longer duration of biological activity. For example, the 11-deoxy-PGE compounds of this invention are selective in that they are at most relatively weak stimulants of smooth muscle. A further advantage of these novel compounds should be in their stabilities and lengthened shelf-lives.

Therefore, each of these novel prostaglandin analogs of this invention should be more useful than one of the corresponding above-mentioned known prostaglandins for at least one of the pharmacological purposes indicated below for the latter, either because it has a different and narrower spectrum of biological activity than the known prostaglandins, and therefore is more specific in its activity and causes smaller and fewer undesired side effects than the known prostaglandins, or because of its prolonged activity, fewer and smaller doses of the novel prostaglandin analog can frequently be used to attain the desired result.

Another advantage of the novel compounds of this invention, compared with the known prostaglandins, is that these novel compounds are administered effectively orally, sublingually, intravaginally, buccally, or rectally, in addition to the usual intravenous, instramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

PGE$_1$, PGE$_2$, PGE$_3$, dihydro-PGE$_1$, PGF$\alpha$, PGF$\beta$ and PGA compounds, their esters and pahrmacologically acceptable salts, are extremely potent in causing various biological responses. For that reason, these compounds are useful for pharmacological purposes. See, for example, Bergstrome, et al., *Pharmacol. Rev.*, 20, 1 (1968), and references cited herein. A few of those biological responses are systemic arterial blood pressure lowering in the case of the PGA and PGE compounds as measured, for example, in anesthetized (sodium phenobarbital) pentolinium-treated rats with indwelling aortic and right heart cannulas; pressor activity, similarly measured, for the PGF compounds; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of PGE compounds, as shown in dogs with secretion stimulted by food or histamine infusion; activity on the central nervous system; decrease of blood platelet adhesiveness in the case of PGE, as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen, and in the case of the PGE and PGA compounds, stimulation of epidermal proliferation and kerathinization, as shown when they are applied in culture to embryonic chick and rat skin segments.

Because of these biological responses, these known prostaglandins are useful to study, prevent, control, or alleviate a wide variety of disease and undesirable physiological conditions in birds and mammals including humans, useful domestic animals, pets, and zoological specimens, and in laboratory animals, e.g., mice, rats, rabbits, and monkeys.

For example, these compounds are useful in mammals, including man, as nasal decongestants. For this purpose, the compounds are used in a dose range of about 0.01 mg to about 10 mg per ml of a pharmacologically suitable liquid vehicle or as an aerosol spray, both for topical application.

PGA, PGF$\beta$ and PGE compounds are useful as hypotensive agents to reduce blood pressure in mammals including man. For this purpose, the PGF$\beta$ compounds are administered by intravenous infusion at the rate of about 0.01 mg to about 40 mg per Kg of body weight per minute, or in a single dosage or multiple doses of about 25 mg to 2500 mg per Kg of body weight total per day. The PGE and PGA compounds are administered by intravenous infusion at the rate of about 0.01 to about 50 mg per Kg of body weight per minute, or in a single dose or multiple doses of about 25 to 2500 mg per Kg of body weight total per day.

The PGE, PGF$_\alpha$ and PGF$_\beta$ compounds ar useful in place of oxytocin to induce labor in pregnant female animals, including humans, cows, sheep and pigs, at or near term or in pregnant animals with intrauterine death of the fetus from about 20 weeks to term. For this purpose, the PGF compound is infused intravenously at a dose of 0.01 mg to 50 mg per Kg of body weight per minute until or near the termination of the second stage of labor, i.e., expulsion of the fetus. Similarly, the PGE compound is infused intravenously at a dose of 0.01 to 50 mg per Kg of body weight per minute until or near the expulsion of the fetus. These compounds are especially useful when the female is one or more weeks postmature and natural labor has not started, or 12 to 60 hours after the membranes have ruptured and natural labor has not yet started.

The PGE, PGF$_\alpha$ and PFG$_\beta$ compounds are useful for controlling the reproductive cycle in ovulating female mammals, including humans and other animals. For that purpose, PGF$_{2\alpha}$, for example, is administered systemically at a dose level in the range of 0.01 mg to about 20 mg per Kg of body weight, advantageously during a span of time starting approximately at the time of ovulation and ending approximately at the time of menses or just prior to menses. Likewise, a PGE compound is administered in the same fashion at a dose level of 0.01 mg to about 50 mg per Kg of body weight. Additionally, expulsion of an embryo or fetus is accomplished by similar administration of the compound during the first third or the second third of the normal mammalian gestation period. Accordingly, such compounds are useful as abortifacients. They are also useful for induction of menses during approximately the first two weeks of a missed menstrual period and thus, are useful as contraceptive anti-fertility agents.

11$_\alpha$-hydroxy-PGE compounds are extremely potent in causing stimulation of smooth muscle, and are also highly active in potentiating other known smooth muscle stimulators, for examle, oxytocic agents, e.g., oxytocin, and the various ergot alkaloids including derivatives and analogs thereof. Therefore PGE, for example, is useful in place of or in combination with less than usual amounts of these known smooth muscle stimulators for example, to relieve the symptoms of paralytic ilueus, to control or prevent uterine bleeding after abortionor delivery, to aid in expulsion of the placenta, and during the puerperium. For the latter purpose, the PGE compound is administered by intravenous infusion immediately after abortion or delivery at a dose in the range about 0.01 to about 50 mg per Kg of body weight per minute until the desired effect is obtained. Subsequent doses are given by intravenous, subcutaneous, or intramuscular injection or infusion during puerperium in the range of 0.01 to 2 mg per Kg of body weight per day, the exact dose depending on the age, weight, and condition of the patient or animal.

The novel PGA, PGE and PGF$_\beta$ of this invention are also useful as bronchodilators for the treatment of asthma and chronic bronchitis. As such they may be conveniently administered by inhalation of aerosol sprays prepared in a dose range of about 10 μg to about 10 mg/ml of a pharmacologically suitable liquid vehicle. Relative to the natural prostaglandins, the PGA and PGE compounds in particular have the significant advantge of inducing prolonged effects.

The PGE and PGA compounds are also useful in mammals, including man and certain useful animals, e.g., dogs and pigs, to reduce and control excessive gastric secretion, thereby reducing or avoiding gastric erosion or gastrointestinal ulcer formation, and accelerating the healing of such ulcers already present in the gastrointestinal tract. For this purpose, the compounds are injected or infused intravenously, subcutaneously, or intramuscularly in an infusion dose range of about 0.1 mg to about 500 mg per Kg of body weight per minutes, or in a total daily dose by injection or infusion in the range of about 0.1 to about 20 mg per Kg of body weight per day, the exact dose depending on the age, weight, and condition of the patient or animal, and on the frequency and route of administration. These compounds may also be useful in conjunction with various non-steroidal anti-inflammatory agents, such as aspirin, phenylbutazone, indomethacin and the like, to minimize the well-known ulcerogenic effects of the latter.

The PGE and PGA compounds also stimulate epidermal proliferation and keratinization, and in such a capacity are useful to promote and accelerate healing of skin which has been damaged, for example, by burns, wounds, abrasions or surgery. The action of the PGA compounds makes them particularly useful in speeding the adherence and growth of skin autografts, especially small, deep (Davies) grafts which are intended to cover skinless areas by subsequent outward growth rather than initially, and in retarding rejection of homografts.

For these purposes, these compounds are preferably administered topically at or near the site where cell growth and keratin formation is desired, advantageously as an aerosol liquid or micronized powder spray, as an isotonic aqeuous solution in the case of wet dressings, or as a lotion cream, or ointment in combination with the usual pharamaceutically acceptable dilutents. In some instances, when there is substantial fluid loss as in the case of extensive burns or skin loss due to other causes, systemic administration of PGE is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. Illustrative of a wet dressing for topical application to second and/or third degree burns of skin area 5 to 25 square centimeters is the use of an isotonic aqueous solution containing one to 50 mg/ml of the PGA compound or several times that concentration of the PGE compound. Especially for topical use, these prostaglandins are useful in combination with antibiotics such as gentamycin, neomycin, polymyxin B, bacitracin, spectinomycin, and oxytetracycline; with other antibacterials such as mafenide hydrochloride, sulfadiazine, furazolium chloride, and nitrofurazone; and with corticoid steroids, such as hydrocortisone, prednisolone, methylprednisolone, and fluoroprednisolone; each of those being used in the combination at the usual concentration suitable for its use alone.

The PGA compounds and derivatives and salts thereof increase the flow of blood in the mammalian kidney, thereby increasing the volume and electrolyte conent of the urine. For that reason, PGA compounds are useful in managing cases of renal disfunction, especially in cases of severely impaired renal blood flow, for example, the hepatorena syndrome and early kidney transplant rejection. In case of excessive or inappropriate antidiuretic hormone ADH vasopressin secretion, the diuretic effect of these compounds is even greater. In anephretic states, the vasopressin action of these compounds is especially useful.

The PGE compounds of this invention are also useful as topical vasodilators.

The $PGE_1$ compounds of this invention are useful whenever it is desired to inhibit platelet aggregation, to reduce the adhesive character of platelets, and to remove or prevent the formation of thrombi in mammals including man, rabbits, and rats. For example, these compounds are useful to treat and prevent myocardial infarcts and post-operative thrombosis. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range of about 0.005 to about 20 mg per Kg of body weight per day are used, the exact dose depending on the age, weight, and condition of the patient or animal, and on the frequency and route of administration.

It is well known that platelet aggretatio inhibitors may be useful as anti-thrombotic drugs. Inhibition of patelet aggregation can be conveniently measured in vitro by monitoring changes in optical density and/or light transmission in platelet rich plasma upon addition of suitable aggregating agents such as adenosine diphosphate, epinephrine, thrombin or collagen. Alternatively, platelet aggregation can be measured in vitro using platelet rich plasma obtained at various time intervals from animals given inhibitors by an oral or parenteral route.

The PGE compounds of the present invention exhibit the ability to inhibit platelet aggregation in vitro when tested by the following procedure.

Human protein rich plasma is incubated with modified Tyrode's solution in a proportion of 40-50% human protein rich plasma. The test compounds are added at varying concentrations and after 5 minutes incubation, an aggregating agent such as adenosine diphosphate or collagen is added. The change in optical density (light transmission) is monitored by eye and inhibition is recorded as a (−) or lack of inhibition is recorded as a (+). Test compounds are considered active if they inhibit adenosine diphosphate or collagen induced aggreation at a concentration of 0.025 mg/ml of less within 5-10 minutes.

The PGE compounds of this invention also have bronchodilator activity as determined in a test using dogs anesthetized, artificially ventilated and submitted to a continuous respiratory spasm induced by pilocarpine.

Mongrel dogs of either sex weighing between 5 and 10 kg are used. They are premedicated with morphine HCl by subcutaneous injection at 1.5 mg/Kg. An intravenous perfusion of 5% (W/V) chloralose is started ½ hour after the morphine injection in such a way that 60 mg/Kg are administered within 15 minutes. After completion, a continuous perfusion of 10 mg/Kg/hour is maintained throughout the experiment. The dogs are artificially ventilated by means of a Starling pump at a rate of 20 breaths/ minute. The volume is adjusted according to the weight of the animal. [Kleinman and Radford, *J. Appl. Physiol.,* 19, 360 (1964)]. All the measurements are made with the dogs positioned supine in a heated, V-shaped table. Curarization is obtained by succinylcholine chloride using a starting injection of 3 mg/Kg lasting 3 minutes, followed by a continuous perfusion of 0.1 mg/Kg/minute.

The respiratory spasm is induced by a starting injection of 400 mcg/Kg of pilocarpine HCl lasting 5 minutes. An increase or decrease in the dose of pilocarpine HCl may occur as a function of the observed effect on the airway's resistance. A 15 minute delay is observed before the start of a continuous perfusion of pilocarpine HCl at a dose of 4 mcg/Kg/minute to maintain a constant spasm during the test.

A metallic cannula is inserted and fixed, after tracheotomy, into the upper part of the trachea. The two cephalic veins and the two femoral veins are catheterized to inject the varius agents. The femoral artery is catheterized to measure the systemic blood pressure. An esophageal balloon (11 cm×2.5 cm) is inserted into the lower third of the oesophagus to measure the endothoracic pressure. The measurement of air flow is made with a Fleish pneumotachograph connected to the tracheal tube.

The transpulmonary pressure is measured as follows: The tracheal cannula is equipped with a stainless steel axial tube (1.5 mm) which is closed at its distal end and projected 2.5 cm beyond the end of the cannula. Three holes with a diameter of one mm are pierced on this latter segment. This tube, which is used to measure the tracheal pressure, is connected to one of the two chambers of a Sanborn 267 B/C differential transducer. The other chamber is connected to the esophageal ballon by means of a polyethylene catheter of the same length and characteristics as the balloon's.

The airflow is measured from the Fleish pneumotachograph by means of a Sanborn 270 differential transducer.

The tidal volume is obtained by electronic integration of the flow signal using an R.C. integrator.

The systemic and pulmonary blood pressures are gauged by means of a Sanborn 267 B/C or 1280B pressure transducer.

An electrocardiogram is taken in lead 2. Its use is to monitor a cardiac rate-meter.

All these parameters are recorded on a Sanborn polygraph. The transpulmonary pressure and the tidal volume are also displayed as rectangular coordinates on an oscilloscope.

The airway's resistance, expressed in cm of water/liter/second, is measured by subtracting from the electrical equivalent of the transpulmonary pressure, a voltage proportional to the flow so as to synchronize the pressure and volume signals on the oscilloscope [Mead and Whittenberger, *J. Appl. Physiol.,* 5 779 (1953)].

The value of the pulmonary elastance, expressed in cm of water/liter, is obtained by means of the same principle, analogical computer which allows the direct reading, cycle to cycle, of the values of resistance and elastance.

The test compounds are administered by an Aerosol ® route. The microneubulizer of a Bird Mark 7 respirator is fitted on the metallic cannula just after the pneumotachograph. The "puff" of the test compound, in Aerosol ® is driven by a 2 $Kg/cm_2$ pressure, allowed into the microneubulizer just during one inspiration cycle. The microneubulizer is fitted on the respiratory tube only during the "puff." It is weighed just before and just after administration to determine the amount of test compound administered. Approximately 50 mg of the solution is administered to each dog. In accordance with the Pilocarpine Assay described herein, the compounds of this invention should exhibit bronchodilator activity.

The bronchodilator activity for representative compounds of this invention was determined in Guinea-Pigs against bronchospasms elicited by intravenous injections of serotonin, histamine, and acetylcholine, by the Konzett procedure the details of which are those discussed by J. Lulling, P. Lievens, F. El Sayed and J. Prignot, *Arzeimittel-Forschung* 18, 995 (1968).

In the table which follows, bronchodilator activity for representative compounds of the invention against spasmogenic agents serotonin, histamine, and acetylcholine is expressed as an $ED_{50}$ determined from the results obtained with three logarithmic cumulative intravenous doses.

TABLE A

| | KONZETT DATA | | |
|---|---|---|---|
| | SPASMOGEN ED 50 Mg/Kg | | |
| COMPOUND | Serotonin | Histamine | Acetylcholine |
| dl 15-deoxy-16-fluoromethyl-16-hydroxy-$PGE_2$ | $1.38 \times 10^{-3}$ | $2.57 \times 10^{-3}$ | $1.94 \times 10^{-3}$ |
| dl 15-deoxy-16-difluoromethyl-16-hydroxy-$PGE_2$ | $4.6 \times 10^{-3}$ | $2.78 \times 10^{-3}$ | $4.04 \times 10^{-3}$ |
| dl 15-deoxy-16-trifluoromethyl-16-hydroxy-$PGE_2$ | $7.96 \times 10^{-3}$ | $4.15 \times 10^{-3}$ | $10.0 \times 10^{-3}$ |

REFERENCE EXAMPLE 1

1-Fluoro-2-hexanone

A solution of 26.5 g. of ethyl fluoroacetate in 350 ml. of ether is cooled in a dry ice-ethanol bath under nitrogen. To this is added 250 ml. of a solution comprising 110 ml. of 2.67M n-butylmagnesium chloride in tetrahydrofuran which has been diluted with 140 ml. of ether, dropwise through a dropping funnel over a period of one hour. During this addition, the temperature of the reaction mixture is maintained at −65° C. to −72° C. After complete addition, 100 ml. of 15% aqueous sulfuric acid is added and the mixture is stirred at room temperature for one hour. The ether portion of the mixture is separated, washed with water, then brine, dried and then concentrated on a rotary evaporator at about 15° C. The concentrated solution is distilled through a Vigorox column to remove a fore-run (b.p. 40°-80° C./760 mm) and then the product is collected at 30°-35° C./14 mm.

REFERENCE EXAMPLE 2

4-Fluoromethyl-4-hydroxy-1-octyne

A 0.25 ml. portion of propargyl bromide is added to a stirred suspension of 0.73 g. of magnesium and 6 mg. of mercuric chloride in 7.5 ml. of ether. The reaction is initiated after a few minutes of vigorous stirring at room temperature. A mixture of 3 g. of 80% 1-fluoro-2-hexanone and 3.63 g. of propargyl bromide in 7.5 ml. of ether is added dropwise through a dropping funnel so that the reaction remains gently refluxing (25° C. to 32° C.). Cooling in a water bath is required. The reaction mixture is cooled in an ice bath, quenched with 8 ml. of cold saturated aqueous ammonium chloride, filtered through Celite and washed with ether. The mother liquor is evaporated to dryness giving a reddish oily residue, which is Kugheror-distilled at 45° C./4 mm giving the product as a colorless liquid.

REFERENCE EXAMPLE 3

4-Fluoromethyl-4-trimethylsilyloxy-1-octyne

To a solution of 4.38 g. of 4-fluoromethyl-4-hydroxy-1-octyne and 4.8 g. of imidazole in 19 ml. of dimethylformamide, cooled in an ice bath under nitrogen, is added 4.5 ml. of trimethylchlorosilane via a syringe during a few minutes. The mixture is stirred in the ice bath for 30 minutes and then at room temperature under nitrogen overnight. The solution is poured into hexane, washed with saturated aqueous sodium bicarbonate, water, then brine and dried over anhydrous sodium sulfate. The solvents are removed in vacuo giving the product as a colorless liquid.

REFERENCE EXAMPLE 4

4-Fluoromethyl-4-trimethylsilyloxy-1-tri-n-butylstannyl-trans-1-octene

A solution of 6.36 g. of 4-fluoromethyl-4-trimethylsilyloxy-1-octyne, 11.64 g. of (10.6 ml.) of tributylstannane and 40 mg. of azobisisobutyronitrile is heated and stirred at 120° C. under nitrogen for 3 hours. The mixture is cooled, filtered through Celite and washed with hexanes. The hexanes are removed in vacuo and the residual liquid is vacuum distilled through a short path. The product is obtained at b.p. 110°-135° C./0.2-0.25 mm. (The product contains a minor amount of cis isomer.)

REFERENCE EXAMPLE 5

9-Oxo-11α,16-dihydroxy-16-fluoromethyl-5-cis-13-trans-prostadienoic acid

To a solution of 4.9 g. of 4-fluoromethyl-4-trimethylsilyloxy-1-tri-n-butylstannyl-1-octene in 4.5 ml. of tetrahydrofuran at −78° C. under nitrogen, is added 4.92 ml. (1.91 M) n-butyl lithium over a period of 15 minutes. The resulting yellow solution is stirred at −50° C. to −40° C. for one hour and then at −40° C. to −30° C. for 30 minutes. After cooling to −78° C., a solution of 1.25 g. of pentynylcopper and 4.68 ml. of tri-n-butylphosphine in 9 ml. of ether is added during 20 minutes. The solution is stirred at −78° C. for 2 hours, then a solution of 2-(6-carbotrimethylsiloxyhex-2-cis-enyl)-4-trimethylsiloxycyclopent-2-en-1-one in 5 ml. of ether is added during 20 minutes. The mixture is stirred at −40° C. to −50° C. for one hour, then at −40° C. to −30° C. for 30 minutes. The solution is recooled to −60° C. and quenched by pouring into a mixture of 200 ml. of ice-cold saturated aqueous ammonium chloride solution, 200 ml. of ether and 3 ml. of glacial acetic acid and stirred vigorously for 20 minutes. After standing overnight in a refrigerator the mixture is extracted with ether-ethyl acetate. The combined organic extracts are washed with dilute hydrochloric acid, water, then brine and evaporated to dryness in vacuo. The residue is treated with a mixture of 50 ml. of glacial acetic acid, 25 ml. of tetrahydrofuran and 12.5 ml. of water and stirred at room temperature under nitrogen for one hour. The mixture is diluted with 150 ml. of toluene and evaporated in vacuo to dryness, giving a brownish liquid. This liquid is applied to 25 g. of silica-gel and washed with 200 ml. of hexane followed by 200 ml. of ethyl acetate. The ethyl acetate extract is passed through a dry-column (880 g. silica-gel 2″×68″) eluting with 60% ethyl-acetate, 0.5% acetic acid in hexane, collecting 200 ml. The product is washed off the silica-gel with ethyl acetate which is evaporated to dryness in vacuo, giving 515 mg. of the desired product, 690 mg. of 15-deoxy-16-fluoromethyl-16-trimethylsiloxy-PGE$_2$, and 550 mg. of a mixture of the two above products.

REFERENCE EXAMPLE 6

Hydrolysis of 9-oxo-11α-hydroxy-16-fluoromethyl-16-trimethylsiloxy-5-cis-13-trans-prostadienoic acid to 9-oxo-11α,16α-dihydroxy-16-fluoromethyl-5-cis-13-trans-prostadienoic acid and 9-oxo-11α,16β-dihydroxy-5-cis-13-trans-prostadienoic acid A 560 mg. portion of 15-deoxy-16-fluoromethyl-16-trimethylsiloxy-PGE$_2$ in a mixture of 8 ml. of tetrahydrofuran, 4 ml. of water, 16 ml. of acetic acid and 3 drops of 4 N hydrochloric acid is stirred and heated at 35° C. for 2 hours. The mixture is diluted with ether and the aqueous layer is extracted with ethyl acetate. The organic layers are combined and then washed with water and brine several times. The solution is then diluted with toluene and concentrated in vacuo to dryness giving an oil. This oil is purified through a dry-column [silica-gel (300 g.) 1 3/16"×60"] eluting with 60 % ethyl acetate, 0.5% acetic acid in hexane. One hundred ml. of eluate is collected giving 9-oxo-11α,16-dihydroxy-16-fluoromethyl-5-cis-13-trans-prostadienoic acid as an oil. This oil is separated into the 16α and 16β-hydroxy components by high pressure liquid chromatography.

REFERENCE EXAMPLE 7

1,1-Difluoro-2-hexanone

To a 3 liter, three-neck, round bottom flask, equipped with a magnetic stirrer, a dropping funnel filled with 39.9 g. of difluoroacetic acid and 200 ml. of ether, and a rubber septum is added 1350 ml. of ether. After cooling in a dry ice-acetone bath under nitrogen, one mole of n-butyl lithium (2.2 M, hexane) is added via a double tip needle. The difluoroacetic acid solution is slowly added to the cooled n-butyl lithium solution via the dropping funnel over 3 hours. The thick mixture is stirred at −78° C. for one hour and then quenched by pouring into a mixture of one liter of 4 N hydrochloric acid and one liter of ice, divided into three flasks, with stirring. The organic layers are combined and washed with water and brine. The 1500 ml. of solution is distilled at atmospheric pressure in a water bath. After the forerun is collected, the residue is fractionally distilled giving 18.8 g (b.p. 100°–110° C.) of product that is 75% real.

REFERENCE EXAMPLE 8

4-Difluoromethyl-4-hydroxy-1-octyne

To a stirred suspension of 3.6 g. of magnesium and 30 mg. of mercuric chloride in 0.33 ml. of ether is added 1.5 ml. of propargyl bromide. The mixture is stirred vigorously for several minutes to initiate reaction, then a solution of 15.5 g. of 1,1-difluoro-2-hexanone and 12.1 ml. of propargyl bromide in 33 ml. of ether is added slowly (dropwise) over a 1.5 hour period, so that the mixture remains gently refluxing (25°–30° C.). After addition, the mixture is stirred at room temperature for 30 minutes, then cooled in an ice bath to 0°–5° C. and quenched by adding 35 ml. of saturated ammonium chloride solution dropwise (exothermic) and stirred for 30 minutes. The mixture is filtered through Celite and washed with ether. The filtrate is concentrated in vacuo giving a yellow oil. This oil is vacuum distilled at 71° C., 12 mm giving the product as 10.54 g. of colorless oil which becomes pale yellow on standing at room temperature.

REFERENCE EXAMPLE 9

4-Difluoromethyl-4-trimethylsiloxy-1-octyne

A solution of 11.5 g. of 4-difluoromethyl-4-hydroxy-1-octyne and 11.32 g. of imidazole in 45 ml. of dimethylformamide is cooled in an ice bath under nitrogen. A 10.3 ml. portion of trimethylchlorosilane is added using a syringe over a 15 minute period. The mixture is stirred in the ice bath for one hour and then overnight at room temperature. The solution is diluted with hexane and then poured into saturated aqueous sodium bicarbonate solution. The hexane solution is separated, washed with aqueous sodium bicarbonate solution and brine, dried over anhydrous sodium sulfate and the solvents are evaporated to dryness giving the desired product as a colorless liquid.

REFERENCE EXAMPLE 10 trans-4-Difluoromethyl-4-trimethylsiloxy-1-tri-n-butylstannyl-1-octene

A mixture of 13.0 g. of 4-difluoromethyl-4-trimethylsiloxy-1-octyne, 17.23 ml. of tri-n-butylstannane and 70 mg. of azobisisobutyronitrile is heated under nitrogen in an oil bath at 125°–135° C. for 2 hours. The reaction is cooled to room temperature and vacuum distilled through a short-path apparatus, giving, after a 5 ml. forerun, 25.6 g. of the product as an oil, containing a minor amount of the corresponding cis isomer.

REFERENCE EXAMPLE 11

9-Oxo-11α-hydroxy-16-difluoromethyl-16-trimethylsiloxy-5-cis-13-trans-prostadienoic acid To a solution of 5.33 g. of 4-difluoromethyl-4-trimethylsiloxy-1-tri-n-butylstannyl-trans-1-octene in 5 ml. of dimethylformamide at −78° C., under nitrogen, is added 4.67 ml. of 1.8 M n-butyl lithium in hexane, during 30 minutes. The mixture is stirred at −78° C. for 10 minutes, then at −40° C. to −50° C. for one hour, then at −40° to −30° C. for 30 minutes. The mixture is recooled at −78° C. and is added to a solution of 1.29 g. of pentynylcopper and 4.95 ml. of tri-n-butylphosphine in ether during 15 minutes. The resulting solution is stirred at −78° C. in a dry-ice-acetone bath for 1.5 hours and then added to a solution of 2-(6-carbotrimethylsiloxyhex-2-cis-enyl)-4-trimethylsiloxycyclopent-2-en-1-one in 5 ml. of ether during 20 minutes. The resulting mixture is stirred at −78° C. for 10 minutes, then at −40° to −50° C. for one hour and then at −40° to −30° C. for 30 minutes. After recooling to −60° C., the reaction is quenched by pouring into a cold mixture of 200 ml. of saturated aqueous ammonium chloride, 150 ml. of ether and 3 ml. of acetic acid. The mixture is stirred vigorously for 20 minutes, stored overnight in a refrigerator and the aqueous layer is extracted with ethyl acetate. The combined ether-ethyl acetate solution is washed with dilute hydrochloric acid, water and brine and concentrated in vacuo to brownish liquid. This liquid is dissolved in a mixture of 50 ml. of acetic acid, 25 ml. of tetrahydrofuran and 12.5 ml. of water and stirred, under nitrogen, at room temperature for one hour. The mixture is diluted with 150 ml. of toluene and concentrated in vacuo to a brown oil. This oil is applied to 25 g. of silica gel, washed with 200 ml. of hexane followed by 200 ml. of ethyl acetate. The ethyl acetate wash is passed through a dry column (880 g. silica gel, 2"×68"), eluting with 40% ethyl acetate, 0.5% acetic acid in hexane, collecting 50 ml. of eluant. The column is cut up to provide 1.31 g. of 9-oxo-11α-hydroxy-16-difluoromethyl-16-trimethylsiloxy-5-cis-13-trans-prostadienoic acid.

REFERENCE EXAMPLE 12

Hydrolysis of
9-oxo-11α-hydroxy-16-difluoromethyl-16-trimethyl-siloxy-5-cis-13-trans-prostadienoic acid to
9-oxo-11α,16α-dihydroxy-16-difluoromethyl-5-cis-13-trans-prostadienoic acid and
9-oxo-11α,16β-dihydroxy-16-difluoromethyl-5-cis-13-trans-prostadienoic acid A mixture of 1.1 g. of 15-deoxy-16-difluoromethyl-16-trimethylsiloxy-PGE$_2$, 28 ml. of acetic acid, 14 ml. of tetrahydrofuran, 7 ml. of water and 5 drops of 4 N hydrochloric acid is stirred at 35° C. for 2 hours. The mixture is cooled to room temperature, diluted with ether and washed with water. The combined ether extract is washed with water and brine and evaporated to dryness in the presence of 50 ml. of toluene giving 1.3 g. of an oily residue. This residue is passed through a dry column (500 g. silica gel, 1 ⅝"×63"), eluting with 40% ethyl acetate, 0.5% acetic acid in hexane. Two hundred ml. of eluant is collected. From sections of the dry-column, 900 mg. of 9-oxo-11α,16-dihydroxy-16-difluoromethyl-5-cis-13-trans-prostadienoic acid is isolated. This is separated by high pressure liquid chromatography to provide 9-oxo-11α,16α-dihydroxy-16-difluoromethyl-5-cis-13-trans-prostadienoic acid and 9-oxo-11α,16β-dihydroxy-16-difluoromethyl-5-cis-13-trans-prostadienoic acid.

REFERENCE EXAMPLE 13

1,1,1-Trifluoromethyl-2-hexanone

A mechanically stirred solution of 57 g. of trifluoroacetic acid in one liter of anhydrous ether, under argon, is cooled to −78° C. and treated with one mole of n-butyl lithium (2.2 M in hexane) over a 2¼ hour period. After an additional 1¼ hours, the reaction mixture becomes gelatinous and stirring is discontinued. The reaction mixture, on standing overnight under an argon atmosphere, becomes fluid and stirring is continued for 2 hours. The solution is then syphoned into an agitated mixture of 200 ml. of concentrated hydrochloric acid and approximately one liter of cracked ice. The ether layer is separated, washed with saturated saline solution, then saturated sodium bicarbonate solution and dried over anhydrous magnesium sulfate. The ether is distilled at atmospheric pressure and the residue is fractionally distilled, giving 7.8 g. of the desired product, b.p. 75°–85° C.

REFERENCE EXAMPLE 14

4-Trifluoromethyl-4-hydroxy-1-octyne

To a stirred mixture of 1.78 g. of magnesium and approximately 25 mg. of mercuric chloride in 10 ml. of dry ether is added 0.6 ml. of propargyl bromide. The reaction is initiated by gentle warming. The refluxing solution is cooled in an ice bath and treated with a solution of 4.8 ml. of propargyl bromide and 10.85 g. of 1,1,1-trifluoromethyl-2-hexanone in 7 ml. of dry ether by dropwise addition over an 80 minute period maintaining the reaction temperature between 10° and 15° C. The mixture is stirred for 1¾ hours at room temperature, then recooled and terminated with 10 ml. of saturated ammonium chloride solution. The mixture is filtered through Celite and washed copiously with ether. The filtrate is washed with saturated saline solution, dried over anhydrous potassium carbonate-magnesium sulfate and evaporated to an oil. Fractional distillation of the oil at 12 mm pressure afforded 5.5 g. of the desired product, b.p. 65°–70° C.

REFERENCE EXAMPLE 15

4-Trifluoromethyl-4-trimethylsiloxy-1-octyne

A stirred solution of 4.99 g. of 4-trifluoromethyl-4-hydroxy-1-octyne and 5.65 g. of imidazole in 28 ml. of dry dimethylformamide, under argon, is cooled in an ice bath and then treated with 5.2 ml. of trimethylsilyl chloride by dropwise addition over a period of about 20 minutes. After an additional 15 minutes at ice bath temperature, the reaction mixture is stirred at room temperature overnight. The mixture is then poured into approximately 150 ml. of hexane and washed with small portions of ice cold water and saturated saline solution. The solution is dried over anhydrous magnesium sulfate and evaporated under reduced pressure to give the desired product.

REFERENCE EXAMPLE 16 trans-4-Trifluoromethyl-4-trimethylsiloxy-1-tri-n-butyl-stannyl-1-octene

A stirred mixture of 6.66 g of 4-trifluoromethyl-4-trimethylsiloxy-1-octyne and 26 mg. of azabisisobutyronitrile, under argon, is treated with 6.95 ml. of tri-n-butyl tin hydride, via a syringe. After treatment, a condenser is attached to the reaction vessel and the reaction mixture, under argon, is slowly heated to 130°–135° C. and maintained at that temperature for 1.5 hours. Subsequent fractional distillation of the reaction mixture at approximately 0.07 mm pressure gives the desired product, b.p. 125°–135° C. (containing a minor amount of the corresponding cis isomer).

REFERENCE EXAMPLE 17

9-Oxo-11α-hydroxy-16-trifluoromethyl-16-trimethyl-siloxy-5-cis-13-trans-prostadienoic acid To a solution of 5.29 g. of 4-trifluoromethyl-4-trimethylsiloxy-1-tri-n-butylstannyl-trans-1-octene in 5 ml. of tetrahydrofuran at −78° C. is added 4 ml. of a solution of 2.4 M n-butyl lithium in hexane via a syringe. The resulting solution is stirred at −50° C. to −40° C. for one hour, then at −40° to −30° C. for an additional 30 minutes. After recooling to −78° C., a solution of 1.24 g. of pentynylcopper and 4.75 ml. of tri-n-butylphosphine in 9 ml. of ether is added and the mixture is stirred at −78° C. for 2 hours. To this solution at −78° C. is added a solution of 2.94 g. of 2-(6-carbotrimethylsiloxyhex-2-cis-enyl)-4-trimethylsiloxycyclopent-2-en-1-one in 5 ml. of ether. The resulting solution is stirred at −40° to −30° C. for 90 minutes, then recooled to −60° C. and quenched by pouring into an ice-cold mixture of 200 ml. of saturated aqueous ammonium chloride solution and 200 ml. of ether. After stirring vigorously for 30 minutes, the aqueous layer is separated and extracted with ethyl acetate. The organic phases are combined, washed with dilute hydrochloric acid, water and brine and concentrated in vacuo to a brown residue. This residue is stirred with a mixture of 50 ml. of acetic acid, 25 ml. of tetrahydrofuran and 12.5 ml. of water at room temperature, under nitrogen for 90 minutes. The solution is diluted with 100 ml. of toluene and concentrated in vacuo, providing a green oil which is applied to 42 g. of silica R cc-7 and washed with 250 ml. of hexane followed by 250 ml. of ethyl acetate. The ethyl acetate wash is concentrated and then passed through a dry-column (900 g. silica gel, 2"×70") eluting with ethyl acetate:hexane:acetic acid (40:60:0.5) providing 1.76 g. of 9-oxo-11α-hydroxy-16-trifluoromethyl-16-trimethylsiloxy-5-cis-13-trans-prostadienoic acid.

REFERENCE EXAMPLE 18

Hydrolysis of 9-oxo-11α-hydroxy-16-trifluoromethyl-16-trimethylsiloxy-5-cis-13-trans-prostadienoic acid to provide 9-oxo-11α,16α-dihydroxy-16-trifluoromethyl-5-cis-13-trans-prostadienoic acid and 9-oxo-11α,16β-dihydroxy-16-trifluoromethyl-5-cis-13-trans-prostadienoic acid A solution of one gram of 9-oxo-11α-hydroxy-16-trifluoromethyl-16-trimethylsiloxy-5-cis-13-trans-prostadienoic acid in a mixture of 30 ml. of acetic acid, 15 ml. of tetrahydrofuran, 7.5 ml. of water and 5 drops of 4 N hydrochloric acid is stirred at 40° C., under nitrogen, for 6 hours. This solution is diluted with toluene and concentrated in vacuo. The residue is dissolved in ether, washed thoroughly with water and brine, dried and concentrated in vacuo. The residue is passed through a dry column (500 g. silica gel, 1⅝"×63") and eluted with ethyl acetate:hexane:acetic acid (60:40:0.5). The product is washed off with ethylacetate. This chromatography provides 110 mg. of the lower 16-isomer; 100 mg. of the upper 16-isomer; 120 mg. of the upper isomer containing a minor amount of the lower isomer; and 380 mg. of the lower C-16 isomer containing some of the upper C-16 isomer. The fractions containing a mixture can be separated by high pressure liquid chromatography to provide 9-oxo-11α,16α-dihydroxy-16-trifluoromethyl-5-cis-13trans-prostadienoic acid and 9-oxo-11α,16β-dihydroxy-16-trifluoromethyl-5-cis-13-trans-prostadienoic acid.

REFERENCE EXAMPLE 19

Treatment of the starting carbonyl of Table B with the alkyl lithium reagent indicated provides the fluoroketones of the table, which upon subsequent treatment with propargyl magnesium bromide, provides the indicated hydroxy-alkynes, which are treated with trimethylchlorosilane by the procedure indicated to provide the alkyne-trimethylsiloxy ethers which upon treatment with tri-n-butylstannane provide the corresponding trans-vinylstannanes of the table. (Each trans-vinylstannane contains 10–20% of the corresponding cis-vinylstannane).

TABLE B

| Starting Carbonyl | Alkyl-Lithium | Fluoroketone | Hydroxy-Alkene | Alkyne-Tri-Methylsil-Oxy-Ether | Trans-Vinyl Stannane |
|---|---|---|---|---|---|
| trifluoro-acetic acid | n-propyl | 1,1,1-trifluoro-2-pentanone | 4-trifluoromethyl-4-hyydroxy-1-heptyne | 4-trifluoro-methyl-4-trimethyl-siloxy-1-heptene | 1-trans-tri-n-butyl-stannyl-4-trifluoro-methyl-4-trimethyl-siloxy-1-heptene |
| difluoro-acetic acid | n-propyl | 1,1-difluoro-2-pentanone | 4-difluoromethyl-4-hydroxy-1-heptyne | 4-difluoro-methyl-4-trimethyl-siloxy-1-heptyne | 1-trans-tri-n-butyl-stannyl-4-difluoro-methyl-4-trimethyl-siloxy-1-heptene |
| ethyl fluoroacetate | n-propyl | 1-fluoro-2-pentanone | 4-fluoromethyl-4-hydroxy-1-heptyne | 4-fluoro-methyl-4-trimethyl-siloxy-1-heptyne | 1-trans-tri-n-butyl-stannyl-4-fluoro-methyl-4-trimethyl-siloxy-1-heptene |
| trifluoro-acetic acid | n-pentyl | 1,1,1-trifluoro-2-heptanone | 4-trifluoromethyl-4-hydroxy-1-nonyne | 4-trifluoro-methyl-4-trimethyl-siloxy-1-nonyne | 1-trans-tri-n-butyl-stannyl-4-trifluoro-methyl-4-trimethyl-siloxy-1-nonene |
| difluoro-acetic acid | n-pentyl | 1,1-difluoro-2-heptanone | 4-difluoromethyl-4-hydroxy-1-nonyne | 4-difluoro-methyl-4-trimethyl-siloxy-1-nonyne | 1-trans-tri-n-butyl-stannyl-4-difluoro-methyl-4-trimethyl-siloxy-1-nonene |
| ethyl fluoroacetate | n-pentyl | 1-fluoro-2-heptanone | 4-fluoromethyl-4-hydroxy-1-nonyne | 4-fluoro-methyl-4-trimethyl-siloxy-1-nonyne | 1-trans-tri-n-butyl-stannyl-4-fluoro-methyl-4-trimethyl-siloxy-1-nonene |
| trifluoro-acetic acid | n-hexyl | 1,1,1-trifluoro-2-octanone | 4-trifluoromethyl-4-hydroxy-1-decyne | 4-trifluoro-methyl-4-trimethyl-siloxy-1-decyne | 1-trans-tri-n-butyl-stannyl-4-trifluoro-methyl-4-trimethyl-siloxy-1-decene |
| difluoro-acetic acid | n-hexyl | 1,1-difluoro-2-octanone | 4-difluoromethyl-4-hydroxy-1-decyne | 4-difluoro-methyl-4-trimethyl-siloxy-1-decyne | 1-trans-tri-n-butyl-stannyl-4-difluoro-methyl-4-trimethyl-siloxy-1-decene |
| ethyl fluoroacetate | n-hexyl | 1-fluoro-2-octanone | 4-fluoromethyl-4-hydroxy-1- | 4-fluoro-methyl-4- | 1-trans-tri-n-butyl-stannyl-4-fluoro- |

TABLE B-continued

| Starting Carbonyl | Alkyl-Lithium | Fluoroketone | Hydroxy-Alkene | Alkyne-Tri-Methylsil-Oxy-Ether | Trans-Vinyl Stannane |
|---|---|---|---|---|---|
| | | | decyne | trimethyl-siloxy-1-decyne | methyl-4-trimethyl-siloxy-1-decene |

REFERENCE EXAMPLE 20

PREPARATION OF 9α, 11α, 16-TRIHYDROXY-16-TRIFLUOROMETHYL-5-CIS, 13-TRANS-PROSTADIENOIC ACID

To a stirred solution of 9-oxo-11α, 16-di-hydroxy-16-trifluoromethyl-5-cis, 13-trans-prostadienoic acid in tetrahydrofuran (THF) at −78° C. is added an excess of a 0.5 M solution of lithium perhydro-9-boraphenalyl hydride in THF. After 30 min. at −78° C., the solution is warmed to 0° C. and treated with water. This mixture is partitioned with ether-potassium carbonate solutions. The aqueous phase is carefully acidified with hydrochloric acid, saturated with NaCl, and extracted with ethyl acetate. The organic extract is washed with brine, dried with magnesium sulfate, and concentrated in vacuo.

The residue is subjected to silica-gel dry column chromatography to provide 9α,11α,16-trihydroxy 16-trifluoro-methyl-5-cis, 13-trans-prostadienoic acid which may be separated into the individual 16α- and 16β- hydroxyl isomers by HPLC techniques.

REFERENCE EXAMPLE 21

PREPARATION AND SEPARATION OF 9α,11α,16-TRIHYDROXY-16-TRIFLUOROMETH-YL-13-TRANS-PROSTENOIC ACID AND 9β,11α,16-TRIHYDROXY-16-TRIFLUOROMETH-YL-13-TRANS-PROSTENOIC ACID

To a stirred, ice-cold solution of 9-oxo-11α, 16-dihydroxy-trifluoromethyl-13-trans-prostenoic acid in ethanol is added excess sodium borohydride in small portions during 1 minute. The mixture is stirred at 0° C. for 5 minutes and at ambient temperature for 1.5 hours. The bulk of the ethanol is evaporated in vacuo at room temperature and the residue is partitioned with cold, very dilute, hydrochloric acid and ethyl acetate. The organic phase is evaporated and washed with water and brine and dried over magnesium sulfate and concentrated in vacuo.

The residue is subjected to silica-gel chromatography to give: first eluted 9α, 11α, 16-trihydroxy-16-trifluoromethyl-13-trans-prostenoic acid followed by 9β, 11α, 16-trihydroxy-16-trifluoromethyl-13-trans-prostenoic acid.

If one starts with the individual 16α or 16β-hydroxy isomer, then the corresponding products will also be 16α or 16β-hydroxy, respectively.

REFERENCE EXAMPLE 22

PREPARATION OF 9-OXO-16-HYDROXY-16-TRIFLUOROMETHYL-5, CIS, 10,13-TRANS-PROSTATRIENOIC ACID 9-oxo-11α,16-dihydroxy-16-trifluoromethyl-5-cis, 13-trans-prostadienoic acid is dissolved in a 1:1 tetrahydrofuran-water mixture containing 0.5 N HCl and allowed to stand at ambient temperature under argon for 72 hours. The solution is treated with brine and extracted with ether. The extract is washed with brine, dried over magnesium sulfate, and concentrated in vacuo to an oil. This residue is purified by dry column chromatography to give 9-oxo-16-hydroxy-16-trifluoromethyl-5-cis, 10, 13-trans-prostatrienoic acid. It one utilizes the individual 16α or 16β isomer, the product obtained is the 16α or 16β-epimer respectively.

REFERENCE EXAMPLE 23

PREPARATION OF 9α,16-DIHYDROXY-11-OXO-16-FLUOROMETH-YL-13-TRANS-PROSTENOIC ACID

To a solution of 9α,11α,16-trihydroxy-16-fluoromethyl-13-trans-prostenoic acid in acetone (12 ml/g.) at −35° C. is added, dropwise with stirring, one equivalent of Jones Reagent (2.67 g CrO₃ and 2.3 ml of conc. H₂SO₄ diluted to 10 ml with water). After 15 min isopropanol is added, followed by water. The mixture is poured into water, saturated with NaCl, extracted with ethyl acetate, dried over magnesium sulfate, and concentrated in vacuo to an oil.

This oil is chromatographed on a dry column of silica-gel using ethyl acetate/heptane mixtures containing 1% acetic acid, to provide the product above.

If one starts with ether of the individual 16α- or 16β-hydroxyl isomers, one isolates the 16α- or 16β-hydroxyl isomer, respectively.

Although in Tables I and II which follow, the products listed are the dl-racemic products, as discussed above when the product is an optically active cyclopentenone (i.e. such as structure 12), the application of HPLC, column, or thin layer chromatography will provide the individual nat. 16α and nat. 16β compounds.

TABLE C

CYCLOPENTENONES

A. 2-(5-Carbotrimethylsiloxypent-2-cis-enyl)-4-trimethylsiloxycyclopent-2-en-1-one
B. 2-(6-Carbotrimethylsiloxyhex-2-cis-enyl)-4-trimethylsiloxycyclopent-2-en-1-one
C. 2-(7-Carbotrimethylsiloxyhept-2-cis-enyl)-4-trimethylsiloxycyclopent-2-en-1-one
D. 2-(5-Carbotrimethylsiloxypentyl)-4-trimethylsiloxycyclopent-2-en-1-one
E. 2-(6-Carbotrimethylsiloxyhexyl)-4-trimethylsiloxycyclopent-2-en-1-one
F. 2-(7-Carbotrimethylsiloxyheptyl)-4-trimethylsiloxycyclopent-2-en-1-one
G. 2-(6-Carbotrimethylsiloxy-5-thiahexyl)-4-trimethylsiloxycyclopent-2-en-1-one
H. 2-(6-Carbotrimethylsiloxy-5-oxa-hexyl)-4-trimethylsiloxycyclopent-2-en-1-one
I. 2-(6-Carbotrimethylsiloxyhex-2-cis-enyl)-4R-trimethylsiloxycyclopent-2-en-1-one
J. 2-(6-Carbotrimethylsiloxyhexyl)-4R-trimethylsiloxycyclopent-2-en-1-one
K. 2-(5-Carboethoxypent-2-cis-enyl)-cyclopent-2-en-1-one L. 2-(6-Carboethoxyhex-2-cis-enyl)-cyclopent-2-en-1-one
M. 2-(7-Carboethoxyhept-2-cis-enyl)-cyclopent-2-en-1-one
N. 2-(5-Carboethoxypentyl)cyclopent-2-en-1-one
O. 2-(Carboethoxyhexyl)cyclopent-2-en-1-one
P. 2-(7-Carboethoxyheptyl)cyclopent-2-en-1-one
Q. 2-(6-Carboethoxy-5-thiahexyl)cyclopent-2-en-1-one
R. 2-(6-Carboethoxy-5-oxahexyl)cyclopent-2-en-1-one

TABLE I

Treatment of the appropriate cyclopentenones of Table C with the lithiocuprates derived from the vinylstannanes or vinyl iodides of Reference Examples 4, 10, 16 and 19 by the procedure of Reference Examples 5 and 6, 11 and 12, 17 and 18 is productive of the $PGE_1$ derivatives of Examples 1–84 of Table I.

| EXAMPLE | VINYL TIN | CYCLOPENTENONE | PRODUCT PROSTAGLANDIN OF THE PGE$_1$ SERIES |
|---|---|---|---|
| 1 | 1-trans-tri-n-butylstannyl-4-fluoromethyl-4-trimethylsiloxy-1-heptene | 2-(5-carbotrimethylsiloxypentyl)-4-trimethylsiloxycyclopent-2-en-1-one | dl-11α,16-dihydroxy-9-oxo-16-fluoromethyl-20-nor-2-nor-13-trans prostenoic acid |
| 2 | 1-trans-tri-n-butylstannyl-4-difluoromethyl-4-trimethylsiloxy-1-heptene | 2-(5-carbotrimethylsiloxypentyl)-4-trimethylsiloxycyclopent-2-en-1-one | dl-11α,16-dihydroxy-9-oxo-16-difluoromethyl-20-nor-2-nor-13-trans prostenoic acid |
| 3 | 1-trans-tri-n-butylstannyl-4-trifluoromethyl-4-trimethylsiloxy-1-heptene | 2-(5-carbotrimethylsiloxypentyl)-4-trimethylsiloxycyclopent-2-en-1-one | dl-11α,16-dihydroxy-9-oxo-16-trifluoromethyl-20-nor-2-nor-13-trans prostenoic acid |
| 4 | 1-trans-tri-n-butylstannyl-4-fluoromethyl-4-trimethylsiloxy-1-octene | 2-(5-carbotrimethylsiloxypentyl)-4-trimethylsiloxycyclopent-2-en-1-one | dl-11α,16-dihydroxy-9-oxo-16-fluoromethyl-2-nor-13-trans prostenoic acid |
| 5 | 1-trans-tri-n-butylstannyl-4-difluoromethyl-4-trimethylsiloxy-1-octene | 2-(5-carbotrimethylsiloxypentyl)-4-trimethylsiloxycyclopent-2-en-1-one | dl-11α,16-dihydroxy-9-oxo-16-difluoromethyl-2-nor-13-trans prostenoic acid |
| 6 | 1-trans-tri-n-butylstannyl-4-trifluoromethyl-4-trimethylsiloxy-1-octene | 2-(5-carbotrimethylsiloxypentyl)-4-trimethylsiloxycyclopent-2-en-1-one | dl-11α,16-dihydroxy-9-oxo-16-trifluoromethyl-2-nor-13-trans prostenoic acid |
| 7 | 1-trans-tri-n-butylstannyl-4-fluoromethyl-4-trimethylsiloxy-1-nonene | 2-(5-carbotrimethylsiloxypentyl)-4-trimethylsiloxycyclopent-2-en-1-one | dl-11α,16-dihydroxy-9-oxo-16-fluoromethyl-20-methyl-2-nor-13-trans prostenoic acid |
| 8 | 1-trans-tri-n-butylstannyl-4-difluoromethyl-4-trimethylsiloxy-1-nonene | 2-(5-carbotrimethylsiloxypentyl)-4-trimethylsiloxycyclopent-2-en-1-one | dl-11α,16-dihydroxy-9-oxo-16-difluoromethyl-20-methyl-2-nor-13-trans prostenoic acid |
| 9 | 1-trans-tri-n-butylstannyl-4-trifluoromethyl-4-trimethylsiloxy-1-nonene | 2-(5-carbotrimethylsiloxypentyl)-4-trimethylsiloxycyclopent-2-en-1-one | dl-11α,16-dihydroxy-9-oxo-16-trifluoromethyl-20-methyl-2-nor-13-trans prostenoic acid |
| 10 | 1-trans-tri-n-butylstannyl-4-fluoromethyl-4-trimethylsiloxy-1-decene | 2-(5-carbotrimethylsiloxypentyl)-4-trimethylsiloxycyclopent-2-en-1-one | dl-11α,16-dihydroxy-9-oxo-16-fluoromethyl-20-ethyl-2-nor-13-trans prostenoic acid |
| 11 | 1-trans-tri-n-butylstannyl-4-difluoromethyl-4-trimethylsiloxy-1-decene | 2-(5-carbotrimethylsiloxypentyl)-4-trimethylsiloxycyclopent-2-en-1-one | dl-11α,16-dihydroxy-9-oxo-16-difluoromethyl-20-ethyl-2-nor-13-trans prostenoic acid |
| 12 | 1-trans-tri-n-butylstannyl-4-trifluoromethyl-4-trimethylsiloxy-1-decene | 2-(5-carbotrimethylsiloxypentyl)-4-trimethylsiloxycyclopent-2-en-1-one | dl-11α,16-dihydroxy-9-oxo-16-trifluoromethyl-20-ethyl-2-nor-13-trans prostenoic acid |
| 13 | 1-trans-tri-n-butylstannyl-4-fluoromethyl-4-trimethylsiloxy-1-heptene | 2-(6-carbotrimethylsiloxyhexyl)-4-trimethylsiloxycyclopent-2-en-1-one | dl-11α,16-dihydroxy-9-oxo-16-fluoromethyl-20-nor-13-trans prostenoic acid |
| 14 | 1-trans-tri-n-butylstannyl-4-difluoromethyl-4-trimethylsiloxy-1-heptene | 2-(6-carbotrimethylsiloxyhexyl)-4-trimethylsiloxycyclopent-2-en-1-one | dl-11α,16-dihydroxy-9-oxo-16-difluoromethyl-20-nor-13-trans prostenoic acid |
| 15 | 1-trans-tri-n-butylstannyl-4-trifluoromethyl-4-trimethylsiloxy-1-heptene | 2-(6-carbotrimethylsiloxyhexyl)-4-trimethylsiloxycyclopent-2-en-1-one | dl-11α,16-dihydroxy-9-oxo-16-trifluoromethyl-20-nor-13-trans prostenoic acid |
| 16 | 1-trans-tri-n-butylstannyl-4-fluoromethyl-4-trimethylsiloxy-1-octene | 2-(6-carbotrimethylsiloxyhexyl)-4-trimethylsiloxycyclopent-2-en-1-one | dl-11α,16-dihydroxy-9-oxo-16-fluoromethyl-13-trans prostenoic acid |
| 17 | 1-trans-tri-n-butylstannyl-4-difluoromethyl-4-trimethylsiloxy-1-octene | 2-(6-carbotrimethylsiloxyhexyl)-4-trimethylsiloxycyclopent-2-en-1-one | dl-11α,16-dihydroxy-9-oxo-16-difluoromethyl-13-trans prostenoic acid |
| 18 | 1-trans-tri-n-butylstannyl-4-trifluoromethyl-4-trimethylsiloxy-1-octene | 2-(6-carbotrimethylsiloxyhexyl)-4-trimethylsiloxycyclopent-2-en-1-one | dl-11α,16-dihydroxy-9-oxo-16-trifluoromethyl-13-trans prostenoic acid |
| 19 | 1-trans-tri-n-butylstannyl-4-fluoromethyl-4-trimethylsiloxy-1-nonene | 2-(6-carbotrimethylsiloxyhexyl)-4-trimethylsiloxycyclopent-2-en-1-one | dl-11α,16-dihydroxy-9-oxo-16-fluoromethyl-20-methyl-13-trans prostenoic acid |
| 20 | 1-trans-tri-n-butylstannyl-4-difluoromethyl-4-trimethylsiloxy-1-nonene | 2-(6-carbotrimethylsiloxyhexyl)-4-trimethylsiloxycyclopent-2-en-1-one | dl-11α,16-dihydroxy-9-oxo-16-difluoromethyl-20-methyl-13-trans prostenoic acid |
| 21 | 1-trans-tri-n-butylstannyl-4-trifluoromethyl-4-trimethylsiloxy-1-nonene | 2-(6-carbotrimethylsiloxyhexyl)-4-trimethylsiloxycyclopent-2-en-1-one | dl-11α,16-dihydroxy-9-oxo-16-trifluoromethyl-20-methyl-13-trans prostenoic acid |
| 22 | 1-trans-tri-n-butylstannyl-4-fluoromethyl-4-trimethylsiloxy-1-decene | 2-(6-carbotrimethylsiloxyhexyl)-4-trimethylsiloxycyclopent-2-en-1-one | dl-11α,16-dihydroxy-9-oxo-16-fluoromethyl-20-ethyl-13-trans prostenoic acid |
| 23 | 1-trans-tri-n-butylstannyl-4-difluoromethyl-4-trimethylsiloxy-1-decene | 2-(6-carbotrimethylsiloxyhexyl)-4-trimethylsiloxycyclopent-2-en-1-one | dl-11α,16-dihydroxy-9-oxo-16-difluoromethyl-20-ethyl-13-trans prostenoic acid |
| 24 | 1-trans-tri-n-butylstannyl-4-trifluoromethyl-4-trimethylsiloxy-1-decene | 2-(6-carbotrimethylsiloxyhexyl)-4-trimethylsiloxycyclopent-2-en-1-one | dl-11α,16-dihydroxy-9-oxo-16-trifluoromethyl-20-ethyl-13-trans prostenoic acid |
| 25 | 1-trans-tri-n-butylstannyl-4-fluoromethyl-4-trimethylsiloxy-1-heptene | 2-(7-carbotrimethylsiloxyheptyl)-4-trimethylsiloxycyclopent-2-en-1-one | dl-11α,16-dihydroxy-9-oxo-16-fluoromethyl-20-nor-2-homo-13-trans prostenoic acid |
| 26 | 1-trans-tri-n-butylstannyl-4-difluoromethyl-4-trimethylsiloxy-1-heptene | 2-(7-carbotrimethylsiloxyheptyl)-4-trimethylsiloxycyclopent-2-en-1-one | dl-11α,16-dihydroxy-9-oxo-16-difluoromethyl-20-nor-2-homo-13-trans prostenoic acid |

| | -continued | |
|---|---|---|
| 27 | 1-trans-tri-n-butylstannyl-4-trifluoromethyl-4-trimethylsiloxy-1-heptene | 2-(7-carbotrimethylsiloxycyclopent-2-en-1-one | dl-11α,16-dihydroxy-9-oxo-16-trifluoromethyl-20-nor-2-homo-13-trans prostenoic acid |
| 28 | 1-trans-tri-n-butylstannyl-4-fluoromethyl-4-trimethylsiloxy-1-heptene | 2-(7-carbotrimethylsiloxycyclopent-2-en-1-one | dl-11α,16-dihydroxy-9-oxo-16-fluoromethyl-2-homo-13-trans prostenoic acid |
| 29 | 1-trans-tri-n-butylstannyl-4-difluoromethyl-4-trimethylsiloxy-1-octene | 2-(7-carbotrimethylsiloxycyclopent-2-en-1-one | dl-11α,16-dihydroxy-9-oxo-16-difluoromethyl-2-homo-13-trans prostenoic acid |
| 30 | 1-trans-tri-n-butylstannyl-4-trifluoromethyl-4-trimethylsiloxy-1-octene | 2-(7-carbotrimethylsiloxycyclopent-2-en-1-one | dl-11α,16-dihydroxy-9-oxo-16-trifluoromethyl-2-homo-13-trans prostenoic acid |
| 31 | 1-trans-tri-n-butylstannyl-4-fluoromethyl-4-trimethylsiloxy-1-octene | 2-(7-carbotrimethylsiloxycyclopent-2-en-1-one | dl-11α,16-dihydroxy-9-oxo-16-fluoromethyl-13-trans prostenoic acid |
| 32 | 1-trans-tri-n-butylstannyl-4-difluoromethyl-4-trimethylsiloxy-1-nonene | 2-(7-carbotrimethylsiloxycyclopent-2-en-1-one | dl-11α,16-dihydroxy-9-oxo-16-difluoromethyl-20-methyl-2-homo-13-trans prostenoic acid |
| 33 | 1-trans-tri-n-butylstannyl-4-trifluoromethyl-4-trimethylsiloxy-1-nonene | 2-(7-carbotrimethylsiloxycyclopent-2-en-1-one | dl-11α,16-dihydroxy-9-oxo-16-trifluoromethyl-20-methyl-2-homo-13-trans prostenoic acid |
| 34 | 1-trans-tri-n-butylstannyl-4-fluoromethyl-4-trimethylsiloxy-1-nonene | 2-(7-carbotrimethylsiloxycyclopent-2-en-1-one | dl-11α,16-dihydroxy-9-oxo-16-fluoromethyl-20-methyl-2-homo-13-trans prostenoic acid |
| 35 | 1-trans-tri-n-butylstannyl-4-difluoromethyl-4-trimethylsiloxy-1-decene | 2-(7-carbotrimethylsiloxycyclopent-2-en-1-one | dl-11α,16-dihydroxy-9-oxo-16-difluoromethyl-20-ethyl-2-homo-13-trans prostenoic acid |
| 36 | 1-trans-tri-n-butylstannyl-4-trifluoromethyl-4-trimethylsiloxy-1-decene | 2-(7-carbotrimethylsiloxycyclopent-2-en-1-one | dl-11α,16-dihydroxy-9-oxo-16-trifluoromethyl-20-ethyl-2-homo-13-trans prostenoic acid |
| 37 | 1-trans-tri-n-butylstannyl-4-fluoromethyl-4-trimethylsiloxy-1-heptene | 2-(6-carbotrimethylsiloxyhexyl)-4R-trimethylsiloxycyclopent-2-en-1-one | nat-11α,16-dihydroxy-9-oxo-16-fluoromethyl-20-nor-13-trans prostenoic acid |
| 38 | 1-trans-tri-n-butylstannyl-4-difluoromethyl-4-trimethylsiloxy-1-heptene | 2-(6-carbotrimethylsiloxyhexyl)-4R-trimethylsiloxycyclopent-2-en-1-one | nat-11α,16-dihydroxy-9-oxo-16-difluoromethyl-20-nor-13-trans prostenoic acid |
| 39 | 1-trans-tri-n-butylstannyl-4-trifluoromethyl-4-trimethylsiloxy-1-heptene | 2-(6-carbotrimethylsiloxyhexyl)-4R-trimethylsiloxycyclopent-2-en-1-one | nat-11α,16-dihydroxy-9-oxo-16-trifluoromethyl-20-nor-13-trans prostenoic acid |
| 40 | 1-trans-tri-n-butylstannyl-4-fluoromethyl-4-trimethylsiloxy-1-octene | 2-(6-carbotrimethylsiloxyhexyl)-4R-trimethylsiloxycyclopent-2-en-1-one | nat-11α,16-dihydroxy-9-oxo-16-fluoromethyl-13-trans prostenoic acid |
| 41 | 1-trans-tri-n-butylstannyl-4-difluoromethyl-4-trimethylsiloxy-1-octene | 2-(6-carbotrimethylsiloxyhexyl)-4R-trimethylsiloxycyclopent-2-en-1-one | nat-11α,16-dihydroxy-9-oxo-16-difluoromethyl-13-trans prostenoic acid |
| 42 | 1-trans-tri-n-butylstannyl-4-trifluoromethyl-4-trimethylsiloxy-1-octene | 2-(6-carbotrimethylsiloxyhexyl)-4R-trimethylsiloxycyclopent-2-en-1-one | nat-11α,16-dihydroxy-9-oxo-16-trifluoromethyl-13-trans prostenoic acid |
| 43 | 1-trans-tri-n-butylstannyl-4-fluoromethyl-4-trimethylsiloxy-1-nonene | 2-(6-carbotrimethylsiloxyhexyl)-4R-trimethylsiloxycyclopent-2-en-1-one | nat-11α,16-dihydroxy-9-oxo-16-fluoromethyl-20-methyl-13-trans prostenoic acid |
| 44 | 1-trans-tri-n-butylstannyl-4-difluoromethyl-4-trimethylsiloxy-1-nonene | 2-(6-carbotrimethylsiloxyhexyl)-4R-trimethylsiloxycyclopent-2-en-1-one | nat-11α,16-dihydroxy-9-oxo-16-difluoromethyl-20-methyl-13-trans prostenoic acid |
| 45 | 1-trans-tri-n-butylstannyl-4-trifluoromethyl-4-trimethylsiloxy-1-nonene | 2-(6-carbotrimethylsiloxyhexyl)-4R-trimethylsiloxycyclopent-2-en-1-one | nat-11α,16-dihydroxy-9-oxo-16-trifluoromethyl-20-methyl-13-trans prostenoic acid |
| 46 | 1-trans-tri-n-butylstannyl-4-fluoromethyl-4-trimethylsiloxy-1-decene | 2-(6-carbotrimethylsiloxyhexyl)-4R-trimethylsiloxycyclopent-2-en-1-one | nat-11α,16-dihydroxy-9-oxo-16-fluoromethyl-20-ethyl-13-trans prostenoic acid |
| 47 | 1-trans-tri-n-butylstannyl-4-difluoromethyl-4-trimethylsiloxy-1-decene | 2-(6-carbotrimethylsiloxyhexyl)-4R-trimethylsiloxycyclopent-2-en-1-one | nat-11α,16-dihydroxy-9-oxo-16-difluoromethyl-20-ethyl-13-trans prostenoic acid |
| 48 | 1-trans-tri-n-butylstannyl-4-trifluoromethyl-4-trimethylsiloxy-1-decene | 2-(6-carbotrimethylsiloxyhexyl)-4R-trimethylsiloxycyclopent-2-en-1-one | nat-11α,16-dihydroxy-9-oxo-16-trifluoromethyl-20-ethyl-13-trans prostenoic acid |
| 49 | 1-trans-tri-n-butylstannyl-4-fluoromethyl-4-trimethylsiloxy-1-heptene | 2-(5-carboethoxypentyl)cyclopent-2-en-1-one | dl-16-hydroxy-9-oxo-16-fluoromethyl-20-nor-2-nor-13-trans prostenoic acid |
| 50 | 1-trans-tri-n-butylstannyl-4-difluoromethyl-4-trimethylsiloxy-1-heptene | 2-(5-carboethoxypentyl)cyclopent-2-en-1-one | dl-16-hydroxy-9-oxo-16-difluoromethyl-20-nor-2-nor-13-trans prostenoic acid |
| 51 | 1-trans-tri-n-butylstannyl-4-trifluoromethyl-4-trimethylsiloxy-1-heptene | 2-(5-carboethoxypentyl)cyclopent-2-en-1-one | dl-16-hydroxy-9-oxo-16-trifluoromethyl-20-nor-2-nor-13-trans prostenoic acid |
| 52 | 1-trans-tri-n-butylstannyl-4-fluoromethyl-4-trimethylsiloxy-1-octene | 2-(5-carboethoxypentyl)cyclopent-2-en-1-one | dl-16-hydroxy-9-oxo-16-fluoromethyl- |

| | | | |
|---|---|---|---|
| 53 | 4-trimethylsilyloxy-1-octene | 2-(5-carboethoxypentyl)cyclopent-2-en-1-one | 2-nor-13-trans prostenoic acid |
| | 1-trans-tri-n-butylstannyl-4-difluoromethyl-4-trimethylsilyloxy-1-octene | 2-(5-carboethoxypentyl)cyclopent-2-en-1-one | dl-16-hydroxy-9-oxo-16-difluoromethyl-2-nor-13-trans prostenoic acid |
| 54 | 1-trans-tri-n-butylstannyl-4-trifluoromethyl-4-trimethylsilyloxy-1-octene | 2-(5-carboethoxypentyl)cyclopent-2-en-1-one | dl-16-hydroxy-9-oxo-16-trifluoromethyl-2-nor-13-trans prostenoic acid |
| 55 | 1-trans-tri-n-butylstannyl-4-fluoromethyl-4-trimethylsilyloxy-1-nonene | 2-(5-carboethoxypentyl)cyclopent-2-en-1-one | dl-16-hydroxy-9-oxo-16-fluoromethyl-20-methyl-2-nor-13-trans prostenoic acid |
| 56 | 1-trans-tri-n-butylstannyl-4-difluoromethyl-4-trimethylsilyloxy-1-nonene | 2-(5-carboethoxypentyl)cyclopent-2-en-1-one | dl-16-hydroxy-9-oxo-16-difluoromethyl-20-methyl-2-nor-13-trans prostenoic acid |
| 57 | 1-trans-tri-n-butylstannyl-4-trifluoromethyl-4-trimethylsilyloxy-1-nonene | 2-(5-carboethoxypentyl)cyclopent-2-en-1-one | dl-16-hydroxy-9-oxo-16-trifluoromethyl-20-methyl-2-nor-13-trans prostenoic acid |
| 58 | 1-trans-tri-n-butylstannyl-4-fluoromethyl-4-trimethylsilyloxy-1-decene | 2-(5-carboethoxypentyl)cyclopent-2-en-1-one | dl-16-hydroxy-9-oxo-16-fluoromethyl-20-ethyl-2-nor-13-trans prostenoic acid |
| 59 | 1-trans-tri-n-butylstannyl-4-difluoromethyl-4-trimethylsilyloxy-1-decene | 2-(5-carboethoxypentyl)cyclopent-2-en-1-one | dl-16-hydroxy-9-oxo-16-difluoromethyl-20-ethyl-2-nor-13-trans prostenoic acid |
| 60 | 1-trans-tri-n-butylstannyl-4-trifluoromethyl-4-trimethylsilyloxy-1-decene | 2-(5-carboethoxypentyl)cyclopent-2-en-1-one | dl-16-hydroxy-9-oxo-16-trifluoromethyl-20-ethyl-2-nor-13-trans prostenoic acid |
| 61 | 1-trans-tri-n-butylstannyl-4-fluoromethyl-4-trimethylsilyloxy-1-heptene | 2-(6-carboethoxyhexyl)cyclopent-2-en-1-one | dl-16-hydroxy-9-oxo-16-fluoromethyl-20-nor-13-trans prostenoic acid |
| 62 | 1-trans-tri-n-butylstannyl-4-difluoromethyl-4-trimethylsilyloxy-1-heptene | 2-(6-carboethoxyhexyl)cyclopent-2-en-1-one | dl-16-hydroxy-9-oxo-16-difluoromethyl-20-nor-13-trans prostenoic acid |
| 63 | 1-trans-tri-n-butylstannyl-4-trifluoromethyl-4-trimethylsilyloxy-1-heptene | 2-(6-carboethoxyhexyl)cyclopent-2-en-1-one | 20-nor-13-trans prostenoic acid |
| 64 | 1-trans-tri-n-butylstannyl-4-fluoromethyl-4-trimethylsilyloxy-1-decene | 2-(6-carboethoxyhexyl)cyclopent-2-en-1-one | dl-16-hydroxy-9-oxo-16-fluoromethyl-13-trans prostenoic acid |
| 65 | 1-trans-tri-n-butylstannyl-4-difluoromethyl-4-trimethylsilyloxy-1-octene | 2-(6-carboethoxyhexyl)cyclopent-2-en-1-one | dl-16-hydroxy-9-oxo-16-difluoromethyl-13-trans prostenoic acid |
| 66 | 1-trans-tri-n-butylstannyl-4-trifluoromethyl-4-trimethylsilyloxy-1-octene | 2-(6-carboethoxyhexyl)cyclopent-2-en-1-one | dl-16-hydroxy-9-oxo-16-trifluoromethyl-13-trans prostenoic acid |
| 67 | 1-trans-tri-n-butylstannyl-4-fluoromethyl-4-trimethylsilyloxy-1-nonene | 2-(6-carboethoxyhexyl)cyclopent-2-en-1-one | dl-16-hydroxy-9-oxo-16-fluoromethyl-20-methyl-13-trans prostenoic acid |
| 68 | 1-trans-tri-n-butylstannyl-4-difluoromethyl-4-trimethylsilyloxy-1-nonene | 2-(6-carboethoxyhexyl)cyclopent-2-en-1-one | dl-16-hydroxy-9-oxo-16-difluoromethyl-20-methyl-13-trans prostenoic acid |
| 69 | 1-trans-tri-n-butylstannyl-4-trifluoromethyl-4-trimethylsilyloxy-1-nonene | 2-(6-carboethoxyhexyl)cyclopent-2-en-1-one | dl-16-hydroxy-9-oxo-16-trifluoromethyl-20-methyl-13-trans prostenoic acid |
| 70 | 1-trans-tri-n-butylstannyl-4-fluoromethyl-4-trimethylsilyloxy-1-decene | 2-(6-carboethoxyhexyl)cyclopent-2-en-1-one | dl-16-hydroxy-9-oxo-16-fluoromethyl-20-ethyl-13-trans prostenoic acid |
| 71 | 1-trans-tri-n-butylstannyl-4-difluoromethyl-4-trimethylsilyloxy-1-decene | 2-(6-carboethoxyhexyl)cyclopent-2-en-1-one | dl-16-hydroxy-9-oxo-16-difluoromethyl-20-ethyl-13-trans prostenoic acid |
| 72 | 1-trans-tri-n-butylstannyl-4-trifluoromethyl-4-trimethylsilyloxy-1-decene | 2-(6-carboethoxyhexyl)cyclopent-2-en-1-one | dl-16-hydroxy-9-oxo-16-trifluoromethyl-20-ethyl-13-trans prostenoic acid |
| 73 | 1-trans-tri-n-butylstannyl-4-fluoromethyl-4-trimethylsilyloxy-1-heptene | 2-(7-carboethoxyheptyl)cyclopent-2-en-1-one | dl-16-hydroxy-9-oxo-16-fluoromethyl-20-nor-2-homo-13-trans prostenoic acid |
| 74 | 1-trans-tri-n-butylstannyl-4-difluoromethyl-4-trimethylsilyloxy-1-heptene | 2-(7-carboethoxyheptyl)cyclopent-2-en-1-one | dl-16-hydroxy-9-oxo-16-difluoromethyl-20-nor-2-homo-13-trans prostenoic acid |
| 75 | 1-trans-tri-n-butylstannyl-4-trifluoromethyl-4-trimethylsilyloxy-1-heptene | 2-(7-carboethoxyheptyl)cyclopent-2-en-1-one | dl-16-hydroxy-9-oxo-16-trifluoromethyl-20-nor-2-homo-13-trans prostenoic acid |
| 76 | 1-trans-tri-n-butylstannyl-4-fluoromethyl-4-trimethylsilyloxy-1-octene | 2-(7-carboethoxyheptyl)cyclopent-2-en-1-one | dl-16-hydroxy-9-oxo-16-fluoromethyl-2-homo-13-trans prostenoic acid |
| 77 | 1-trans-tri-n-butylstannyl-4-difluoromethyl-4-trimethylsilyloxy-1-octene | 2-(7-carboethoxyheptyl)cyclopent-2-en-1-one | dl-16-hydroxy-9-oxo-16-difluoromethyl-2-homo-13-trans prostenoic acid |
| 78 | 1-trans-tri-n-butylstannyl-4-trifluoromethyl-4-trimethylsilyloxy-1-octene | 2-(7-carboethoxyheptyl)cyclopent-2-en-1-one | dl-16-hydroxy-9-oxo-16-trifluoromethyl-2-homo-13-trans prostenoic acid |

| | -continued | |
|---|---|---|
| 79 | 1-trans-tri-n-butylstannyl-4-fluoromethyl-4-trimethylsiloxy-1-nonene | 2-(7-carboethoxyheptyl)cyclopent-2-en-1-one | dl-16-hydroxy-9-oxo-16-fluoromethyl-20-methyl-2-homo-13-trans prostenoic acid |
| 80 | 1-trans-tri-n-butylstannyl-4-difluoromethyl-4-trimethylsiloxy-1-nonene | 2-(7-carboethoxyheptyl)cyclopent-2-en-1-one | dl-16-hydroxy-9-oxo-16-difluoromethyl-20-methyl-2-homo-13-trans prostenoic acid |
| 81 | 1-trans-tri-n-butylstannyl-4-trifluoromethyl-4-trimethylsiloxy-1-nonene | 2-(7-carboethoxyheptyl)cyclopent-2-en-1-one | dl-16-hydroxy-9-oxo-16-trifluoromethyl-20-methyl-2-homo-13-trans prostenoic acid |
| 82 | 1-trans-tri-n-butylstannyl-4-fluoromethyl-4-trimethylsiloxy-1-decene | 2-(7-carboethoxyheptyl)cyclopent-2-en-1-one | dl-16-hydroxy-9-oxo-16-fluoromethyl-20-ethyl-2-homo-13-trans prostenoic acid |
| 83 | 1-trans-tri-n-butylstannyl-4-difluoromethyl-4-trimethylsiloxy-1-decene | 2-(7-carboethoxyheptyl)cyclopent-2-en-1-one | dl-16-hydroxy-9-oxo-16-difluoromethyl-20-ethyl-2-homo-13-trans prostenoic acid |
| 84 | 1-trans-tri-n-butylstannyl-4-trifluoromethyl-4-trimethylsiloxy-1-decene | 2-(7-carboethoxyheptyl)cyclopent-2-en-1-one | dl-16-hydroxy-9-oxo-16-trifluoromethyl-20-ethyl-2-homo-13-trans prostenoic acid |

TABLE I (Continued)

Treatment of the PGE$_1$ derivatives of Examples 1 to 84 of Table I with lithium perhydro-9b-boraphenalyl hydride by the procedure of Reference Example 20 is productive of the PGF$_{1\alpha}$ derivatives of Examples 85 to 252 of Table I.

| EXAMPLE | STARTING PROSTAGLANDIN OF THE PGE SERIES | PRODUCT PROSTAGLANDIN OF THE PGF$_{1\alpha}$ SERIES |
|---|---|---|
| 85 | dl-11α,16-dihydroxy-9-oxo-16-fluoromethyl-20-nor-2-nor-13-trans prostenoic acid | dl-9α,11α,16-trihydroxy-16-fluoromethyl-20-nor-2-nor-13-trans prostenoic acid |
| 86 | dl-11α,16-dihydroxy-9-oxo-16-difluoromethyl-20-nor-2-nor-13-trans prostenoic acid | dl-9α,11α,16-trihydroxy-16-difluoromethyl-20-nor-2-nor-13-trans prostenoic acid |
| 87 | dl-11,16-dihydroxy-9-oxo-16-trifluoromethyl-20-nor-2-nor-13-trans prostenoic acid | dl-9α,11α,16-trihydroxy-16-trifluoromethyl-20-nor-2-nor-13-trans prostenoic acid |
| 88 | dl-11α,16-dihydroxy-9-oxo-16-fluoromethyl-2-nor-13-trans prostenoic acid | dl-9α,11α,16-trihydroxy-16-fluoromethyl-2-nor-13-trans prostenoic acid |
| 89 | dl-11α,16-dihydroxy-9-oxo-16-difluoromethyl-2-nor-13-trans prostenoic acid | dl-9α,11α,16-trihydroxy-16-difluoromethyl-2-nor-13-trans prostenoic acid |
| 90 | dl-11α,16-dihydroxy-9-oxo-16-trifluoromethyl-2-nor-13-trans prostenoic acid | dl-9α,11α,16-trihydroxy-16-trifluoromethyl-2-nor-13-trans prostenoic acid |
| 91 | dl-11α,16-dihydroxy-9-oxo-16-fluoromethyl-20-methyl-2-nor-13-trans prostenoic acid | dl-9α,11α,16-trihydroxy-16-fluoromethyl-20-methyl-2-nor-13-trans prostenoic acid |
| 92 | dl-11α,16-dihydroxy-9-oxo-16-difluoromethyl-20-methyl-2-nor-13-trans prostenoic acid | dl-9α,11α,16-trihydroxy-16-difluoromethyl-20-methyl-2-nor-13-trans prostenoic acid |
| 93 | dl-11α,16-dihydroxy-9-oxo-16-trifluoromethyl-20-methyl-2-nor-13-trans prostenoic acid | dl-9α,11α,16-trihydroxy-16-trifluoromethyl-20-methyl-2-nor-13-trans prostenoic acid |
| 94 | dl-11α,16-dihydroxy-9-oxo-16-fluoromethyl-20-ethyl-2-nor-13-trans prostenoic acid | dl-9α,11α,16-trihydroxy-16-fluoromethyl-20-ethyl-2-nor-13-trans prostenoic acid |
| 95 | dl-11α,16-dihydroxy-9-oxo-16-difluoromethyl-20-ethyl-2-nor-13-trans prostenoic acid | dl-9α,11α,16-trihydroxy-16-difluoromethyl-20-ethyl-2-nor-13-trans prostenoic acid |
| 96 | dl-11α,16-dihydroxy-9-oxo-16-trifluoromethyl-20-ethyl-2-nor-13-trans prostenoic acid | dl-9α,11α,16-trihydroxy-16-trifluoromethyl-20-ethyl-2-nor-13-trans prostenoic acid |
| 97 | dl-11α,16-dihydroxy-9-oxo-16-fluoromethyl-20-nor-13-trans prostenoic acid | dl-9α,11α,16-trihydroxy-16-fluoromethyl-20-nor-13-trans prostenoic acid |
| 98 | dl-11α,16-dihydroxy-9-oxo-16-difluoromethyl-20-nor-13-trans prostenoic acid | dl-9α,11α,16-trihydroxy-16-difluoromethyl-20-nor-13-trans prostenoic acid |
| 99 | dl-11α,16-dihydroxy-9-oxo-16-trifluoromethyl-20-nor-13-trans prostenoic acid | dl-9α,11α,16-trihydroxy-16-trifluoromethyl-20-nor-13-trans prostenoic acid |
| 100 | dl-11α,16-dihydroxy-9-oxo-16-fluoromethyl-13-trans prostenoic acid | dl-9α,11α,16-trihydroxy-16-fluoromethyl-13-trans prostenoic acid |
| 101 | dl-11α,16-dihydroxy-9-oxo-16-difluoromethyl-13-trans prostenoic acid | dl-9α,11α,16-trihydroxy-16-difluoromethyl-13-trans prostenoic acid |
| 102 | dl-11α,16-dihydroxy-9-oxo-16-trifluoromethyl-13-trans prostenoic acid | dl-9α,11α,16-trihydroxy-16-trifluoromethyl-13-trans prostenoic acid |
| 103 | dl-11α,16-dihydroxy-9-oxo-16-fluoromethyl-20-methyl-13-trans prostenoic acid | dl-9α,11α,16-trihydroxy-16-fluoromethyl-20-methyl-13-trans prostenoic acid |
| 104 | dl-11α,16-dihydroxy-9-oxo-16-difluoromethyl-20-methyl-13-trans prostenoic acid | dl-9α,11α,16-trihydroxy-16-difluoromethyl-20-methyl-13-trans prostenoic acid |
| 105 | dl-11α,16-dihydroxy-9-oxo-16-trifluoromethyl-20-methyl-13-trans prostenoic acid | dl-9α,11α,16-trihydroxy-16-trifluoromethyl-20-methyl-13-trans prostenoic acid |
| 106 | dl-11α,16-dihydroxy-9-oxo-16-fluoromethyl-20-ethyl-13-trans prostenoic acid | dl-9α,11α,16-trihydroxy-16-fluoromethyl-20-ethyl-13-trans prostenoic acid |
| 107 | dl-11α,16-dihydroxy-9-oxo-16-difluoromethyl-20-ethyl-13-trans prostenoic acid | dl-9α,11α,16-trihydroxy-16-difluoromethyl-20-ethyl-13-trans prostenoic acid |
| 108 | dl-11α,16-dihydroxy-9-oxo-16-trifluoromethyl-20-ethyl-13-trans prostenoic acid | dl-9α,11α,16-trihydroxy-16-trifluoromethyl-20-ethyl-13-trans prostenoic acid |
| 109 | dl-11α,16-dihydroxy-9-oxo-16-fluoromethyl-20-nor-2-homo-13-trans prostenoic acid | dl-9α,11α,16-trihydroxy-16-fluoromethyl-20-nor-2-homo-13-trans prostenoic acid |
| 110 | dl-11α,16-dihydroxy-9-oxo-16-difluoromethyl-20-nor-2-homo-13-trans prostenoic acid | dl-9α,11α,16-trihydroxy-16-difluoromethyl-20-nor-2-homo-13-trans prostenoic acid |
| 111 | dl-11α,16-dihydroxy-9-oxo-16-trifluoromethyl-20-nor-2-homo-13-trans prostenoic acid | dl-9α,11α,16-trihydroxy-16-trifluoromethyl-20-nor-2-homo-13-trans prostenoic acid |
| 112 | dl-11α,16-dihydroxy-9-oxo-16-fluoromethyl-2-homo-13-trans prostenoic acid | dl-9α,11α,16-trihydroxy-16-fluoromethyl-2-homo-13-trans prostenoic acid |
| 113 | dl-11α,16-dihydroxy-9-oxo-16-difluoromethyl-2-homo-13-trans prostenoic acid | dl-9α,11α,16-trihydroxy-16-difluoromethyl-2-homo-13-trans prostenoic acid |
| 114 | dl-11α,16-dihydroxy-9-oxo-16-trifluoromethyl-2-homo-13-trans prostenoic acid | dl-9α,11α,16-trihydroxy-16-trifluoromethyl-2-homo-13-trans prostenoic acid |
| 115 | dl-11α,16-dihydroxy-9-oxo-16-fluoromethyl-20-methyl-2-homo-13-trans prostenoic acid | dl-9α,11α,16-trihydroxy-16-fluoromethyl-20-methyl-2-homo-13-trans prostenoic acid |
| 116 | dl-11α,16-dihydroxy-9-oxo-16-difluoromethyl-20-methyl-2-homo-13-trans prostenoic acid | dl-9α,11α,16-trihydroxy-16-difluoromethyl-20-methyl-2-homo-13-trans prostenoic acid |
| 117 | dl-11α,16-dihydroxy-9-oxo-16-trifluoromethyl-20-methyl-2-homo-13-trans prostenoic acid | dl-9α,11α,16-trihydroxy-16-trifluoromethyl-20-methyl-2-homo-13-trans prostenoic acid |
| 118 | dl-11α,16-dihydroxy-9-oxo-16-fluoromethyl-20-ethyl-2-homo-13-trans prostenoic acid | dl-9α,11α,16-trihydroxy-16-fluoromethyl-20-ethyl-2-homo-13-trans prostenoic acid |
| 119 | dl-11α,16-dihydroxy-9-oxo-16-difluoromethyl-20-ethyl-2-homo-13-trans prostenoic acid | dl-9α,11α,16-trihydroxy-16-difluoromethyl-20-ethyl-2-homo-13-trans prostenoic acid |
| 120 | dl-11α,16-dihydroxy-9-oxo-16-trifluoromethyl-20-ethyl-2-homo-13-trans prostenoic acid | dl-9α,11α,16-trihydroxy-16-trifluoromethyl-20-ethyl-2-homo-13-trans prostenoic acid |
| 121 | nat-11α,16-dihydroxy-9-oxo-16-fluoromethyl-20-nor-13-trans prostenoic acid | nat-9α,11α,16-trihydroxy-16-fluoromethyl-20-nor-13-trans prostenoic acid |
| 122 | nat-11α,16-dihydroxy-9-oxo-16-difluoromethyl- | nat-9α,11α,16-trihydroxy-16-difluoromethyl- |

| | | |
|---|---|---|
| 123 | nat-11α,16-dihydroxy-9-oxo-16-trifluoromethyl-20-nor-13-trans prostenoic acid | nat-9α,11α,16-trihydroxy-16-trifluoromethyl-20-nor-13-trans prostenoic acid |
| 124 | nat-11α,16-dihydroxy-9-oxo-16-fluoromethyl-13-trans prostenoic acid | nat-9α,11α,16-trihydroxy-16-fluoromethyl-13-trans prostenoic acid |
| 125 | nat-11α,16-dihydroxy-9-oxo-16-difluoromethyl-13-trans prostenoic acid | nat-9α,11α,16-trihydroxy-16-difluoromethyl-13-trans prostenoic acid |
| 126 | nat-11α,16-dihydroxy-9-oxo-16-trifluoromethyl-13-trans prostenoic acid | nat-9α,11α,16-trihydroxy-16-trifluoromethyl-13-trans prostenoic acid |
| 127 | nat-11α,16-dihydroxy-9-oxo-16-fluoromethyl-20-methyl-13-trans prostenoic acid | nat-9α,11α,16-trihydroxy-16-fluoromethyl-20-methyl-13-trans prostenoic acid |
| 128 | nat-11α,16-dihydroxy-9-oxo-16-difluoromethyl-20-methyl-13-trans prostenoic acid | nat-9α,11α,16-trihydroxy-16-difluoromethyl-20-methyl-13-trans prostenoic acid |
| 129 | nat-11α,16-dihydroxy-9-oxo-16-trifluoromethyl-20-methyl-13-trans prostenoic acid | nat-9α,11α,16-trihydroxy-16-trifluoromethyl-20-methyl-13-trans prostenoic acid |
| 130 | nat-11α,16-dihydroxy-9-oxo-16-fluoromethyl-20-ethyl-13-trans prostenoic acid | nat-9α,11α,16-trihydroxy-16-fluoromethyl-20-ethyl-13-trans prostenoic acid |
| 131 | nat-11α,16-dihydroxy-9-oxo-16-difluoromethyl-20-ethyl-13-trans prostenoic acid | nat-9α,11α,16-trihydroxy-16-difluoromethyl-20-ethyl-13-trans prostenoic acid |
| 132 | nat-11α,16-dihydroxy-9-oxo-16-trifluoromethyl-20-ethyl-13-trans prostenoic acid | nat-9α,11α,16-trihydroxy-16-trifluoromethyl-20-ethyl-13-trans prostenoic acid |
| 133 | dl-16-hydroxy-9-oxo-16-fluoromethyl-20-nor-2-nor-13-trans prostenoic acid | dl-9α,16-dihydroxy-16-fluoromethyl-20-nor-2-nor-13-trans prostenoic acid |
| 134 | dl-16-hydroxy-9-oxo-16-difluoromethyl-20-nor-2-nor-13-trans prostenoic acid | dl-9α,16-dihydroxy-16-difluoromethyl-20-nor-2-nor-13-trans prostenoic acid |
| 135 | dl-16-hydroxy-9-oxo-16-trifluoromethyl-20-nor-2-nor-13-trans prostenoic acid | dl-9α,16-dihydroxy-16-trifluoromethyl-20-nor-2-nor-13-trans prostenoic acid |
| 136 | dl-16-hydroxy-9-oxo-16-fluoromethyl-2-nor-13-trans prostenoic acid | dl-9α,16-dihydroxy-16-fluoromethyl-2-nor-13-trans prostenoic acid |
| 137 | dl-16-hydroxy-9-oxo-16-difluoromethyl-2-nor-13-trans prostenoic acid | dl-9α,16-dihydroxy-16-difluoromethyl-2-nor-13-trans prostenoic acid |
| 138 | dl-16-hydroxy-9-oxo-16-trifluoromethyl-2-nor-13-trans prostenoic acid | dl-9α,16-dihydroxy-16-trifluoromethyl-2-nor-13-trans prostenoic acid |
| 139 | dl-16-hydroxy-9-oxo-16-fluoromethyl-20-methyl-2-nor-13-trans prostenoic acid | dl-9α,16-dihydroxy-16-fluoromethyl-20-methyl-2-nor-13-trans prostenoic acid |
| 140 | dl-16-hydroxy-9-oxo-16-difluoromethyl-20-methyl-2-nor-13-trans prostenoic acid | dl-9α,16-dihydroxy-16-difluoromethyl-20-methyl-2-nor-13-trans prostenoic acid |
| 141 | dl-16-hydroxy-9-oxo-16-trifluoromethyl-20-methyl-2-nor-13-trans prostenoic acid | dl-9α,16-dihydroxy-16-trifluoromethyl-20-methyl-2-nor-13-trans prostenoic acid |
| 142 | dl-16-hydroxy-9-oxo-16-fluoromethyl-20-ethyl-2-nor-13-trans prostenoic acid | dl-9α,16-dihydroxy-16-fluoromethyl-20-ethyl-2-nor-13-trans prostenoic acid |
| 143 | dl-16-hydroxy-9-oxo-16-difluoromethyl-20-ethyl-2-nor-13-trans prostenoic acid | dl-9α,16-dihydroxy-16-difluoromethyl-20-ethyl-2-nor-13-trans prostenoic acid |
| 144 | dl-16-hydroxy-9-oxo-16-trifluoromethyl-20-ethyl-2-nor-13-trans prostenoic acid | dl-9α,16-dihydroxy-16-trifluoromethyl-20-ethyl-2-nor-13-trans prostenoic acid |
| 145 | dl-16-hydroxy-9-oxo-16-fluoromethyl-20-nor-13-trans prostenoic acid | dl-9α,16-dihydroxy-16-fluoromethyl-20-nor-13-trans prostenoic acid |
| 146 | dl-16-hydroxy-9-oxo-16-difluoromethyl-20-nor-13-trans prostenoic acid | dl-9α,16-dihydroxy-16-difluoromethyl-20-nor-13-trans prostenoic acid |
| 147 | dl-16-hydroxy-9-oxo-16-trifluoromethyl-20-nor-13-trans prostenoic acid | dl-9α,16-dihydroxy-16-trifluoromethyl-20-nor-13-trans prostenoic acid |
| 148 | dl-16-hydroxy-9-oxo-16-fluoromethyl-13-trans prostenoic acid | dl-9α,16-dihydroxy-16-fluoromethyl-13-trans prostenoic acid |
| 149 | dl-16-hydroxy-9-oxo-16-difluoromethyl-13-trans prostenoic acid | dl-9α,16-dihydroxy-16-difluoromethyl-13-trans prostenoic acid |
| 150 | dl-16-hydroxy-9-oxo-16-trifluoromethyl-13-trans prostenoic acid | dl-9α,16-dihydroxy-16-trifluoromethyl-13-trans prostenoic acid |
| 151 | dl-16-hydroxy-9-oxo-16-fluoromethyl-20-methyl-13-trans prostenoic acid | dl-9α,16-dihydroxy-16-fluoromethyl-20-methyl-13-trans prostenoic acid |
| 152 | dl-16-hydroxy-9-oxo-16-difluoromethyl-20-methyl-13-trans prostenoic acid | dl-9α,16-dihydroxy-16-difluoromethyl-20-methyl-13-trans prostenoic acid |
| 153 | dl-16-hydroxy-9-oxo-16-trifluoromethyl-20-methyl-13-trans prostenoic acid | dl-9α,16-dihydroxy-16-trifluoromethyl-20-methyl-13-trans prostenoic acid |
| 154 | dl-16-hydroxy-9-oxo-16-fluoromethyl-20-ethyl-13-trans prostenoic acid | dl-9α,16-dihydroxy-16-fluoromethyl-20-ethyl-13-trans prostenoic acid |
| 155 | dl-16-hydroxy-9-oxo-16-difluoromethyl-20-ethyl-13-trans prostenoic acid | dl-9α,16-dihydroxy-16-difluoromethyl-20-ethyl-13-trans prostenoic acid |
| 156 | dl-16-hydroxy-9-oxo-16-trifluoromethyl-20-ethyl-13-trans prostenoic acid | dl-9α,16-dihydroxy-16-trifluoromethyl-20-ethyl-13-trans prostenoic acid |
| 157 | dl-16-hydroxy-9-oxo-16-fluoromethyl-20-nor-2-homo-13-trans prostenoic acid | dl-9α,16-dihydroxy-16-fluoromethyl-20-nor-2-homo-13-trans prostenoic acid |
| 158 | dl-16-hydroxy-9-oxo-16-difluoromethyl-20-nor-2-homo-13-trans prostenoic acid | dl-9α,16-dihydroxy-16-difluoromethyl-20-nor-2-homo-13-trans prostenoic acid |
| 159 | dl-16-hydroxy-9-oxo-16-trifluoromethyl-20-nor-2-homo-13-trans prostenoic acid | dl-9α,16-dihydroxy-16-trifluoromethyl-20-nor-2-homo-13-trans prostenoic acid |
| 160 | dl-16-hydroxy-9-oxo-16-fluoromethyl-2-homo-13-trans prostenoic acid | dl-9α,16-dihydroxy-16-fluoromethyl-2-homo-13-trans prostenoic acid |
| 161 | dl-16-hydroxy-9-oxo-16-difluoromethyl-2-homo-13-trans prostenoic acid | dl-9α,16-dihydroxy-16-difluoromethyl-2-homo-13-trans prostenoic acid |

| | | |
|---|---|---|
| 162 | dl-16-hydroxy-9-oxo-16-trifluoromethyl-2-homo-13-trans prostenoic acid | dl-9α,16-dihydroxy-16-trifluoromethyl-2-homo-13-trans prostenoic acid |
| 163 | dl-16-hydroxy-9-oxo-16-fluoromethyl-20-methyl-2-homo-13-trans prostenoic acid | dl-9α,16-dihydroxy-16-fluoromethyl-20-methyl-2-homo-13-trans prostenoic acid |
| 164 | dl-16-hydroxy-9-oxo-16-difluoromethyl-20-methyl-2-homo-13-trans prostenoic acid | dl-9α,16-dihydroxy-16-difluoromethyl-20-methyl-2-homo-13-trans prostenoic acid |
| 165 | dl-16-hydroxy-9-oxo-16-trifluoromethyl-20-methyl-2-homo-13-trans prostenoic acid | dl-9α,16-dihydroxy-16-trifluoromethyl-20-methyl-2-homo-13-trans prostenoic acid |
| 166 | dl-16-hydroxy-9-oxo-16-fluoromethyl-20-ethyl-2-homo-13-trans prostenoic acid | dl-9α,16-dihydroxy-16-fluoromethyl-20-ethyl-2-homo-13-trans prostenoic acid |
| 167 | dl-16-hydroxy-9-oxo-16-difluoromethyl-20-ethyl-2-homo-13-trans prostenoic acid | dl-9α,16-dihydroxy-16-difluoromethyl-20-ethyl-2-homo-13-trans prostenoic acid |
| 168 | dl-16-hydroxy-9-oxo-16-trifluoromethyl-20-ethyl-2-homo-13-trans prostenoic acid | dl-9α,16-dihydroxy-16-trifluoromethyl-20-ethyl-2-homo-13-trans prostenoic acid |

TABLE I (continued)

Treatment of the PGE$_1$ derivatives of Examples 1–84 of Table I with sodium borohydride by the procedure of Reference Example 21 is productive of the PFG$_\alpha$ and PGF$_\beta$ derivatives of Examples 169 to 252 of Table I. Although the 9β product is listed, it will be understood that the corresponding 9α is also produced by the exemplified reaction. The 9α and 9β products are separable, however, by silica gel chromatography.

| EXAMPLE | STARTING PROSTAGLANDIN OF THE PGE SERIES | PRODUCT PROSTAGLANDIN OF THE PGF$_{1\beta}$ SERIES |
|---|---|---|
| 169 | dl-11α,16-dihydroxy-9-oxo-16-fluoromethyl-20-nor-2-nor-13-trans prostenoic acid | dl-9β,11α,16-trihydroxy-16-fluoromethyl-20-nor-2-nor-13-trans prostenoic acid |
| 170 | dl-11,16-dihydroxy-9-oxo-16-difluoromethyl-20-nor-2-nor-13-trans prostenoic acid | dl-9β,11α,16-trihydroxy-16-difluoromethyl-20-nor-2-nor-13-trans prostenoic acid |
| 171 | dl-11α,16-dihydroxy-9-oxo-16-trifluoromethyl-20-nor-2-nor-13-trans prostenoic acid | dl-9β,11α,16-trihydroxy-16-trifluoromethyl-20-nor-2-nor-13-trans prostenoic acid |
| 172 | dl-11α,16-dihydroxy-9-oxo-16-fluoromethyl-2-nor-13-trans prostenoic acid | dl-9α,11β,16-trihydroxy-16-fluoromethyl-2-nor-13-trans prostenoic acid |
| 173 | dl-11α,16-dihydroxy-9-oxo-16-difluoromethyl-2-nor-13-trans prostenoic acid | dl-9β,11α,16-trihydroxy-16-difluoromethyl-2-nor-13-trans prostenoic acid |
| 174 | dl-11,16-dihydroxy-9-oxo-16-trifluoromethyl-2-nor-13-trans prostenoic acid | dl-9β,11α,16-trihydroxy-16-trifluoromethyl-2-nor-13-trans prostenoic acid |
| 175 | dl-11α,16-dihydroxy-9-oxo-16-fluoromethyl-20-methyl-2-nor-13-trans prostenoic acid | dl-9β,11α,16-trihydroxy-16-fluoromethyl-20-methyl-2-nor-13-trans prostenoic acid |
| 176 | dl-11α,16-dihydroxy-9-oxo-16-difluoromethyl-20-methyl-2-nor-13-trans prostenoic acid | dl-9β,11α,16-trihydroxy-16-difluoromethyl-20-methyl-2-nor-13-trans prostenoic acid |
| 177 | dl-11α,16-dihydroxy-9-oxo-16-trifluoromethyl-20-methyl-2-nor-13-trans prostenoic acid | dl-9β,11α,16-trihydroxy-16-trifluoromethyl-20-methyl-2-nor-13-trans prostenoic acid |
| 178 | dl-11α,16-dihydroxy-9-oxo-16-fluoromethyl-20-ethyl-2-nor-13-trans prostenoic acid | dl-9β,11α,16-trihydroxy-16-fluoromethyl-20-ethyl-2-nor-13-trans prostenoic acid |
| 179 | dl-11,16-dihydroxy-9-oxo-16-difluoromethyl-20-ethyl-2-nor-13-trans prostenoic acid | dl-9β,11α,16-trihydroxy-16-difluoromethyl-20-ethyl-2-nor-13-trans prostenoic acid |
| 180 | dl-11α,16-dihydroxy-9-oxo-16-trifluoromethyl-20-ethyl-2-nor-13-trans prostenoic acid | dl-9β,11α,16-trihydroxy-16-trifluoromethyl-20-ethyl-2-nor-13-trans prostenoic acid |
| 181 | dl-11α,16-dihydroxy-9-oxo-16-fluoromethyl-20-nor-13-trans prostenoic acid | dl-9β,11α,16-trihydroxy-16-fluoromethyl-20-nor-13-trans prostenoic acid |
| 182 | dl-11α,16-dihydroxy-9-oxo-16-difluoromethyl-20-nor-13-trans prostenoic acid | dl-9β,11α,16-trihydroxy-16-difluoromethyl-20-nor-13-trans prostenoic acid |
| 183 | dl-11α,16-dihydroxy-9-oxo-16-trifluoromethyl-20-nor-13-trans prostenoic acid | dl-9β,11α,16-trihydroxy-16-trifluoromethyl-20-nor-13-trans prostenoic acid |
| 184 | dl-11α,16-dihydroxy-9-oxo-16-fluoromethyl-13-trans prostenoic acid | dl-9β,11α,16-trihydroxy-16-fluoromethyl-13-trans prostenoic acid |
| 185 | dl-11α,16-dihydroxy-9-oxo-16-difluoromethyl-13-trans prostenoic acid | dl-9β,11α,16-trihydroxy-16-difluoromethyl-13-trans prostenoic acid |
| 186 | dl-11α,16-dihydroxy-9-oxo-16-trifluoromethyl-13-trans prostenoic acid | dl-9β,11α,16-trihydroxy-16-trifluoromethyl-13-trans prostenoic acid |
| 187 | dl-11α,16-dihydroxy-9-oxo-16-fluoromethyl-20-methyl-13-trans prostenoic acid | dl-9β,11α,16-trihydroxy-16-fluoromethyl-20-methyl-13-trans prostenoic acid |
| 188 | dl-11α,16-dihydroxy-9-oxo-16-difluoromethyl-20-methyl-13-trans prostenoic acid | dl-9β,11α,16-trihydroxy-16-difluoromethyl-20-methyl-13-trans prostenoic acid |
| 189 | dl-11α,16-dihydroxy-9-oxo-16-trifluoromethyl-20-methyl-13-trans prostenoic acid | dl-9β,11α,16-trihydroxy-16-trifluoromethyl-20-methyl-13-trans prostenoic acid |
| 190 | dl-11α,16-dihydroxy-9-oxo-16-fluoromethyl-20-ethyl-13-trans prostenoic acid | dl-9β,11α,16-trihydroxy-16-fluoromethyl-20-ethyl-13-trans prostenoic acid |
| 191 | dl-11α,16-dihydroxy-9-oxo-16-difluoromethyl-20-ethyl-13-trans prostenoic acid | dl-9β,11α,16-trihydroxy-16-difluoromethyl-20-ethyl-13-trans prostenoic acid |
| 192 | dl-11α,16-dihydroxy-9-oxo-16-trifluoromethyl-20-ethyl-13-trans prostenoic acid | dl-9β,11α,16-trihydroxy-16-trifluoromethyl-20-ethyl-13-trans prostenoic acid |
| 193 | dl-11α,16-dihydroxy-9-oxo-16-fluoromethyl-20-nor-2-homo-13-trans prostenoic acid | dl-9β,11α,16-trihydroxy-16-fluoromethyl-20-nor-2-homo-13-trans prostenoic acid |
| 194 | dl-11α,16-dihydroxy-9-oxo-16-difluoromethyl-20-nor-2-homo-13-trans prostenoic acid | dl-9β,11α,16-trihydroxy-16-difluoromethyl-20-nor-2-homo-13-trans prostenoic acid |
| 195 | dl-11α,16-dihydroxy-9-oxo-16-trifluoromethyl-20-nor-2-homo-13-trans prostenoic acid | dl-9β,11α,16-trihydroxy-16-trifluoromethyl-20-nor-2-homo-13-trans prostenoic acid |

| | | |
|---|---|---|
| 196 | dl-11,16-dihydroxy-9-oxo-16-fluoromethyl-2-homo-13-trans prostenoic acid | dl-9,11,16-trihydroxy-16-fluoromethyl-2-homo-13-trans prostenoic acid |
| 197 | dl-11,16-dihydroxy-9-oxo-16-difluoromethyl-2-homo-13-trans prostenoic acid | dl-9,11,16-trihydroxy-16-difluoromethyl-2-homo-13-trans prostenoic acid |
| 198 | dl-11,16-dihydroxy-9-oxo-16-trifluoromethyl-2-homo-13-trans prostenoic acid | dl-9,11,16-trihydroxy-16-trifluoromethyl-2-homo-13-trans prostenoic acid |
| 199 | dl-11,16-dihydroxy-9-oxo-16-fluoromethyl-20-methyl-2-homo-13-trans prostenoic acid | dl-9,11,16-trihydroxy-16-fluoromethyl-20-methyl-2-homo-13-trans prostenoic acid |
| 200 | dl-11α,16-dihydroxy-9-oxo-16-difluoromethyl-20-methyl-2-homo-13-trans prostenoic acid | dl-9β,11α,16-trihydroxy-16-difluoromethyl-20-methyl-2-homo-13-trans prostenoic acid |
| 201 | dl-11α,16-dihydroxy-9-oxo-16-trifluoromethyl-20-methyl-2-homo-13-trans prostenoic acid | dl-9β,11α,16-trihydroxy-16-trifluoromethyl-20-methyl-2-homo-13-trans prostenoic acid |
| 202 | dl-11α,16-dihydroxy-9-oxo-16-fluoromethyl-20-ethyl-2-homo-13-trans prostenoic acid | dl-9β,11α,16-trihydroxy-16-fluoromethyl-20-ethyl-2-homo-13-trans prostenoic acid |
| 203 | dl-11α,16-dihydroxy-9-oxo-16-difluoromethyl-20-ethyl-2-homo-13-trans prostenoic acid | dl-9β,11α,16-trihydroxy-16-difluoromethyl-20-ethyl-2-homo-13-trans prostenoic acid |
| 204 | dl-11α,16-dihydroxy-9-oxo-16-trifluoromethyl-20-ethyl-2-homo-13-trans prostenoic acid | dl-9β,11α,16-trihydroxy-16-trifluoromethyl-20-ethyl-2-homo-13-trans prostenoic acid |
| 205 | nat-11α,16-dihydroxy-9-oxo-16-fluoromethyl-20-nor-13-trans prostenoic acid | nat-9β,11α,16-trihydroxy-16-fluoromethyl-20-nor-13-trans prostenoic acid |
| 206 | nat-11α,16-dihydroxy-9-oxo-16-difluoromethyl-20-nor-13-trans prostenoic acid | nat-9β,11α,16-trihydroxy-16-difluoromethyl-20-nor-13-trans prostenoic acid |
| 207 | nat-11α,16-dihydroxy-9-oxo-16-trifluoromethyl-20-nor-13-trans prostenoic acid | nat-9β,11α,16-trihydroxy-16-trifluoromethyl-20-nor-13-trans prostenoic acid |
| 208 | nat-11α,16-dihydroxy-9-oxo-16-fluoromethyl-13-trans prostenoic acid | nat-9β,11α,16-trihydroxy-16-fluoromethyl-13-trans prostenoic acid |
| 209 | nat-11α,16-dihydroxy-9-oxo-16-difluoromethyl-13-trans prostenoic acid | nat-9β,11α,16-trihydroxy-16-difluoromethyl-13-trans prostenoic acid |
| 210 | nat-11α,16-dihydroxy-9-oxo-16-trifluoromethyl-13-trans prostenoic acid | nat-9β,16-trihydroxy-16-trifluoromethyl-13-trans prostenoic acid |
| 211 | nat-11α,16-dihydroxy-9-oxo-16-fluoromethyl-20-methyl-13-trans prostenoic acid | nat-9β,11α,16-trihydroxy-16-fluoromethyl-20-methyl-13-trans prostenoic acid |
| 212 | nat-11α,16-dihydroxy-9-oxo-16-difluoromethyl-20-methyl-13-trans prostenoic acid | nat-9β,11α,16-trihydroxy-16-difluoromethyl-20-methyl-13-trans prostenoic acid |
| 213 | nat-11α,16-dihydroxy-9-oxo-16-trifluoromethyl-20-methyl-13-trans prostenoic acid | nat-9β,11α,16-trihydroxy-16-trifluoromethyl-20-methyl-13-trans prostenoic acid |
| 214 | nat-11α,16-dihydroxy-9-oxo-16-fluoromethyl-20-ethyl-13-trans prostenoic acid | nat-9β,11α,16-trihydroxy-16-fluoromethyl-20-ethyl-13-trans prostenoic acid |
| 215 | nat-11α,16-dihydroxy-9-oxo-16-difluoromethyl-20-ethyl-13-trans prostenoic acid | nat-9β,11α,16-trihydroxy-16-difluoromethyl-20-ethyl-13-trans prostenoic acid |
| 216 | nat-11α,16-dihydroxy-9-oxo-16-trifluoromethyl-20-ethyl-13-trans prostenoic acid | nat-9β,11α,16-trihydroxy-16-trifluoromethyl-20-ethyl-13-trans prostenoic acid |
| 217 | dl-16-hydroxy-9-oxo-16-fluoromethyl-20-nor-2-nor-13-trans prostenoic acid | dl-9β,16-dihydroxy-16-fluoromethyl-20-nor-2-nor-13-trans prostenoic acid |
| 218 | dl-16-hydroxy-9-oxo-16-difluoromethyl-20-nor-2-nor-13-trans prostenoic acid | dl-9β,16-dihydroxy-16-difluoromethyl-20-nor-2-nor-13-trans prostenoic acid |
| 219 | dl-16-hydroxy-9-oxo-16-trifluoromethyl-20-nor-2-nor-13-trans prostenoic acid | dl-9β,16-dihydroxy-16-trifluoromethyl-20-nor-2-nor-13-trans prostenoic acid |
| 220 | dl-16-hydroxy-9-oxo-16-fluoromethyl-2-nor-13-trans prostenoic acid | dl-9β,16-dihydroxy-16-fluoromethyl-2-nor-13-trans prostenoic acid |
| 221 | dl-16-hydroxy-9-oxo-16-difluoromethyl-2-nor-13-trans prostenoic acid | dl-9β,16-dihydroxy-16-difluoromethyl-2-nor-13-trans prostenoic acid |
| 222 | dl-16-hydroxy-9-oxo-16-trifluoromethyl-2-nor-13-trans prostenoic acid | dl-9β,16-dihydroxy-16-trifluoromethyl-2-nor-13-trans prostenoic acid |
| 223 | dl-16-hydroxy-9-oxo-16-fluoromethyl-20-methyl-2-nor-13-trans prostenoic acid | dl-9β,16-dihydroxy-16-fluoromethyl-20-methyl-2-nor-13-trans prostenoic acid |
| 224 | dl-16-hydroxy-9-oxo-16-difluoromethyl-20-methyl-2-nor-13-trans prostenoic acid | dl-9β,16-dihydroxy-16-difluoromethyl-20-methyl-2-nor-13-trans prostenoic acid |
| 225 | dl-16-hydroxy-9-oxo-16-trifluoromethyl-20-methyl-2-nor-13-trans prostenoic acid | dl-9β,16-dihydroxy-16-trifluoromethyl-20-methyl-2-nor-13-trans prostenoic acid |
| 226 | dl-16-hydroxy-9-oxo-16-fluoromethyl-20-ethyl-2-nor-13-trans prostenoic acid | dl-9β,16-dihydroxy-16-fluoromethyl-20-ethyl-2-nor-13-trans prostenoic acid |
| 227 | dl-16-hydroxy-9-oxo-16-difluoromethyl-20-ethyl-2-nor-13-trans prostenoic acid | dl-9β,16-dihydroxy-16-difluoromethyl-20-ethyl-2-nor-13-trans prostenoic acid |
| 228 | dl-16-hydroxy-9-oxo-16-trifluoromethyl-20-ethyl-2-nor-13-trans prostenoic acid | dl-9β,16-dihydroxy-16-trifluoromethyl-20-ethyl-2-nor-13-trans prostenoic acid |
| 229 | dl-16-hydroxy-9-oxo-16-fluoromethyl-20-nor-13-trans prostenoic acid | dl-9β,16-dihydroxy-16-fluoromethyl-20-nor-13-trans prostenoic acid |
| 230 | dl-16-hydroxy-9-oxo-16-difluoromethyl-20-nor-13-trans prostenoic acid | dl-9β,16-dihydroxy-16-difluoromethyl-20-nor-13-trans prostenoic acid |
| 231 | dl-16-hydroxy-9-oxo-16-trifluoromethyl-20-nor-13-trans prostenoic acid | dl-9β,16-dihydroxy-16-trifluoromethyl-20-nor-13-trans prostenoic acid |
| 232 | dl-16-hydroxy-9-oxo-16-fluoromethyl-13-trans prostenoic acid | dl-9β,16-dihydroxy-16-fluoromethyl-13-trans prostenoic acid |
| 233 | dl-16-hydroxy-9-oxo-16-difluoromethyl- | dl-9β,16-dihydroxy-16-difluoromethyl- |

| | | -continued |
|---|---|---|
| | | 13-trans prostenoic acid | 13-trans prostenoic acid |
| 234 | dl-16-hydroxy-9-oxo-16-trifluoromethyl-13-trans prostenoic acid | dl-9β,16-dihydroxy-16-trifluoromethyl-13-trans prostenoic acid |
| 235 | dl-16-hydroxy-9-oxo-16-fluoromethyl-20-methyl-13-trans prostenoic acid | dl-9β,16-dihydroxy-16-fluoromethyl-20-methyl-13-trans prostenoic acid |
| 236 | dl-16-hydroxy-9-oxo-16-difluoromethyl-20-methyl-13-trans-prostenoic acid | dl-9β,16-dihydroxy-16-difluoromethyl-20-methyl-13-trans prostenoic acid |
| 237 | dl-16-hydroxy-9-oxo-16-trifluoromethyl-20-methyl-13-trans prostenoic acid | dl-9β,16-dihydroxy-16-trifluoromethyl-20-methyl-13-trans prostenoic acid |
| 238 | dl-16-hydroxy-9-oxo-16-fluoromethyl-20-ethyl-13-trans prostenoic acid | dl-9β,16-dihydroxy-16-fluoromethyl-20-ethyl-13-trans prostenoic acid |
| 239 | dl-16-hydroxy-9-oxo-16-difluoromethyl-20-ethyl-13-trans prostenoic acid | dl-9β,16-dihydroxy-16-difluoromethyl-20-ethyl-13-trans prostenoic acid |
| 240 | dl-16-hydroxy-9-oxo-16-trifluoromethyl-20-ethyl-13-trans prostenoic acid | dl-9β,16-dihydroxy-16-trifluoromethyl-20-ethyl-13-trans prostenoic acid |
| 241 | dl-16-hydroxy-9-oxo-16-fluoromethyl-20-nor-2-homo-13-trans prostenoic acid | dl-9β,16-dihydroxy-16-fluoromethyl-20-nor-2-homo-13-trans prostenoic acid |
| 242 | dl-16-hydroxy-9-oxo-16-difluoromethyl-20-nor-2-homo-13-trans prostenoic acid | dl-9β,16-dihydroxy-16-difluoromethyl-20-nor-2-homo-13-trans prostenoic acid |
| 243 | dl-16-hydroxy-9-oxo-16-trifluoromethyl-20-nor-2-homo-13-trans prostenoic acid | dl-9β,16-dihydroxy-16-trifluoromethyl-20-nor-2-homo-13-trans prostenoic acid |
| 244 | dl-16-hydroxy-9-oxo-16-fluoromethyl-2-homo-13-trans prostenoic acid | dl-9β,16-dihydroxy-16-fluoromethyl-2-homo-13-trans prostenoic acid |
| 245 | dl-16-hydroxy-9-oxo-16-difluoromethyl-2-homo-13-trans prostenoic acid | dl-9β,16-dihydroxy-16-difluoromethyl-2-homo-13-trans prostenoic acid |
| 246 | dl-16-hydroxy-9-oxo-16-trifluoromethyl-2-homo-13-trans prostenoic acid | dl-9β,16-dihydroxy-16-trifluoromethyl-2-homo-13-trans prostenoic acid |
| 247 | dl-16-hydroxy-9-oxo-16-fluoromethyl-20-methyl-2-homo-13-trans prostenoic acid | dl-9β,16-dihydroxy-16-fluoromethyl-20-methyl-2-homo-13-trans prostenoic acid |
| 248 | dl-16-hydroxy-9-oxo-16-difluoromethyl-20-methyl-2-homo-13-trans prostenoic acid | dl-9β,16-dihydroxy-16-difluoromethyl-20-methyl-2-homo-13-trans prostenoic acid |
| 249 | dl-16-hydroxy-9-oxo-16-trifluoromethyl-20-methyl-2-homo-13-trans prostenoic acid | dl-9β,16-dihydroxy-16-trifluoromethyl-20-methyl-2-homo-13-trans prostenoic acid |
| 250 | dl-16-hydroxy-9-oxo-16-fluoromethyl-20-ethyl-2-homo-13-trans prostenoic acid | dl-9β,16-dihydroxy-16-fluoromethyl-20-ethyl-2-homo-13-trans prostenoic acid |
| 251 | dl-16-hydroxy-9-oxo-16-difluoromethyl-20-ethyl-2-homo-13-trans prostenoic acid | dl-9β,16-dihydroxy-16-difluoromethyl-20-ethyl-2-homo-13-trans prostenoic acid |
| 252 | dl-16-hydroxy-9-oxo-16-trifluoromethyl-20-ethyl-2-homo-13-trans prostenoic acid | dl-9β,16-dihydroxy-16-trifluoromethyl-20-ethyl-2-homo-13-trans prostenoic acid |

TABLE II

Treatment of the appropriate cyclopentenones of Table C with the lithiocuprates derived from the vinylstannanes or vinyl iodides of Reference Examples 4, 10, 16 and 19 by the procedure of Reference Examples 5 and 6, 11 and 12, 17 and 18 is productive of the PGE$_1$ derivatives of Examples 1–84 of Table II.

| EXAMPLE | VINYL TIN | CYCLOPENTENONE | PRODUCT PROSTAGLANDIN OF THE PGE₂ SERIES |
|---|---|---|---|
| 1 | 1-trans-tri-n-butylstannyl-4-fluoromethyl-4-trimethylsiloxy-1-heptene | 2-(5-carbotrimethylsiloxypent-2-cis-enyl)-4-trimethylsiloxycyclopent-2-en-1-one | dl-11α,16-dihydroxy-9-oxo-16-fluoromethyl-20-nor-2-nor-5-cis-13-trans prostadienoic acid |
| 2 | 1-trans-tri-n-butylstannyl-4-difluoromethyl-4-trimethylsiloxy-1-heptene | 2-(5-carbotrimethylsiloxypent-2-cis-enyl)-4-trimethylsiloxycyclopent-2-en-1-one | dl-11α,16-dihydroxy-9-oxo-16-difluoromethyl-20-nor-2-nor-5-cis-13-trans prostadienoic acid |
| 3 | 1-trans-tri-n-butylstannyl-4-trifluoromethyl-4-trimethylsiloxy-1-heptene | 2-(5-carbotrimethylsiloxypent-2-cis-enyl)-4-trimethylsiloxycyclopent-2-en-1-one | dl-11α,16-dihydroxy-9-oxo-16-trifluoromethyl-20-nor-2-nor-5-cis-13-trans prostadienoic acid |
| 4 | 1-trans-tri-n-butylstannyl-4-fluoromethyl-4-trimethylsiloxy-1-octene | 2-(5-carbotrimethylsiloxypent-2-cis-enyl)-4-trimethylsiloxycyclopent-2-en-1-one | dl-11α,16-dihydroxy-9-oxo-16-fluoromethyl-2-nor-5-cis-trans prostadienoic acid |
| 5 | 1-trans-tri-n-butylstannyl-4-difluoromethyl-4-trimethylsiloxy-1-octene | 2-(5-carbotrimethylsiloxypent-2-cis-enyl)-4-trimethylsiloxycyclopent-2-en-1-one | dl-11α,16-dihydroxy-9-oxo-16-difluoromethyl-2-nor-5-cis-13-trans prostadienoic acid |
| 6 | 1-trans-tri-n-butylstannyl-4-trifluoromethyl-4-trimethylsiloxy-1-octene | 2-(5-carbotrimethylsiloxypent-2-cis-enyl)-4-trimethylsiloxycyclopent-2-en-1-one | dl-11α,16-dihydroxy-9-oxo-16-trifluoromethyl-2-nor-5-cis-13-trans prostadienoic acid |
| 7 | 1-trans-tri-n-butylstannyl-4-fluoromethyl-4-trimethylsiloxy-1-nonene | 2-(5-carbotrimethylsiloxypent-2-cis-enyl)-4-trimethylsiloxycyclopent-2-en-1-one | dl-11α,16-dihydroxy-9-oxo-16-fluoromethyl-20-methyl-2-nor-5-cis-13-trans prostadienoic acid |
| 8 | 1-trans-tri-n-butylstannyl-4-difluoromethyl-4-trimethylsiloxy-1-nonene | 2-(5-carbotrimethylsiloxypent-2-cis-enyl)-4-trimethylsiloxycyclopent-2-en-1-one | dl-11α,16-dihydroxy-9-oxo-16-difluoromethyl-20-methyl-2-nor-5-cis-13-trans prostadienoic acid |
| 9 | 1-trans-tri-n-butylstannyl-4-trifluoromethyl-4-trimethylsiloxy-1-nonene | 2-(5-carbotrimethylsiloxypent-2-cis-enyl)-4-trimethylsiloxycyclopent-2-en-1-one | dl-11α,16-dihydroxy-9-oxo-16-trifluoromethyl-20-methyl-2-nor-5-cis-13-trans prostadienoic acid |
| 10 | 1-trans-tri-n-butylstannyl-4-fluoromethyl-4-trimethylsiloxy-1-decene | 2-(5-carbotrimethylsiloxypent-2-cis-enyl)-4-trimethylsiloxycyclopent-2-en-1-one | dl-11α,16-dihydroxy-9-oxo-16-fluoromethyl-20-ethyl-2-nor-5-cis-13-trans prostadienoic acid |
| 11 | 1-trans-tri-n-butylstannyl-4-difluoromethyl-4-trimethylsiloxy-1-decene | 2-(5-carbotrimethylsiloxypent-2-cis-enyl)-4-trimethylsiloxycyclopent-2-en-1-one | dl-11α,16-dihydroxy-9-oxo-16-difluoromethyl-20-ethyl-2-nor-5-cis-13-trans prostadienoic acid |
| 12 | 1-trans-tri-n-butylstannyl-4-trifluoromethyl-4-trimethylsiloxy-1-decene | 2-(5-carbotrimethylsiloxypent-2-cis-enyl)-4-trimethylsiloxycyclopent-2-en-1-one | dl-11α,16-dihydroxy-9-oxo-16-trifluoromethyl-20-ethyl-2-nor-5-cis-13-trans prostadienoic acid |
| 13 | 1-trans-tri-n-butylstannyl-4-fluoromethyl-4-trimethylsiloxy-1-heptene | 2-(6-carbotrimethylsiloxyhex-2-cis-enyl)-4-trimethylsiloxycyclopent-2-en-1-one | dl-11α,16-dihydroxy-9-oxo-16-fluoromethyl-20-nor-5-cis-13-trans prostadienoic acid |
| 14 | 1-trans-tri-n-butylstannyl-4-difluoromethyl-4-trimethylsiloxy-1-heptene | 2-(6-carbotrimethylsiloxyhex-2-cis-enyl)-4-trimethylsiloxycyclopent-2-en-1-one | dl-11α,16-dihydroxy-9-oxo-16-difluoromethyl-20-nor-5-cis-13-trans prostadienoic acid |
| 15 | 1-trans-tri-n-butylstannyl-4-trifluoromethyl-4-trimethylsiloxy-1-heptene | 2-(6-carbotrimethylsiloxyhex-2-cis-enyl)-4-trimethylsiloxycyclopent-2-en-1-one | dl-11α,16-dihydroxy-9-oxo-16-trifluoromethyl-20-nor-5-cis-13-trans prostadienoic acid |
| 16 | 1-trans-tri-n-butylstannyl-4-fluoromethyl-4-trimethylsiloxy-1-octene | 2-(6-carbotrimethylsiloxyhex-2-cis-enyl)-4-trimethylsiloxycyclopent-2-en-1-one | dl-11α,16-dihydroxy-9-oxo-16-fluoromethyl-5-cis-13-trans prostadienoic acid |
| 17 | 1-trans-tri-n-butylstannyl-4-difluoromethyl-4-trimethylsiloxy-1-octene | 2-(6-carbotrimethylsiloxyhex-2-cis-enyl)-4-trimethylsiloxycyclopent-2-en-1-one | dl-11α,16-dihydroxy-9-oxo-16-difluoromethyl-5-cis-13-trans prostadienoic acid |
| 18 | 1-trans-tri-n-butylstannyl-4-trifluoromethyl-4-trimethylsiloxy-1-octene | 2-(6-carbotrimethylsiloxyhex-2-cis-enyl)-4-trimethylsiloxycyclopent-2-en-1-one | dl-11α,16-dihydroxy-9-oxo-16-trifluoromethyl-5-cis-13-trans prostadienoic acid |
| 19 | 1-trans-tri-n-butylstannyl-4-fluoromethyl-4-trimethylsiloxy-1-nonene | 2-(6-carbotrimethylsiloxyhex-2-cis-enyl)-4-trimethylsiloxycyclopent-2-en-1-one | dl-11α,16-dihydroxy-9-oxo-16-fluoromethyl-20-methyl-5-cis-13-trans prostadienoic acid |
| 20 | 1-trans-tri-n-butylstannyl-4-difluoromethyl-4-trimethylsiloxy-1-nonene | 2-(6-carbotrimethylsiloxyhex-2-cis-enyl)-4-trimethylsiloxycyclopent-2-en-1-one | dl-11α,16-dihydroxy-9-oxo-16-difluoromethyl-20-methyl-5-cis-13-trans prostadienoic acid |
| 21 | 1-trans-tri-n-butylstannyl-4-trifluoromethyl-4-trimethylsiloxy-1-nonene | 2-(6-carbotrimethylsiloxyhex-2-cis-enyl)-4-trimethylsiloxycyclopent-2-en-1-one | dl-11α,16-dihydroxy-9-oxo-16-trifluoromethyl-20-methyl-5-cis-13-trans prostadienoic acid |
| 22 | 1-trans-tri-n-butylstannyl-4-fluoromethyl-4-trimethylsiloxy-1-decene | 2-(6-carbotrimethylsiloxyhex-2-cis-enyl)-4-trimethylsiloxycyclopent-2-en-1-one | dl-11α,16-dihydroxy-9-oxo-16-fluoromethyl-20-ethyl-5-cis-13-trans prostadienoic acid |
| 23 | 1-trans-tri-n-butylstannyl-4-difluoromethyl-4-trimethylsiloxy-1-decene | 2-(6-carbotrimethylsiloxyhex-2-cis-enyl)-4-trimethylsiloxycyclopent-2-en-1-one | dl-11α,16-dihydroxy-9-oxo-16-difluoromethyl-20-ethyl-5-cis-13-trans prostadienoic acid |
| 24 | 1-trans-tri-n-butylstannyl-4-trifluoromethyl-4-trimethylsiloxy-1-decene | 2-(6-carbotrimethylsiloxyhex-2-cis-enyl)-4-trimethylsiloxycyclopent-2-en-1-one | dl-11α,16-dihydroxy-9-oxo-16-trifluoromethyl-20-ethyl-5-cis-13-trans prostadienoic acid |
| 25 | 1-trans-tri-n-butylstannyl-4-fluoromethyl-4-trimethylsiloxy-1-heptene | 2-(7-carbotrimethylsiloxyhept-2-cis-enyl)-4-trimethylsiloxycyclopent-2-en-1-one | dl-11α,16-dihydroxy-9-oxo-16-fluoromethyl-20-nor-2-homo-5-cis-13-trans prostadienoic acid |
| 26 | 1-trans-tri-n-butylstannyl-4-difluoromethyl-4-trimethylsiloxy-1-heptene | 2-(7-carbotrimethylsiloxyhept-2-cis-enyl)-4-trimethylsiloxycyclopent-2-en-1-one | dl-11α,16-dihydroxy-9-oxo-16-difluoromethyl-20-nor-2-homo-5-cis-13-trans prostadienoic acid |

-continued

| | | | |
|---|---|---|---|
| 27 | 1-trans-tri-n-butylstannyl-4-trifluoromethyl-4-trimethylsiloxy-1-heptene | 2-(7-carbotrimethylsilyoxyhept-2-cis-enyl)-4-trimethylsiloxycyclopent-2-en-1-one | dl-11α,16-dihydroxy-9-oxo-16-trifluoromethyl-20-nor-2-homo-5-cis-13-trans prostadienoic acid |
| 28 | 1-trans-tri-n-butylstannyl-4-fluoromethyl-4-trimethylsiloxy-1-heptene | 2-(7-carbotrimethylsilyoxyhept-2-cis-enyl)-4-trimethylsiloxycyclopent-2-en-1-one | dl-11α,16-dihydroxy-9-oxo-16-fluoromethyl-2-homo-5-cis-13-trans prostadienoic acid |
| 29 | 1-trans-tri-n-butylstannyl-4-difluoromethyl-4-trimethylsiloxy-1-octene | 2-(7-carbotrimethylsilyoxyhept-2-cis-enyl)-4-trimethylsiloxycyclopent-2-en-1-one | dl-11α,16-dihydroxy-9-oxo-16-difluoromethyl-2-homo-5-cis-13-trans prostadienoic acid |
| 30 | 1-trans-tri-n-butylstannyl-4-trifluoromethyl-4-trimethylsiloxy-1-octene | 2-(7-carbotrimethylsilyoxyhept-2-cis-enyl)-4-trimethylsiloxycyclopent-2-en-1-one | dl-11α,16-dihydroxy-9-oxo-16-trifluoromethyl-2-homo-5-cis-13-trans prostadienoic acid |
| 31 | 1-trans-tri-n-butylstannyl-4-fluoromethyl-4-trimethylsiloxy-1-octene | 2-(7-carbotrimethylsilyoxyhept-2-cis-enyl)-4-trimethylsiloxycyclopent-2-en-1-one | dl-11α,16-dihydroxy-9-oxo-16-fluoromethyl-2-homo-5-cis-13-trans prostadienoic acid |
| 32 | 1-trans-tri-n-butylstannyl-4-difluoromethyl-4-trimethylsiloxy-1-nonene | 2-(7-carbotrimethylsilyoxyhept-2-cis-enyl)-4-trimethylsiloxycyclopent-2-en-1-one | dl-11α,16-dihydroxy-9-oxo-16-difluoromethyl-20-methyl-2-homo-5-cis-13-trans prostadienoic acid |
| 33 | 1-trans-tri-n-butylstannyl-4-trifluoromethyl-4-trimethylsiloxy-1-nonene | 2-(7-carbotrimethylsilyoxyhept-2-cis-enyl)-4-trimethylsiloxycyclopent-2-en-1-one | dl-11α,16-dihydroxy-9-oxo-16-trifluoromethyl-20-methyl-2-homo-5-cis-13-trans prostadienoic acid |
| 34 | 1-trans-tri-n-butylstannyl-4-fluoromethyl-4-trimethylsiloxy-1-nonene | 2-(7-carbotrimethylsilyoxyhept-2-cis-enyl)-4-trimethylsiloxycyclopent-2-en-1-one | dl-11α,16-dihydroxy-9-oxo-16-fluoromethyl-20-methyl-2-homo-5-cis-13-trans prostadienoic acid |
| 35 | 1-trans-tri-n-butylstannyl-4-difluoromethyl-4-trimethylsiloxy-1-decene | 2-(7-carbotrimethylsilyoxyhept-2-cis-enyl)-4-trimethylsiloxycyclopent-2-en-1-one | dl-11α,16-dihydroxy-9-oxo-16-difluoromethyl-20-ethyl-2-homo-5-cis-13-trans prostadienoic acid |
| 36 | 1-trans-tri-n-butylstannyl-4-trifluoromethyl-4-trimethylsiloxy-1-decene | 2-(7-carbotrimethylsilyoxyhept-2-cis-enyl)-4-trimethylsiloxycyclopent-2-en-1-one | dl-11α,16-dihydroxy-9-oxo-16-trifluoromethyl-20-ethyl-2-homo-5-cis-13-trans prostadienoic acid |
| 37 | 1-trans-tri-n-butylstannyl-4-fluoromethyl-4-trimethylsiloxy-1-heptene | 2-(6-carbotrimethylsilyoxyhex-2-cis-enyl)-4R-trimethylsiloxycyclopent-2-en-1-one | nat-11α,16-dihydroxy-9-oxo-16-fluoromethyl-20-nor-5-cis-13-trans prostadienoic acid |
| 38 | 1-trans-tri-n-butylstannyl-4-difluoromethyl-4-trimethylsiloxy-1-octene | 2-(6-carbotrimethylsilyoxyhex-2-cis-enyl)-4R-trimethylsiloxycyclopent-2-en-1-one | nat-11α,16-dihydroxy-9-oxo-16-difluoromethyl-20-nor-5-cis-13-trans prostadienoic acid |
| 39 | 1-trans-tri-n-butylstannyl-4-trifluoromethyl-4-trimethylsiloxy-1-octene | 2-(6-carbotrimethylsilyoxyhex-2-cis-enyl)-4R-trimethylsiloxycyclopent-2-en-1-one | nat-11α,16-dihydroxy-9-oxo-16-trifluoromethyl-20-nor-5-cis-13-trans prostadienoic acid |
| 40 | 1-trans-tri-n-butylstannyl-4-fluoromethyl-4-trimethylsiloxy-1-octene | 2-(6-carbotrimethylsilyoxyhex-2-cis-enyl)-4R-trimethylsiloxycyclopent-2-en-1-one | nat-11α,16-dihydroxy-9-oxo-16-fluoromethyl-5-cis-13-trans prostadienoic acid |
| 41 | 1-trans-tri-n-butylstannyl-4-difluoromethyl-4-trimethylsiloxy-1-nonene | 2-(6-carbotrimethylsilyoxyhex-2-cis-enyl)-4R-trimethylsiloxycyclopent-2-en-1-one | nat-11α,16-dihydroxy-9-oxo-16-difluoromethyl-5-cis-13-trans prostadienoic acid |
| 42 | 1-trans-tri-n-butylstannyl-4-trifluoromethyl-4-trimethylsiloxy-1-nonene | 2-(6-carbotrimethylsilyoxyhex-2-cis-enyl)-4R-trimethylsiloxycyclopent-2-en-1-one | nat-11α,16-dihydroxy-9-oxo-16-trifluoromethyl-5-cis-13-trans prostadienoic acid |
| 43 | 1-trans-tri-n-butylstannyl-4-fluoromethyl-4-trimethylsiloxy-1-nonene | 2-(6-carbotrimethylsilyoxyhex-2-cis-enyl)-4R-trimethylsiloxycyclopent-2-en-1-one | nat-11α,16-dihydroxy-9-oxo-16-fluoromethyl-20-methyl-5-cis-13-trans prostadienoic acid |
| 44 | 1-trans-tri-n-butylstannyl-4-difluoromethyl-4-trimethylsiloxy-1-decene | 2-(6-carbotrimethylsilyoxyhex-2-cis-enyl)-4R-trimethylsiloxycyclopent-2-en-1-one | nat-11α,16-dihydroxy-9-oxo-16-difluoromethyl-20-methyl-5-cis-13-trans prostadienoic acid |
| 45 | 1-trans-tri-n-butylstannyl-4-trifluoromethyl-4-trimethylsiloxy-1-decene | 2-(6-carbotrimethylsilyoxyhex-2-cis-enyl)-4R-trimethylsiloxycyclopent-2-en-1-one | nat-11α,16-dihydroxy-9-oxo-16-trifluoromethyl-20-methyl-5-cis-13-trans prostadienoic acid |
| 46 | 1-trans-tri-n-butylstannyl-4-fluoromethyl-4-trimethylsiloxy-1-decene | 2-(6-carbotrimethylsilyoxyhex-2-cis-enyl)-4R-trimethylsiloxycyclopent-2-en-1-one | nat-11α,16-dihydroxy-9-oxo-16-fluoromethyl-20-ethyl-5-cis-13-trans prostadienoic acid |
| 47 | 1-trans-tri-n-butylstannyl-4-difluoromethyl-4-trimethylsiloxy-1-decene | 2-(6-carbotrimethylsilyoxyhex-2-cis-enyl)-4R-trimethylsiloxycyclopent-2-en-1-one | nat-11α,16-dihydroxy-9-oxo-16-difluoromethyl-20-ethyl-5-cis-13-trans prostadienoic acid |
| 48 | 1-trans-tri-n-butylstannyl-4-trifluoromethyl-4-trimethylsiloxy-1-decene | 2-(6-carbotrimethylsilyoxyhex-2-cis-enyl)-4R-trimethylsiloxycyclopent-2-en-1-one | nat-11α,16-dihydroxy-9-oxo-16-trifluoromethyl-20-ethyl-5-cis-13-trans prostadienoic acid |
| 49 | 1-trans-tri-n-butylstannyl-4-fluoromethyl-4-trimethylsiloxy-1-heptene | 2-(5-carboethoxypent-2-cis-enyl)cyclopent-2-en-1-one | dl-16-hydroxy-9-oxo-16-fluoromethyl-20-nor-2-nor-5-cis-13-trans prostadienoic acid |
| 50 | 1-trans-tri-n-butylstannyl-4-difluoromethyl-4-trimethylsiloxy-1-heptene | 2-(5-carboethoxypent-2-cis-enyl)cyclopent-2-en-1-one | dl-16-hydroxy-9-oxo-16-difluoromethyl-20-nor-2-nor-5-cis-13-trans prostadienoic acid |
| 51 | 1-trans-tri-n-butylstannyl-4-trifluoromethyl-4-trimethylsiloxy-1-heptene | 2-(5-carboethoxypent-2-cis-enyl)cyclopent-2-en-1-one | dl-16-hydroxy-9-oxo-16-trifluoromethyl-20-nor-2-nor-5-cis-13-trans prostadienoic acid |
| 52 | 1-trans-tri-n-butylstannyl-4-fluoromethyl-4-trimethylsiloxy-1-heptene | 2-(5-carboethoxypent-2-cis-enyl) | dl-16-hydroxy-9-oxo-16-fluoromethyl- |

-continued

| | | | |
|---|---|---|---|
| 53 | 4-trimethylsilyloxy-1-octene | cyclopent-2-en-1-one | 2-nor-5-cis-13-trans prostadienoic acid |
| | 1-trans-tri-n-butylstannyl-4-difluoromethyl- | 2-(5-carboethoxypent-2-cis-enyl) | dl-16-hydroxy-9-oxo-16-difluoromethyl- |
| | 4-trimethylsiloxy-1-octene | cyclopent-2-en-1-one | 2-nor-5-cis-13-trans prostadienoic acid |
| 54 | 1-trans-tri-n-butylstannyl-4-trifluoromethyl- | 2-(5-carboethoxypent-2-cis-enyl) | dl-16-hydroxy-9-oxo-16-trifluoromethyl- |
| | 4-trimethylsiloxy-1-octene | cyclopent-2-en-1-one | 2-nor-5-cis-13-trans prostadienoic acid |
| 55 | 1-trans-tri-n-butylstannyl-4-fluoromethyl- | 2-(5-carboethoxypent-2-cis-enyl) | dl-16-hydroxy-9-oxo-16-fluoromethyl- |
| | 4-trimethylsiloxy-1-nonene | cyclopent-2-en-1-one | 20-methyl-2-nor-5-cis-13-trans prostadienoic acid |
| 56 | 1-trans-tri-n-butylstannyl-4-difluoromethyl- | 2-(5-carboethoxypent-2-cis-enyl) | dl-16-hydroxy-9-oxo-16-difluoromethyl- |
| | 4-trimethylsiloxy-1-nonene | cyclopent-2-en-1-one | 20-methyl-2-nor-5-cis-13-trans prostadienoic acid |
| 57 | 1-trans-tri-n-butylstannyl-4-trifluoromethyl- | 2-(5-carboethoxypent-2-cis-enyl) | dl-16-hydroxy-9-oxo-16-trifluoromethyl- |
| | 4-trimethylsiloxy-1-nonene | cyclopent-2-en-1-one | 20-methyl-2-nor-5-cis-13-trans prostadienoic acid |
| 58 | 1-trans-tri-n-butylstannyl-4-fluoromethyl- | 2-(5-carboethoxypent-2-cis-enyl) | dl-16-hydroxy-9-oxo-16-fluoromethyl- |
| | 4-trimethylsiloxy-1-decene | cyclopent-2-en-1-one | 20-ethyl-2-nor-5-cis-13-trans prostadienoic acid |
| 59 | 1-trans-tri-n-butylstannyl-4-difluoromethyl- | 2-(5-carboethoxypent-2-cis-enyl) | dl-16-hydroxy-9-oxo-16-difluoromethyl- |
| | 4-trimethylsiloxy-1-decene | cyclopent-2-en-1-one | 20-ethyl-2-nor-5-cis-13-trans prostadienoic acid |
| 60 | 1-trans-tri-n-butylstannyl-4-trifluoromethyl- | 2-(5-carboethoxypent-2-cis-enyl) | dl-16-hydroxy-9-oxo-16-trifluoromethyl- |
| | 4-trimethylsiloxy-1-decene | cyclopent-2-en-1-one | 20-ethyl-2-nor-5-cis-13-trans prostadienoic acid |
| 61 | 1-trans-tri-n-butylstannyl-4-fluoromethyl- | 2-(6-carboethoxyhex-2-cis-enyl) | dl-16-hydroxy-9-oxo-16-fluoromethyl- |
| | 4-trimethylsiloxy-1-heptene | cyclopent-2-en-1-one | 5-cis-13-trans prostadienoic acid |
| 62 | 1-trans-tri-n-butylstannyl-4-difluoromethyl- | 2-(6-carboethoxyhex-2-cis-enyl) | dl-16-hydroxy-9-oxo-16-difluoromethyl- |
| | 4-trimethylsiloxy-1-heptene | cyclopent-2-en-1-one | 2-nor-5-cis-13-trans prostadienoic acid |
| 63 | 1-trans-tri-n-butylstannyl-4-trifluoromethyl- | 2-(6-carboethoxyhex-2-cis-enyl) | dl-16-hydroxy-9-oxo-16-trifluoromethyl- |
| | 4-trimethylsiloxy-1-heptene | cyclopent-2-en-1-one | 2-nor-5-cis-13-trans prostadienoic acid |
| 64 | 1-trans-tri-n-butylstannyl-4-fluoromethyl- | 2-(6-carboethoxyhex-2-cis-enyl) | dl-16-hydroxy-9-oxo-16-fluoromethyl- |
| | 4-trimethylsiloxy-1-octene | cyclopent-2-en-1-one | 5-cis-13-trans prostadienoic acid |
| 65 | 1-trans-tri-n-butylstannyl-4-difluoromethyl- | 2-(6-carboethoxyhex-2-cis-enyl) | dl-16-hydroxy-9-oxo-16-difluoromethyl- |
| | 4-trimethylsiloxy-1-octene | cyclopent-2-en-1-one | 5-cis-13-trans prostadienoic acid |
| 66 | 1-trans-tri-n-butylstannyl-4-trifluoromethyl- | 2-(6-carboethoxyhex-2-cis-enyl) | dl-16-hydroxy-9-oxo-16-trifluoromethyl- |
| | 4-trimethylsiloxy-1-octene | cyclopent-2-en-1-one | 5-cis-13-trans prostadienoic acid |
| 67 | 1-trans-tri-n-butylstannyl-4-fluoromethyl- | 2-(6-carboethoxyhex-2-cis-enyl) | dl-16-hydroxy-9-oxo-16-fluoromethyl- |
| | 4-trimethylsiloxy-1-nonene | cyclopent-2-en-1-one | 20-methyl-5-cis-13-trans prostadienoic acid |
| 68 | 1-trans-tri-n-butylstannyl-4-difluoromethyl- | 2-(6-carboethoxyhex-2-cis-enyl) | dl-16-hydroxy-9-oxo-16-difluoromethyl- |
| | 4-trimethylsiloxy-1-nonene | cyclopent-2-en-1-one | 20-methyl-5-cis-13-trans prostadienoic acid |
| 69 | 1-trans-tri-n-butylstannyl-4-trifluoromethyl- | 2-(6-carboethoxyhex-2-cis-enyl) | dl-16-hydroxy-9-oxo-16-trifluoromethyl- |
| | 4-trimethylsiloxy-1-nonene | cyclopent-2-en-1-one | 20-methyl-5-cis-13-trans prostadienoic acid |
| 70 | 1-trans-tri-n-butylstannyl-4-fluoromethyl- | 2-(6-carboethoxyhex-2-cis-enyl) | dl-16-hydroxy-9-oxo-16-fluoromethyl- |
| | 4-trimethylsiloxy-1-decene | cyclopent-2-en-1-one | 20-ethyl-5-cis-13-trans prostadienoic acid |
| 71 | 1-trans-tri-n-butylstannyl-4-difluoromethyl- | 2-(6-carboethoxyhex-2-cis-enyl) | dl-16-hydroxy-9-oxo-16-difluoromethyl- |
| | 4-trimethylsiloxy-1-decene | cyclopent-2-en-1-one | 20-ethyl-5-cis-13-trans prostadienoic acid |
| 72 | 1-trans-tri-n-butylstannyl-4-trifluoromethyl- | 2-(6-carboethoxyhex-2-cis-enyl) | dl-16-hydroxy-9-oxo-16-trifluoromethyl- |
| | 4-trimethylsiloxy-1-decene | cyclopent-2-en-1-one | 20-ethyl-5-cis-13-trans prostadienoic acid |
| 73 | 1-trans-tri-n-butylstannyl-4-fluoromethyl- | 2-(7-carboethoxyhept-2-cis-enyl) | dl-16-hydroxy-9-oxo-16-fluoromethyl- |
| | 4-trimethylsiloxy-1-heptene | cyclopent-2-en-1-one | 20-nor-2-homo-5-cis-13-trans prostadienoic acid |
| 74 | 1-trans-tri-n-butylstannyl-4-difluoromethyl- | 2-(7-carboethoxyhept-2-cis-enyl) | dl-16-hydroxy-9-oxo-16-difluoromethyl- |
| | 4-trimethylsiloxy-1-heptene | cyclopent-2-en-1-one | 20-nor-2-homo-5-cis-13-trans prostadienoic acid |
| 75 | 1-trans-tri-n-butylstannyl-4-trifluoromethyl- | 2-(7-carboethoxyhept-2-cis-enyl) | dl-16-hydroxy-9-oxo-16-trifluoromethyl- |
| | 4-trimethylsiloxy-1-heptene | cyclopent-2-en-1-one | 20-nor-2-homo-5-cis-13-trans prostadienoic acid |
| 76 | 1-trans-tri-n-butylstannyl-4-fluoromethyl- | 2-(7-carboethoxyhept-2-cis-enyl) | dl-16-hydroxy-9-oxo-16-fluoromethyl- |
| | 4-trimethylsiloxy-1-octene | cyclopent-2-en-1-one | 2-homo-5-cis-13-trans prostadienoic acid |
| 77 | 1-trans-tri-n-butylstannyl-4-difluoromethyl- | 2-(7-carboethoxyhept-2-cis-enyl) | dl-16-hydroxy-9-oxo-16-difluoromethyl- |
| | 4-trimethylsiloxy-1-octene | cyclopent-2-en-1-one | 2-homo-5-cis-13-trans prostadienoic acid |
| 78 | 1-trans-tri-n-butylstannyl-4-trifluoromethyl- | 2-(7-carboethoxyhept-2-cis-enyl) | dl-16-hydroxy-9-oxo-16-trifluoromethyl- |
| | 4-trimethylsiloxy-1-octene | cyclopent-2-en-1-one | 2-homo-5-cis-13-trans prostadienoic acid |

| | -continued | |
|---|---|---|
| 79 | 1-trans-tri-n-butylstannyl-4-fluoromethyl-4-trimethylsiloxy-1-nonene | 2-(7-carboethoxyhept-2-cis-enyl)cyclopent-2-en-1-one | dl-16-hydroxy-9-oxo-16-fluoromethyl-20-methyl-2-homo-5-cis-13-trans prostadienoic acid |
| 80 | 1-trans-tri-n-butylstannyl-4-difluoromethyl-4-trimethylsiloxy-1-nonene | 2-(7-carboethoxyhept-2-cis-enyl)cyclopent-2-en-1-one | dl-16-hydroxy-9-oxo-16-difluoromethyl-20-methyl-2-homo-5-cis-13-trans prostadienoic acid |
| 81 | 1-trans-tri-n-butylstannyl-4-trifluoromethyl-4-trimethylsiloxy-1-nonene | 2-(7-carboethoxyhept-2-cis-enyl)cyclopent-2-en-1-one | dl-16-hydroxy-9-oxo-16-trifluoromethyl-20-methyl-2-homo-5-cis-13-trans prostadienoic acid |
| 82 | 1-trans-tri-n-butylstannyl-4-fluoromethyl-4-trimethylsiloxy-1-decene | 2-(7-carboethoxyhept-2-cis-enyl)cyclopent-2-en-1-one | dl-16-hydroxy-9-oxo-16-fluoromethyl-20-ethyl-2-homo-5-cis-13-trans prostadienoic acid |
| 83 | 1-trans-tri-n-butylstannyl-4-difluoromethyl-4-trimethylsiloxy-1-decene | 2-(7-carboethoxyhept-2-cis-enyl)cyclopent-2-en-1-one | dl-16-hydroxy-9-oxo-16-difluoromethyl-20-ethyl-2-homo-5-cis-13-trans prostadienoic acid |
| 84 | 1-trans-tri-n-butylstannyl-4-trifluoromethyl-4-trimethylsiloxy-1-decene | 2-(7-carboethoxyhept-2-cis-enyl)cyclopent-2-en-1-one | dl-16-hydroxy-9-oxo-16-trifluoromethyl-20-ethyl-2-homo-5-cis-13-trans prostadienoic acid |

TABLE II (continued)

Treatment of the PGE₂ derivatives of Examples 1–84 of Table II with lithium perhydro-9b-boraphenalyl hydride by the procedure of Reference Example 20 is productive of the PFG₂α derivatives of Examples of Table II.

| EXAMPLE | STARTING PROSTAGLANDIN OF THE PGE SERIES | PRODUCT PROSTAGLANDIN OF THE PGF₂α SERIES |
|---|---|---|
| 85 | dl-11α,16-dihydroxy-9-oxo-16-fluoromethyl-20-nor-2-nor-5-cis-13-trans prostadienoic acid | dl-9α,11α,16-trihydroxy-16-fluoromethyl-20-nor-2-nor-5-cis-13-trans prostadienoic acid |
| 86 | dl-11α,16-dihydroxy-9-oxo-16-difluoromethyl-20-nor-2-nor-5-cis-13-trans prostadienoic acid | dl-9α,11α,16-trihydroxy-16-difluoromethyl-20-nor-2-nor-5-cis-13-trans prostadienoic acid |
| 87 | dl-11α,16-dihydroxy-9-oxo-16-trifluoromethyl-20-nor-2-nor-5-cis-13-trans prostadienoic acid | dl-9α,11α,16-trihydroxy-16-trifluoromethyl-20-nor-2-nor-5-cis-13-trans prostadienoic acid |
| 88 | dl-11α,16-dihydroxy-9-oxo-16-fluoromethyl-2-nor-5-cis-13-trans prostadienoic acid | dl-9α,11α,16-trihydroxy-16-fluoromethyl-2-nor-5-cis-13-trans prostadienoic acid |
| 89 | dl-11α,16-dihydroxy-9-oxo-16-difluoromethyl-2-nor-5-cis-13-trans prostadienoic acid | dl-9α,11α,16-trihydroxy-16-difluoromethyl-2-nor-5-cis-13-trans prostadienoic acid |
| 90 | dl-11α,16-dihydroxy-9-oxo-16-trifluoromethyl-2-nor-5-cis-13-trans prostadienoic acid | dl-9α,11α,16-trihydroxy-16-trifluoromethyl-2-nor-5-cis-13-trans prostadienoic acid |
| 91 | dl-11α,16-dihydroxy-9-oxo-16-fluoromethyl-20-methyl-2-nor-5-cis-13-trans prostadienoic acid | dl-9α,11α,16-trihydroxy-16-fluoromethyl-20-methyl-2-nor-5-cis-13-trans prostadienoic acid |
| 92 | dl-11α,16-dihydroxy-9-oxo-16-difluoromethyl-20-methyl-2-nor-5-cis-13-trans prostadienoic acid | dl-9α,11α,16-trihydroxy-16-difluoromethyl-20-methyl-2-nor-5-cis-13-trans prostadienoic acid |
| 93 | dl-11α,16-dihydroxy-9-oxo-16-trifluoromethyl-20-methyl-2-nor-5-cis-13-trans prostadienoic acid | dl-9α,11α,16-trihydroxy-16-trifluoromethyl-20-methyl-2-nor-5-cis-13-trans prostadienoic acid |
| 94 | dl-11α,16-dihydroxy-9-oxo-16-fluoromethyl-20-ethyl-2-nor-5-cis-13-trans prostadienoic acid | dl-9α,11α,16-trihydroxy-16-fluoromethyl-20-ethyl-2-nor-5-cis-13-trans prostadienoic acid |
| 95 | dl-11α,16-dihydroxy-9-oxo-16-difluoromethyl-20-ethyl-2-nor-5-cis-13-trans prostadienoic acid | dl-9α,11α,16-trihydroxy-16-difluoromethyl-20-ethyl-2-nor-5-cis-13-trans prostadienoic acid |
| 96 | dl-11α,16-dihydroxy-9-oxo-16-trifluoromethyl-20-ethyl-2-nor-5-cis-13-trans prostadienoic acid | dl-9α,11α,16-trihydroxy-16-trifluoromethyl-20-ethyl-2-nor-5-cis-13-trans prostadienoic acid |
| 97 | dl-11α,16-dihydroxy-9-oxo-16-fluoromethyl-20-nor-5-cis-13-trans prostadienoic acid | dl-9α,11α,16-trihydroxy-16-fluoromethyl-20-nor-5-cis-13-trans prostadienoic acid |
| 98 | dl-11α,16-dihydroxy-9-oxo-16-difluoromethyl-20-nor-5-cis-13-trans prostadienoic acid | dl-9α,11α,16-trihydroxy-16-difluoromethyl-20-nor-5-cis-13-trans prostadienoic acid |
| 99 | dl-11α,16-dihydroxy-9-oxo-16-trifluoromethyl-20-nor-5-cis-13-trans prostadienoic acid | dl-9α,11α,16-trihydroxy-16-trifluoromethyl-20-nor-5-cis-13-trans prostadienoic acid |
| 100 | dl-11α,16-dihydroxy-9-oxo-16-fluoromethyl-5-cis-13-trans prostadienoic acid | dl-9α,11α,16-trihydroxy-16-fluoromethyl-5-cis-13-trans prostadienoic acid |
| 101 | dl-11α,16-dihydroxy-9-oxo-16-difluoromethyl-5-cis-13-trans prostadienoic acid | dl-9α,11α,16-trihydroxy-16-difluoromethyl-5-cis-13-trans prostadienoic acid |
| 102 | dl-11α,16-dihydroxy-9-oxo-16-trifluoromethyl-5-cis-13-trans prostadienoic acid | dl-9α,11α,16-trihydroxy-16-trifluoromethyl-5-cis-13-trans prostadienoic acid |
| 103 | dl-11α,16-dihydroxy-9-oxo-16-fluoromethyl-20-methyl-5-cis-13-trans prostadienoic acid | dl-9α,11α,16-trihydroxy-16-fluoromethyl-20-methyl-5-cis-13-trans prostadienoic acid |
| 104 | dl-11α,16-dihydroxy-9-oxo-16-difluoromethyl-20-methyl-5-cis-13-trans prostadienoic acid | dl-9α,11α,16-trihydroxy-16-difluoromethyl-20-methyl-5-cis-13-trans prostadienoic acid |
| 105 | dl-11α,16-dihydroxy-9-oxo-16-trifluoromethyl-20-methyl-5-cis-13-trans prostadienoic acid | dl-9α,11α,16-trihydroxy-16-trifluoromethyl-20-methyl-5-cis-13-trans prostadienoic acid |
| 106 | dl-11α,16-dihydroxy-9-oxo-16-fluoromethyl-20-ethyl-5-cis-13-trans prostadienoic acid | dl-9α,11α,16-trihydroxy-16-fluoromethyl-20-ethyl-5-cis-13-trans prostadienoic acid |
| 107 | dl-11α,16-dihydroxy-9-oxo-16-difluoromethyl-20-ethyl-5-cis-13-trans prostadienoic acid | dl-9α,11α,16-trihydroxy-16-difluoromethyl-20-ethyl-5-cis-13-trans prostadienoic acid |
| 108 | dl-11α,16-dihydroxy-9-oxo-16-trifluoromethyl-20-ethyl-5-cis-13-trans prostadienoic acid | dl-9α,11α,16-trihydroxy-16-trifluoromethyl-20-ethyl-5-cis-13-trans prostadienoic acid |
| 109 | dl-11α,16-dihydroxy-9-oxo-16-fluoromethyl-20-nor-2-homo-5-cis-13-trans prostadienoic acid | dl-9α,11α,16-trihydroxy-16-fluoromethyl-20-nor-2-homo-5-cis-13-trans prostadienoic acid |
| 110 | dl-11α,16-dihydroxy-9-oxo-16-difluoromethyl-20-nor-2-homo-5-cis-13-trans prostadienoic acid | dl-9α,11α,16-trihydroxy-16-difluoromethyl-20-nor-2-homo-5-cis-13-trans prostadienoic acid |
| 111 | dl-11α,16-dihydroxy-9-oxo-16-trifluoromethyl-20-nor-2-homo-5-cis-13-trans prostadienoic acid | dl-9α,11α,16-trihydroxy-16-trifluoromethyl-20-nor-2-homo-5-cis-13-trans prostadienoic acid |
| 112 | dl-11α,16-dihydroxy-9-oxo-16-fluoromethyl-2-homo-5-cis-13-trans prostadienoic acid | dl-9α,11α,16-trihydroxy-16-fluoromethyl-2-homo-5-cis-13-trans prostadienoic acid |
| 113 | dl-11α,16-dihydroxy-9-oxo-16-difluoromethyl-2-homo-5-cis-13-trans prostadienoic acid | dl-9α,11α,16-trihydroxy-16-difluoromethyl-2-homo-5-cis-13-trans prostadienoic acid |
| 114 | dl-11α,16-dihydroxy-9-oxo-16-trifluoromethyl-2-homo-5-cis-13-trans prostadienoic acid | dl-9α,11α,16-trihydroxy-16-trifluoromethyl-2-homo-5-cis-13-trans prostadienoic acid |
| 115 | dl-11α,16-dihydroxy-9-oxo-16-fluoromethyl-20-methyl-2-homo-5-cis-13-trans prostadienoic acid | dl-9α,11α,16-trihydroxy-16-fluoromethyl-20-methyl-2-homo-5-cis-13-trans prostadienoic acid |
| 116 | dl-11α,16-dihydroxy-9-oxo-16-difluoromethyl-20-methyl-2-homo-5-cis-13-trans prostadienoic acid | dl-9α,11α,16-trihydroxy-16-difluoromethyl-20-methyl-2-homo-5-cis-13-trans prostadienoic acid |
| 117 | dl-11α,16-dihydroxy-9-oxo-16-trifluoromethyl-20-methyl-2-homo-5-cis-13-trans prostadienoic acid | dl-9α,11α,16-trihydroxy-16-trifluoromethyl-20-methyl-2-homo-5-cis-13-trans prostadienoic acid |
| 118 | dl-11α,16-dihydroxy-9-oxo-16-fluoromethyl-20-ethyl-2-homo-5-cis-13-trans prostadienoic acid | dl-9α,11α,16-trihydroxy-16-fluoromethyl-20-ethyl-2-homo-5-cis-13-trans prostadienoic acid |
| 119 | dl-11α,16-dihydroxy-9-oxo-16-difluoromethyl-20-ethyl-2-homo-5-cis-13-trans prostadienoic acid | dl-9α,11α,16-trihydroxy-16-difluoromethyl-20-ethyl-2-homo-5-cis-13-trans prostadienoic acid |
| 120 | dl-11α,16-dihydroxy-9-oxo-16-trifluoromethyl-20-ethyl-2-homo-5-cis-13-trans prostadienoic acid | dl-9α,11α,16-trihydroxy-16-trifluoromethyl-20-ethyl-2-homo-5-cis-13-trans prostadienoic acid |
| 121 | nat-11α,16-dihydroxy-9-oxo-16-fluoromethyl-20-nor-5-cis-13-trans prostadienoic acid | nat-9α,11α,16-trihydroxy-16-fluoromethyl-20-nor-5-cis-13-trans prostadienoic acid |
| 122 | nat-11α,16-dihydroxy-9-oxo-16-difluoromethyl- | nat-9α,11α,16-trihydroxy-16-difluoromethyl- |

| | | |
|---|---|---|
| | 20-nor-5-cis-13-trans prostadienoic acid | 20-nor-5-cis-13-trans prostadienoic acid |
| 123 | nat-11α,16-dihydroxy-9-oxo-16-trifluoromethyl-20-nor-5-cis-13-trans prostadienoic acid | nat-9α,11α,16-trihydroxy-16-trifluoromethyl-20-nor-5-cis-13-trans prostadienoic acid |
| 124 | nat-11α,16-dihydroxy-9-oxo-16-fluoromethyl-5-cis-13-trans prostadienoic acid | nat-9α,11α,16-trihydroxy-16-fluoromethyl-5-cis-13-trans prostadienoic acid |
| 125 | nat-11α,16-dihydroxy-9-oxo-16-difluoromethyl-5-cis-13-trans prostadienoic acid | nat-9α,11α,16-trihydroxy-16-difluoromethyl-5-cis-13-trans prostadienoic acid |
| 126 | nat-11α,16-dihydroxy-9-oxo-16-trifluoromethyl-5-cis-13-trans prostadienoic acid | nat-9α,11α,16-trihydroxy-16-trifluoromethyl-5-cis-13-trans prostadienoic acid |
| 127 | nat-11α,16-dihydroxy-9-oxo-16-fluoromethyl-20-methyl-5-cis-13-trans prostadienoic acid | nat-9α,11α,16-trihydroxy-16-fluoromethyl-20-methyl-5-cis-13-trans prostadienoic acid |
| 128 | nat-11α,16-dihydroxy-9-oxo-16-difluoromethyl-20-methyl-5-cis-13-trans prostadienoic acid | nat-9α,11α-trihydroxy-16-difluoromethyl-20-methyl-5-cis-13-trans prostadienoic acid |
| 129 | nat-11α,16-dihydroxy-9-oxo-16-trifluoromethyl-20-methyl-5-cis-13-trans prostadienoic acid | nat-9α,11α,16-trihydroxy-16-trifluoromethyl-20-methyl-5-cis-13-trans prostadienoic acid |
| 130 | nat-11α,16-dihydroxy-9-oxo-16-fluoromethyl-20-ethyl-5-cis-13-trans prostadienoic acid | nat-9α,11α,16-trihydroxy-16-fluoromethyl-20-ethyl-5-cis-13-trans prostadienoic acid |
| 131 | nat-11α,16-dihydroxy-9-oxo-16-difluoromethyl-20-ethyl-5-cis-13-trans prostadienoic acid | nat-9α,11α,16-trihydroxy-16-difluoromethyl-20-ethyl-5-cis-13-trans prostadienoic acid |
| 132 | nat-11α,16-dihydroxy-9-oxo-16-trifluoromethyl-20-ethyl-5-cis-13-trans prostadienoic acid | nat-9α,11α,16-trihydroxy-16-trifluoromethyl-20-ethyl-5-cis-13-trans prostadienoic acid |
| 133 | dl-16-hydroxy-9-oxo-16-fluoromethyl-20-nor-2-nor-5-cis-13-trans prostadienoic acid | dl-9α,16-dihydroxy-16-fluoromethyl-20-nor-2-nor-5-cis-13-trans prostadienoic acid |
| 134 | dl-16-hydroxy-9-oxo-16-difluoromethyl-20-nor-2-nor-5-cis-13-trans prostadienoic acid | dl-9α,16-dihydroxy-16-difluoromethyl-20-nor-2-nor-5-cis-13-trans prostadienoic acid |
| 135 | dl-16-hydroxy-9-oxo-16-trifluoromethyl-20-nor-2-nor-5-cis-13-trans prostadienoic acid | dl-9α,16-dihydroxy-16-trifluoromethyl-20-nor-2-nor-5-cis-13-trans prostadienoic acid |
| 136 | dl-16-hydroxy-9-oxo-16-fluoromethyl-2-nor-5-cis-13-trans prostadienoic acid | dl-9α,16-dihydroxy-16-fluoromethyl-2-nor-5-cis-13-trans prostadienoic acid |
| 137 | dl-16-hydroxy-9-oxo-16-difluoromethyl-2-nor-5-cis-13-trans prostadienoic acid | dl-9α,16-dihydroxy-16-difluoromethyl-2-nor-5-cis-13-trans prostadienoic acid |
| 138 | dl-16-hydroxy-9-oxo-16-trifluoromethyl-2-nor-5-cis-13-trans prostadienoic acid | dl-9α,16-dihydroxy-16-trifluoromethyl-2-nor-5-cis-13-trans prostadienoic acid |
| 139 | dl-16-hydroxy-9-oxo-16-fluoromethyl-20-methyl-2-nor-5-cis-13-trans prostadienoic acid | dl-9α,16-dihydroxy-16-fluoromethyl-20-methyl-2-nor-5-cis-13-trans prostadienoic acid |
| 140 | dl-16-hydroxy-9-oxo-16-difluoromethyl-20-methyl-2-nor-5-cis-13-trans prostadienoic acid | dl-9α,16-dihydroxy-16-difluoromethyl-20-methyl-2-nor-5-cis-13-trans prostadienoic acid |
| 141 | dl-16-hydroxy-9-oxo-16-trifluoromethyl-20-methyl-2-nor-5-cis-13-trans prostadienoic acid | dl-9α,16-dihydroxy-16-trifluoromethyl-20-methyl-2-nor-5-cis-13-trans prostadienoic acid |
| 142 | dl-16-hydroxy-9-oxo-16-fluoromethyl-20-ethyl-2-nor-5-cis-13-trans prostadienoic acid | dl-9α,16-dihydroxy-16-fluoromethyl-20-ethyl-2-nor-5-cis-13-trans prostadienoic acid |
| 143 | dl-16-hydroxy-9-oxo-16-difluoromethyl-20-ethyl-2-nor-5-cis-13-trans prostadienoic acid | dl-9α,16-dihydroxy-16-difluoromethyl-20-ethyl-2-nor-5-cis-13-trans prostadienoic acid |
| 144 | dl-16-hydroxy-9-oxo-16-trifluoromethyl-20-ethyl-2-nor-5-cis-13-trans prostadienoic acid | dl-9α,16-dihydroxy-16-trifluoromethyl-20-ethyl-2-nor-5-cis-13-trans prostadienoic acid |
| 145 | dl-16-hydroxy-9-oxo-16-fluoromethyl-20-nor-5-cis-13-trans prostadienoic acid | dl-9α,16-dihydroxy-16-fluoromethyl-20-nor-5-cis-13-trans prostadienoic acid |
| 146 | dl-16-hydroxy-9-oxo-16-difluoromethyl-20-nor-5-cis-13-trans prostadienoic acid | dl-9α,16-dihydroxy-16-difluoromethyl-20-nor-5-cis-13-trans prostadienoic acid |
| 147 | dl-16-hydroxy-9-oxo-16-trifluoromethyl-20-nor-5-cis-13-trans prostadienoic acid | dl-9α,16-dihydroxy-16-trifluoromethyl-20-nor-5-cis-13-trans prostadienoic acid |
| 148 | dl-16-hydroxy-9-oxo-16-fluoromethyl-5-cis-13-trans prostadienoic acid | dl-9α,16-dihydroxy-16-fluoromethyl-5-cis-13-trans prostadienoic acid |
| 149 | dl-16-hydroxy-9-oxo-16-difluoromethyl-5-cis-13-trans prostadienoic acid | dl-9α,16-dihydroxy-16-difluoromethyl-5-cis-13-trans prostadienoic acid |
| 150 | dl-16-hydroxy-9-oxo-16-trifluoromethyl-5-cis-13-trans prostadienoic acid | dl-9α,16-dihydroxy-16-trifluoromethyl-5-cis-13-trans prostadienoic acid |
| 151 | dl-16-hydroxy-9-oxo-16-fluoromethyl-20-methyl-5-cis-13-trans prostadienoic acid | dl-9α,16-dihydroxy-16-fluoromethyl-20-methyl-5-cis-13-trans prostadienoic acid |
| 152 | dl-16-hydroxy-9-oxo-16-difluoromethyl-20-methyl-5-cis-13-trans prostadienoic acid | dl-9α,16-dihydroxy-16-difluoromethyl-20-methyl-5-cis-13-trans prostadienoic acid |
| 153 | dl-16-hydroxy-9-oxo-16-trifluoromethyl-20-methyl-5-cis-13-trans prostadienoic acid | dl-9α,16-dihydroxy-16-trifluoromethyl-20-methyl-5-cis-13-trans prostadienoic acid |
| 154 | dl-16-hydroxy-9-oxo-16-fluoromethyl-20-ethyl-5-cis-13-trans prostadienoic acid | dl-9α,16-dihydroxy-16-fluoromethyl-20-ethyl-5-cis-13-trans prostadienoic acid |
| 155 | dl-16-hydroxy-9-oxo-16-difluoromethyl-20-ethyl-5-cis-13-trans prostadienoic acid | dl-9α,16-dihydroxy-16-difluoromethyl-20-ethyl-5-cis-13-trans prostadienoic acid |
| 156 | dl-16-hydroxy-9-oxo-16-trifluoromethyl-20-ethyl-5-cis-13-trans prostadienoic acid | dl-9α,16-dihydroxy-16-trifluoromethyl-20-ethyl-5-cis-13-trans prostadienoic acid |
| 157 | dl-16-hydroxy-9-oxo-16-fluoromethyl-20-nor-2-homo-5-cis-13-trans prostadienoic acid | dl-9α,16-dihydroxy-16-fluoromethyl-20-nor-2-homo-5-cis-13-trans prostadienoic acid |
| 158 | dl-16-hydroxy-9-oxo-16-difluoromethyl-20-nor-2-homo-5-cis-13-trans prostadienoic acid | dl-9α,16-dihydroxy-16-difluoromethyl-20-nor-2-homo-5-cis-13-trans prostadienoic acid |
| 159 | dl-16-hydroxy-9-oxo-16-trifluoromethyl-20-nor-2-homo-5-cis-13-trans prostadienoic acid | dl-9α,16-dihydroxy-16-trifluoromethyl-20-nor-2-homo-5-cis-13-trans prostadienoic acid |
| 160 | dl-16-hydroxy-9-oxo-16-fluoromethyl-2-homo-5-cis-13-trans prostadienoic acid | dl-9α,16-dihydroxy-16-fluoromethyl-2-homo-5-cis-13-trans prostadienoic acid |
| 161 | dl-16-hydroxy-9-oxo-16-difluoromethyl-2-homo-5-cis-13-trans prostadienoic acid | dl-9α,16-dihydroxy-16-difluoromethyl-2-homo-5-cis-13-trans prostadienoic acid |

-continued

| | | |
|---|---|---|
| 162 | dl-16-hydroxy-9-oxo-16-trifluoromethyl-2-homo-5-cis-13-trans prostadienoic acid | dl-9α,16-dihydroxy-16-trifluoromethyl-2-homo-5-cis-13-trans prostadienoic acid |
| 163 | dl-16-hydroxy-9-oxo-16-fluoromethyl-20-methyl-2-homo-5-cis-13-trans prostadienoic acid | dl-9-α,16-dihydroxy-16-fluoromethyl-20-methyl-2-homo-5-cis-13-trans prostadienoic acid |
| 164 | dl-16-hydroxy-9-oxo-16-difluoromethyl-20-methyl-2-homo-5-cis-13-trans prostadienoic acid | dl-9α,16-dihydroxy-16-difluoromethyl-20-methyl-2-homo-5-cis-13-trans prostadienoic acid |
| 165 | dl-16-hydroxy-9-oxo-16-trifluoromethyl-20-methyl-2-homo-5-cis-13-trans prostadienoic acid | dl-9α,16-dihydroxy-16-trifluoromethyl-20-methyl-2-homo-5-cis-13-trans prostadienoic acid |
| 166 | dl-16-hydroxy-9-oxo-16-fluoromethyl-20-ethyl-2-homo-5-cis-13-trans prostadienoic acid | dl-9α,16-dihydroxy-16-fluoromethyl-20-ethyl-2-homo-5-cis-13-trans prostadienoic acid |
| 167 | dl-16-hydroxy-9-oxo-16-difluoromethyl-20-ethyl-2-homo-5-cis-13-trans prostadienoic acid | dl-9α,16-dihydroxy-16-difluoromethyl-20-ethyl-2-homo-5-cis-13-trans prostadienoic acid |
| 168 | dl-16-hydroxy-9-oxo-16-trifluoromethyl-20-ethyl-2-homo-5-cis-13-trans prostadienoic acid | dl-9α,16-dihydroxy-16-trifluoromethyl-20-ethyl-2-homo-5-cis-13-trans prostadienoic acid |

TABLE II (Continued)

Treatment of the PGE$_2$ derivatives of Examples 1 to 84 of Table II with sodium borohydride by the procedure of Reference Example 21 is productive of the PGF$_\alpha$ and PGF$_\beta$ derivatives of Examples 169 to 252 of Table II.

| EXAMPLE | STARTING PROSTAGLANDIN OF THE PGE SERIES | PRODUCT PROSTAGLANDIN OF THE PGF$_{2\beta}$ SERIES |
|---|---|---|
| 169 | dl-11α,16-dihydroxy-9-oxo-16-fluoromethyl-20-nor-2-nor-5-cis-13-trans prostadienoic acid | dl-9β,11α,16-trihydroxy-16-fluoromethyl-20-nor-2-nor-5-cis-13-trans prostadienoic acid |
| 170 | dl-11α,16-dihydroxy-9-oxo-16-difluoromethyl-20-nor-2-nor-5-cis-13-trans prostadienoic acid | dl-9β,11α,16-trihydroxy-16-difluoromethyl-20-nor-2-nor-5-cis-13-trans prostadienoic acid |
| 171 | dl-11α,16-dihydroxy-9-oxo-16-trifluromethyl-20-nor-2-nor-5-cis-13-trans prostadienoic acid | dl-9β,11α,16-trihydroxy-16-trifluoromethyl-20-nor-2-nor-5-cis-13-trans prostadienoic acid |
| 172 | dl-11α,16-dihydroxy-9-oxo-16-fluoromethyl-2-nor-5-cis-13-trans prostadienoic acid | dl-9β,11α,16-trihydroxy-16-fluoromethyl-2-nor-5-cis-13-trans prostadienoic acid |
| 173 | dl-11α,16-dihydroxy-9-oxo-16-difluoromethyl-2-nor-5-cis-13-trans prostadienoic acid | dl-9β,11α,16-trihydroxy-16-difluoromethyl-2-nor-5-cis-13-trans prostadienoic acid |
| 174 | dl-11α,16-dihydroxy-9-oxo-16-trifluoromethyl-2-nor-5-cis-13-trans prostadienoic acid | dl-9β,11α,16-trihydroxy-16-trifluoromethyl-2-nor-5-cis-13-trans prostadienoic acid |
| 175 | dl-11α,16-dihydroxy-9-oxo-16-fluoromethyl-20-methyl-2-nor-5-cis-13-trans prostadienoic acid | dl-9β,11α,16-trihydroxy-16-fluoromethyl-20-methyl-2-nor-5-cis-13-trans prostadienoic acid |
| 176 | dl-11α,16-dihydroxy-9-oxo-16-difluoromethyl-20-methyl-2-nor-5-cis-13-trans prostadienoic acid | dl-9β,11α,16-trihydroxy-16-difluoromethyl-20-methyl-2-nor-5-cis-13-trans prostadienoic acid |
| 177 | dl-11α,16-dihydroxy-9-oxo-16-trifluoromethyl-20-methyl-2-nor-5-cis-13-trans prostadienoic acid | dl-9β,11α,16-trihydroxy-16-trifluoromethyl-20-methyl-2-nor-5-cis-13-trans prostadienoic acid |
| 178 | dl-11α,16-dihydroxy-9-oxo-16-fluoromethyl-20-ethyl-2-nor-5-cis-13-trans prostadienoic acid | dl-9β,11α,16-trihydroxy-16-fluoromethyl-20-ethyl-2-nor-5-cis-13-trans prostadienoic acid |
| 179 | dl-11α,16-dihydroxy-9-oxo-16-difluoromethyl-20-ethyl-2-nor-5-cis-13-trans prostadienoic acid | dl-9β,11α,16-trihydroxy-16-difluoromethyl-20-ethyl-2-nor-5-cis-13-trans prostadienoic acid |
| 180 | dl-11α,16-dihydroxy-9-oxo-16-trifluoromethyl-20-ethyl-2-nor-5-cis-13-trans prostadienoic acid | dl-9β,11α,16-trihydroxy-16-trifluoromethyl-20-ethyl-2-nor-5-cis-13-trans prostadienoic acid |
| 181 | dl-11α,16-dihydroxy-9-oxo-16-fluoromethyl-20-nor-5-cis-13-trans prostadienoic acid | dl-9β,11α,16-trihydroxy-16-fluoromethyl-20-nor-5-cis-13-trans prostadienoic acid |
| 182 | dl-11α,16-dihydroxy-9-oxo-16-difluoromethyl-20-nor-5-cis-13-trans prostadienoic acid | dl-9β,11α,16-trihydroxy-16-difluoromethyl-20-nor-5-cis-13-trans prostadienoic acid |
| 183 | dl-11α,16-dihydroxy-9-oxo-16-trifluoromethyl-20-nor-5-cis-13-trans prostadienoic acid | dl-9β,11α,16-trihydroxy-16-trifluoromethyl-20-nor-5-cis-13-trans prostadienoic acid |
| 184 | dl-11α,16-dihydroxy-9-oxo-16-fluoromethyl-5-cis-13-trans prostadienoic acid | dl-9β,11α,16-trihydroxy-16-fluoromethyl-5-cis-13-trans prostadienoic acid |
| 185 | dl-11α,16-dihydroxy-9-oxo-16-difluoromethyl-5-cis-13-trans prostadienoic acid | dl-9β,11α,16-trihydroxy-16-difluoromethyl-5-cis-13-trans prostadienoic acid |
| 186 | dl-11α,16-dihydroxy-9-oxo-16-trifluoromethyl-5-cis-13-trans prostadienoic acid | dl-9β,11α,16-trihydroxy-16-trifluoromethyl-5-cis-13-trans prostadienoic acid |
| 187 | dl-11α,16-dihydroxy-9-oxo-16-fluoromethyl-20-methyl-5-cis-13-trans prostadienoic acid | dl-9β,11α,16-trihydroxy-16-fluoromethyl-20-methyl-5-cis-13-trans prostadienoic acid |
| 188 | dl-11α,16-dihydroxy-9-oxo-16-difluoromethyl-20-methyl-5-cis-13-trans prostadienoic acid | dl-9β,11α,16-trihydroxy-16-difluoromethyl-20-methyl-5-cis-13-trans prostadienoic acid |
| 189 | dl-11α,16-dihydroxy-9-oxo-16-trifluoromethyl-20-methyl-5-cis-13-trans prostadienoic acid | dl-9β,11α,16-trihydroxy-16-trifluoromethyl-20-methyl-5-cis-13-trans prostadienoic acid |
| 190 | dl-11α,16-dihydroxy-9-oxo-16-fluoromethyl-20-ethyl-5-cis-13-trans prostadienoic acid | dl-9β,11α,16-trihydroxy-16-fluoromethyl-20-ethyl-5-cis-13-trans prostadienoic acid |
| 191 | dl-11α,16-dihydroxy-9-oxo-16-difluoromethyl-20-ethyl-5-cis-13-trans prostadienoic acid | dl-9β,11α,16-trihydroxy-16-difluoromethyl-20-ethyl-5-cis-13-trans prostadienoic acid |
| 192 | dl-11α,16-dihydroxy-9-oxo-16-trifluoromethyl-20-ethyl-5-cis-13-trans prostadienoic acid | dl-9β,11α,16-trihydroxy-16-trifluoromethyl-20-ethyl-5-cis-13-trans prostadienoic acid |
| 193 | dl-11α,16-dihydroxy-9-oxo-16-fluoromethyl-20-nor-2-homo-5-cis-13-trans prostadienoic acid | dl-9β,11α,16-trihydroxy-16-fluoromethyl-20-nor-2-homo-5-cis-13-trans prostadienoic acid |
| 194 | dl-11α,16-dihydroxy-9-oxo-16-difluoromethyl-20-nor-2-homo-5-cis-13-trans prostadienoic acid | dl-9β,11α,16-trihydroxy-16-difluoromethyl-20-nor-2-homo-5-cis-13-trans prostadienoic acid |
| 195 | dl-11α,16-dihydroxy-9-oxo-16-trifluoromethyl-20-nor-2-homo-5-cis-13-trans prostadienoic acid | dl-9β,11α,16-trihydroxy-16-trifluoromethyl-20-nor-2-homo-5-cis-13-trans prostadienoic acid |
| 196 | dl-11α,16-dihydroxy-9-oxo-16-fluoromethyl-2-homo-5-cis-13-trans prostadienoic acid | dl-9β,11α,16-trihydroxy-16-fluoromethyl-2-homo-5-cis-13-trans prostadienoic acid |
| 197 | dl-11α,16-dihydroxy-9-oxo-16-difluoromethyl- | dl-9β,11α,16-trihydroxy-16-difluoromethyl- |

| # | | |
|---|---|---|
| | 2-homo-5-cis-13-trans prostadienoic acid | 2-homo-5-cis-13-trans prostadienoic acid |
| 198 | dl-11α,16-dihydroxy-9-oxo-16-trifluoromethyl-2-homo-5-cis-13-trans prostadienoic acid | dl-9β,11α,16-trihydroxy-16-trifluoromethyl-2-homo-5-cis-13-trans prostadienoic acid |
| 199 | dl-11α,16-dihydroxy-9-oxo-16-fluoromethyl-20-methyl-2-homo-5-cis-13-trans prostadienoic acid | dl-9β,11α,16-trihydroxy-16-fluoromethyl-20-methyl-2-homo-5-cis-13-trans prostadienoic acid |
| 200 | dl-11α,16-dihydroxy-9-oxo-16-difluoromethyl-20-methyl-2-homo-5-cis-13-trans prostadienoic acid | dl-9β,11α,16-trihydroxy-16-difluoromethyl-20-methyl-2-homo-5-cis-13-trans prostadienoic acid |
| 201 | dl-11α,16-dihydroxy-9-oxo-16-trifluoromethyl-20-methyl-2-homo-5-cis-13-trans prostadienoic acid | dl-9β11α,16-trihydroxy-16-trifluoromethyl-20-methyl-2-homo-5-cis-13-trans prostadienoic acid |
| 202 | dl-11α,16-dihydroxy-9-oxo-16-fluoromethyl-20-ethyl-2-homo-5-cis-13-trans prostadienoic acid | dl-9β,11α,16-trihydroxy-16-fluoromethyl-20-ethyl-2-homo-5-cis-13-trans prostadienoic acid |
| 203 | dl-11α,16-dihydroxy-9-oxo-16-difluoromethyl-20-ethyl-2-homo-5-cis-13-trans prostadienoic acid | dl-9β,11α,16-trihydroxy-16-difluoromethyl-20-ethyl-2-homo-5-cis-13-trans prostadienoic acid |
| 204 | dl-11α,16-dihydroxy-9-oxo-16-trifluoromethyl 20-ethyl-2-homo-5-cis-13-trans prostadienoic acid | dl-9β,11α,16-trihydroxy-16-trifluoromethyl-20-ethyl-2-homo-5-cis-13-trans prostadienoic acid |
| 205 | nat-11α,16-dihydroxy-9-oxo-16-fluoromethyl-20-nor-5-cis-13-trans prostadienoic acid | nat-9β,11α,16-trihydroxy-16-fluoromethyl-20-nor-5-cis-13-trans prostadienoic acid |
| 206 | nat-11α,16-dihydroxy-9-oxo-16-difluoromethyl-20-nor-5-cis-13-trans prostadienoic acid | nat-9β,11α,16-trihydroxy-16-difluoromethyl-20-nor-5-cis-13-trans prostadienoic acid |
| 207 | nat-11α,16-dihydroxy-9-oxo-16-trifluoromethyl-20-nor-5-cis-13-trans prostadienoic acid | nat-9β,11α16-trihydroxy-16-trifluoromethyl-20-nor-5-cis-13-trans prostadienoic acid |
| 208 | nat-11α,16-dihydroxy-9-oxo-16-fluoromethyl-5-cis-13-trans prostadienoic acid | nat-9β,11α,16-trihydroxy-16-fluoromethyl-5-cis-13-trans prostadienoic acid |
| 209 | nat-11α,16-dihydroxy-9-oxo-16-difluoromethyl-5-cis-13-trans prostadienoic acid | nat-9β,11α,16-trihydroxy-16-difluoromethyl-5-cis-13-trans prostadienoic acid |
| 210 | nat-11α,16-dihydroxy-9-oxo-16-trifluoromethyl-5-cis-13-trans prostadienoic acid | nat-9β,11α,16-trihydroxy-16-trifluoromethyl-5-cis-13-trans prostadienoic acid |
| 211 | nat-11α,16-dihydroxy-9-oxo-16-fluoromethyl-20-methyl-5-cis-13-trans prostadienoic acid | nat-9β,11α,16-trihydroxy-16-fluoromethyl-20-methyl-5-cis-13-trans prostadienoic acid |
| 212 | nat-11α,16-dihydroxy-9-oxo-16-difluoromethyl-20-methyl-5-cis-13-trans prostadienoic acid | nat-9β,11α,16-trihydroxy-16-difluoromethyl-20-methyl-5-cis-13-trans prostadienoic acid |
| 213 | nat-11α,16-dihydroxy-9-oxo-16-trifluoromethyl-20-methyl-5-cis-13-trans prostadienoic acid | nat-9β,11α,16-trihydroxy-16-trifluoromethyl-20-methyl-5-cis-13-trans prostadienoic acid |
| 214 | nat-11α,16-dihydroxy-9-oxo-16-fluoromethyl-20-ethyl-5-cis-13-trans prostadienoic acid | nat-9β,11α,16-trihydroxy-16-fluoromethyl-20-ethyl-5-cis-13-trans prostadienoic acid |
| 215 | nat-11α,16-dihydroxy-9-oxo-16-difluoromethyl-20-ethyl-5-cis-13-trans prostadienoic acid | nat-9β,11α,16-trihydroxy-16-difluoromethyl-20-ethyl-5-cis-13-trans prostadienoic acid |
| 216 | nat-11α,16-dihydroxy-9-oxo-16-trifluoromethyl-20-ethyl-5-cis-13-trans prostadienoic acid | nat-9β,11α,16-trihydroxy-16-trifluoromethyl-20-ethyl-5-cis-13-trans prostadienoic acid |
| 217 | dl-16-hydroxy-9-oxo-16-fluoromethyl-20-nor-2-nor-5-cis-13-trans prostadienoic acid | dl-9β,16-dihydroxy-16-fluoromethyl-20-nor-2-nor-5-cis-13-trans prostadienoic acid |
| 218 | dl-16-hydroxy-9-oxo-16-difluoromethyl-20-nor-2-nor-5-cis-13-trans prostadienoic acid | dl-9β,16-dihydroxy-16-difluoromethyl-20-nor-2-nor-5-cis-13-trans prostadienoic acid |
| 219 | dl-16-hydroxy-9-oxo-16-trifluoromethyl-20-nor-2-nor-5-cis-13-trans prostadienoic acid | dl-9β,16-dihydroxy-16-trifluoromethyl-20-nor-2-nor-5-cis-13-trans prostadienoic acid |
| 220 | dl-16-hydroxy-9-oxo-16-fluoromethyl-2-nor-5-cis-13-trans prostadienoic acid | dl-9β,16-dihydroxy-16-fluoromethyl-2-nor-5-cis-13-trans prostadienoic acid |
| 221 | dl-16-hydroxy-9-oxo-16-difluoromethyl-2-nor-5-cis-13-trans prostadienoic acid | dl-9β,16-dihydroxy-16-difluoromethyl-2-nor-5-cis-13-trans prostadienoic acid |
| 222 | dl-16-hydroxy-9-oxo-16-trifluoromethyl-2-nor-5-cis-13-trans prostadienoic acid | dl-9β,16-dihydroxy-16-trifluoromethyl-2-nor-5-cis-13-trans prostadienoic acid |
| 223 | dl-16-hydroxy-9-oxo-16-fluoromethyl-20-methyl-2-nor-5-cis-13-trans prostadienoic acid | dl-9β,16-dihydroxy-16-fluoromethyl-20-methyl-2-nor-5-cis-13-trans prostadienoic acid |
| 224 | dl-16-hydroxy-9-oxo-16-difluoromethyl-20-methyl-2-nor-5-cis-13-trans prostadienoic acid | dl-9β,16-dihydroxy-16-difluoromethyl-20-methyl-2-nor-5-cis-13-trans prostadienoic acid |
| 225 | dl-16-hydroxy-9-oxo-16-trifluoromethyl 20-methyl-2-nor-5-cis-13-trans prostadienoic acid | dl-9β,16-dihydroxy-16-trifluoromethyl-20-methyl-2-nor-5-cis-13-trans prostadienoic acid |
| 226 | dl-16-hydroxy-9-oxo-16-fluoromethyl-20-ethyl-2-nor-5-cis-13-trans prostadienoic acid | dl-9β,16-dihydroxy-16-fluoromethyl-20-ethyl-2-nor-5-cis-13-trans prostadienoic acid |
| 227 | dl-16-hydroxy-9-oxo-16-difluoromethyl-20-ethyl-2-nor-5-cis-13-trans prostadienoic acid | dl-9β,16-dihydroxy-16-difluoromethyl-20-ethyl-2-nor-5-cis-13-trans prostadienoic acid |
| 228 | dl-16-hydroxy-9-oxo-16-trifluoromethyl-20-ethyl-2-nor-5-cis-13-trans prostadienoic acid | dl-9β,16-dihydroxy-16-trifluoromethyl-20-ethyl-2-nor-5-cis-13-trans prostadienoic acid |
| 229 | dl-16-hydroxy-9-oxo-16-fluoromethyl-20-nor-5-cis-13-trans prostadienoic acid | dl-9β,16-dihydroxy-16-fluoromethyl-20-nor-5-cis-13-trans prostadienoic acid |
| 230 | dl-16-hydroxy-9-oxo-16-difluoromethyl-20-nor-5-cis-13-trans prostadienoic acid | dl-9β,16-dihydroxy-16-difluoromethyl-20-nor-5-cis-13-trans prostadienoic acid |
| 231 | dl-16-hydroxy-9-oxo-16-trifluoromethyl-20-nor-5-cis-13-trans prostadienoic acid | dl-9β,16-dihydroxy-16-trifluoromethyl-20-nor-5-cis-13-trans prostadienoic acid |
| 232 | dl-16-hydroxy-9-oxo-16-fluoromethyl-5-cis-13-trans prostadienoic acid | dl-9β,16-dihydroxy-16-fluoromethyl-5-cis-13-trans prostadienoic acid |
| 233 | dl-16-hydroxy-9-oxo-16-difluoromethyl-5-cis-13-trans prostadienoic acid | dl-9β,16-dihydroxy-16-difluoromethyl-5-cis-13-trans prostadienoic acid |
| 234 | dl-16-hydroxy-9-oxo-16-trifluoromethyl-5-cis-13-trans prostadienoic acid | dl-9β,16-dihydroxy-16-trifluoromethyl-5-cis-13-trans prostadienoic acid |
| 235 | dl-16-hydroxy-9-oxo-16-fluoromethyl-20-methyl-5-cis-13-trans prostadienoic acid | dl-9β,16-dihydroxy-16-fluoromethyl-20-methyl-5-cis-13-trans prostadienoic acid |
| 236 | dl-16-hydroxy-9-oxo-16-difluoromethyl-20-methyl-5-cis-13-trans prostadienoic acid | dl-9β,16-dihydroxy-16-difluoromethyl-20-methyl-5-cis-13-trans prostadienoic acid |

| | | |
|---|---|---|
| 237 | dl-16-hydroxy-9-oxo-16-trifluoromethyl-20-methyl-5-cis-13-trans prostadienoic acid | dl-9β,16-dihydroxy-16-trifluoromethyl-20-methyl-5-cis-13-trans prostadienoic acid |
| 238 | dl-16-hydroxy-9-oxo-16-fluoromethyl-20-ethyl-5-cis-13-trans prostadienoic acid | dl-9β,16-dihydroxy-16-fluoromethyl-20-ethyl-5-cis-13-trans prostadienoic acid |
| 239 | dl-16-hydroxy-9-oxo-16-difluoromethyl-20-ethyl-5-cis-13-trans prostadienoic acid | dl-9β,16-dihydroxy-16-difluoromethyl-20-ethyl-5-cis-13-trans prostadienoic acid |
| 240 | dl-16-hydroxy-9-oxo-16-trifluoromethyl-20-ethyl-5-cis-13-trans prostadienoic acid | dl-9β,16-dihydroxy-16-trifluoromethyl-20-ethyl-5-cis-13-trans prostadienoic acid |
| 241 | dl-16-hydroxy-9-oxo-16-fluoromethyl-20-nor-2-homo-5-cis-13-trans prostadienoic acid | dl-9β,16-dihydroxy-16-fluoromethyl-20-nor-2-homo-5-cis-13-trans prostadienoic acid |
| 242 | dl-16-hydroxy-9-oxo-16-difluoromethyl-20-nor-2-homo-5-cis-13-trans prostadienoic acid | dl-9β,16-dihydroxy-16-difluoromethyl-20-nor-2-homo-5-cis-13-trans prostadienoic acid |
| 243 | dl-16-hydroxy-9-oxo-16-trifluoromethyl-20-nor-2-homo-5-cis-13-trans prostadienoic acid | dl-9β,16-dihydroxy-16-trifluoromethyl-20-nor-2-homo-5-cis-13-trans prostadienoic acid |
| 244 | dl-16-hydroxy-9-oxo-16-fluoromethyl-2-homo-5-cis-13-trans prostadienoic acid | dl-9β,16-dihydroxy-16-fluoromethyl-2-homo-5-cis-13-trans prostadienoic acid |
| 245 | dl-16-hydroxy-9-oxo-16-difluoromethyl-2-homo-5-cis-13-trans prostadienoic acid | dl-9β,16-dihydroxy-16-difluoromethyl-2-homo-5-cis-13-trans prostadienoic acid |
| 246 | dl-16-hydroxy-9-oxo-16-trifluoromethyl-2-homo-5-cis-13-trans prostadienoic acid | dl-9β,16-dihydroxy-16-trifluoromethyl-2-homo-5-cis-13-trans prostadienoic acid |
| 247 | dl-16-hydroxy-9-oxo-16-fluoromethyl-20-methyl-2-homo-5-cis-13-trans prostadienoic acid | dl-9β,16-dihydroxy-16-fluoromethyl-20-methyl-2-homo-5-cis-13-trans prostadienoic acid |
| 248 | dl-16-hydroxy-9-oxo-16-difluoromethyl-20-methyl-2-homo-5-cis-13-trans prostadienoic acid | dl-9β,16-dihydroxy-16-difluoromethyl-20-methyl-2-homo-5-cis-13-trans prostadienoic acid |
| 249 | dl-16-hydroxy-9-oxo-16-trifluoromethyl-20-methyl-2-homo-5-cis-13-trans prostadienoic acid | dl-9β,16-dihydroxy-16-trifluoromethyl-20-methyl-2-homo-5-cis-13-trans prostadienoic acid |
| 250 | dl-16-hydroxy-9-oxo-16-fluoromethyl-20-ethyl-2-homo-5-cis-13-trans prostadienoic acid | dl-9β,16-dihydroxy-16-fluoromethyl-20-ethyl-2-homo-5-cis-13-trans prostadienoic acid |
| 251 | dl-16-hydroxy-9-oxo-16-difluoromethyl-20-ethyl-2-homo-5-cis-13-trans prostadienoic acid | dl-9β,16-dihydroxy-16-difluoromethyl-20-ethyl-2-homo-5-cis-13-trans prostadienoic acid |
| 252 | dl-16-hydroxy-9-oxo-16-trifluoromethyl-20-ethyl-2-homo-5-cis-13-trans prostadienoic acid | dl-9β,16-dihydroxy-16-trifluoromethyl-20-ethyl-2-homo-5-cis-13-trans prostadienoic acid |

While specific embodiments of this invention have been described with particularity herein, it will be understood that the invention embraces all changes and modifications of the particular compounds chosen for purposes of illustration herein which do not depart from the spirit and scope of the invention.

What is claimed is:

1. An optically active compound of the formula:

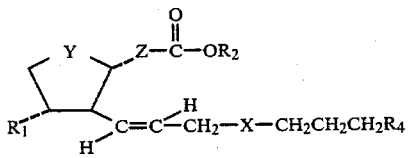

wherein Y is

X is:

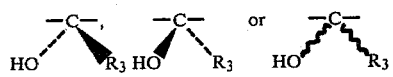

$R_1$ is hydrogen or hydroxyl;
$R_2$ is hydrogen or $C_1$ to $C_6$ alkyl;
$R_3$ is —$CH_2F$, —$CHF_2$, and —$CF_3$;
$R_4$ is hydrogen, and $C_1$ to $C_3$ alkyl;
Z is

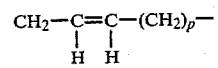

wherein p is 3 to 5, and the racemic mixture thereof; and when $R_1$ is hydrogen, the pharmaceutically acceptable salts thereof.

2. The compound according to claim 1, wherein Z is

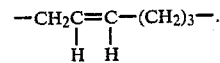

3. The compound according to claim 2, wherein $R_3$ is —$CH_2F$.

4. The compound according to claim 2, wherein $R_3$ is —$CHF_2$.

5. The compound according to claim 2, wherein $R_3$ is —$CF_3$.

6. The racemic compound according to claim 2, 11α,16α/β-dihydroxy-9-oxo-16-fluoromethyl-5-cis-13-transprostadienoic acid, the individual 16α and 16β-hydroxy racemates and the methyl esters thereof.

7. The optically active compounds according to claim 2, nat.-11α,16α/β-dihydroxy-9-oxo-16-fluoromethyl-5-cis-13-trans-prostadienoic acid, the individual 16α and 16β-hydroxy isomers, and the methyl esters thereof.

8. The racemic compounds according to claim 2, 11α,16α/β-dihydroxy-9-oxo-16-difluoromethyl-5-cis-13-trans-prostadienoic acid, the individual 16α and 16β-hydroxy racemates, and the methyl esters thereof.

9. The optically active compounds according to claim 2, nat.-11α,16α/β-dihydroxy-9-oxo-16-difluoromethyl-5-cis-13-trans-prostadienoic acid, the individual 16α and 16β-hydroxy isomers, and the methyl esters thereof.

10. The racemic compounds according to claim 2, 11α,16α/β-dihydroxy-9-oxo-16-trifluoromethyl-5-cis-13-trans prostadienoic acid, the individual 16α and 16β-hydroxy racemates, and the methyl esters thereof.

11. The optically active compouunds according to claim 2, nat.-11α,16α/β-dihydroxy-9-oxo-16-trifluoromethyl-5-cis-13-trans-prostadienoic acid, the individual 16α and 16β-hydroxy isomers, and the methyl esters thereof.

12. The optically active compound according to claim 6, 11α,16α-9-oxo-16-fluoromethyl-5-cis-13-trans-prostadienoic acid.

* * * * *